United States Patent
Kelly et al.

(10) Patent No.: US 10,695,481 B2
(45) Date of Patent: *Jun. 30, 2020

(54) HEMODIALYSIS SYSTEM HAVING A FLOW PATH WITH A CONTROLLED COMPLIANT VOLUME

(75) Inventors: Thomas D. Kelly, Highland Park, IL (US); SuPing Lyu, Maple Grove, MN (US); Bryant J. Pudil, Plymouth, MN (US); Thomas E. Meyer, Stillwater, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1392 days.

This patent is subject to a terminal disclaimer.

(21) Appl. No.: 13/565,733

(22) Filed: Aug. 2, 2012

(65) Prior Publication Data

US 2013/0199998 A1 Aug. 8, 2013

Related U.S. Application Data

(60) Provisional application No. 61/514,469, filed on Aug. 2, 2011.

(51) Int. Cl.
*A61M 1/34* (2006.01)
*A61M 1/16* (2006.01)

(52) U.S. Cl.
CPC ........ *A61M 1/3482* (2014.02); *A61M 1/1696* (2013.01); *A61M 2202/0021* (2013.01); *A61M 2202/0413* (2013.01)

(58) Field of Classification Search
CPC ........ A61M 1/16; A61M 1/1696; A61M 1/28; A61M 1/3679; A61M 1/281; A61M 1/284; A61M 1/34
See application file for complete search history.

(56) References Cited

U.S. PATENT DOCUMENTS

| | | |
|---|---|---|
| 3,091,098 A | 5/1963 | Bowers |
| 3,370,710 A | 2/1968 | Bluemle |

(Continued)

FOREIGN PATENT DOCUMENTS

| | | |
|---|---|---|
| CN | 103889481 A1 | 6/2014 |
| DE | 3215003 | 4/1985 |

(Continued)

OTHER PUBLICATIONS

Ruperez et al., Comparison of a Tubular Pulsatile Pump and a Volumetric Pump for Continuous Venovenous Renal Replacement Therapy in a Pediatric Animal Model, 51 ASAIO J. 372, 372-375 (2005).*

(Continued)

*Primary Examiner* — Krishnan S Menon
*Assistant Examiner* — Brad Gordon

(57) ABSTRACT

Systems and methods for the performance of kidney replacement therapy having or using a dialyzer, control components, sorbent cartridge and fluid reservoirs configured to be of a weight and size suitable to be worn or carried by an individual requiring treatment are disclosed. The system for performing kidney replacement therapy has a controlled compliance dialysis circuit, where a control pump controls the bi-directional movement of fluid across a dialysis membrane. The dialysis circuit and an extracorporeal circuit for circulating blood are in fluid communication through the dialysis membrane. The flux of fluid moving between the extracorporeal circuit and the dialysis circuit is modified by the rate at which the control pump is operating such that a rate of ultrafiltration and convective clearance can be controlled. The system provides for the monitoring of an inlet and outlet conductivity of the sorbent cartridge to provide a facility to quantify or monitor the removal of urea by the sorbent cartridge.

28 Claims, 32 Drawing Sheets

(56) References Cited

U.S. PATENT DOCUMENTS

| | | |
|---|---|---|
| 3,506,126 A | 4/1970 | Lindsay, Jr. |
| 3,608,729 A | 9/1971 | Haselden |
| 3,669,878 A | 6/1972 | Marantz |
| 3,669,880 A | 6/1972 | Marantz |
| 3,692,648 A | 9/1972 | Matloff |
| 3,776,819 A | 12/1973 | Williams |
| 3,809,241 A | 5/1974 | Alvine |
| 3,850,835 A | 11/1974 | Marantz |
| 3,884,808 A | 5/1975 | Scott |
| 3,939,069 A | 2/1976 | Granger |
| 3,976,574 A * | 8/1976 | White .............. A61M 1/16 210/188 |
| 3,989,622 A | 11/1976 | Marantz |
| 4,060,485 A | 11/1977 | Eaton |
| 4,094,775 A | 6/1978 | Mueller |
| 4,142,845 A | 3/1979 | Lepp |
| 4,201,555 A | 5/1980 | Tkach |
| 4,209,392 A | 6/1980 | Wallace |
| 4,269,708 A | 5/1981 | Bonomini |
| 4,316,725 A | 2/1982 | Hovind |
| 4,371,385 A | 2/1983 | Johnson |
| 4,374,382 A | 2/1983 | Markowitz |
| 4,381,999 A | 5/1983 | Boucher et al. |
| 4,430,098 A | 2/1984 | Bowman |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,650,587 A | 3/1987 | Polak et al. |
| 4,678,408 A | 7/1987 | Mason |
| 4,685,903 A | 8/1987 | Cable |
| 4,695,385 A | 9/1987 | Boag |
| 4,715,398 A | 12/1987 | Shouldice |
| 4,750,494 A | 6/1988 | King |
| 4,765,907 A | 8/1988 | Scott |
| 4,826,663 A | 5/1989 | Alberti |
| 4,828,693 A | 5/1989 | Lindsay et al. |
| 4,885,001 A | 12/1989 | Leppert |
| 4,900,308 A | 2/1990 | Verkaart |
| 4,915,713 A | 4/1990 | Buzza |
| 4,977,888 A | 12/1990 | Rietter |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Colman |
| 5,114,580 A | 5/1992 | Ahmad |
| 5,127,404 A | 7/1992 | Wyborny |
| 5,180,403 A | 1/1993 | Kogure |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,419,347 A | 5/1995 | Carruth |
| 5,445,610 A | 8/1995 | Evert |
| 5,468,388 A | 11/1995 | Goddard et al. |
| 5,591,344 A * | 1/1997 | Kenley .............. A61L 2/04 210/636 |
| 5,605,627 A * | 2/1997 | Carlsen .............. B01D 61/30 210/257.2 |
| 5,662,806 A | 9/1997 | Keshaviah et al. |
| 5,683,432 A | 11/1997 | Goedeke |
| 5,685,835 A | 11/1997 | Brugger |
| 5,702,536 A | 12/1997 | Carruth |
| 5,716,400 A | 2/1998 | Davidson |
| 5,744,031 A | 4/1998 | Bene |
| 5,762,782 A | 6/1998 | Kenley et al. |
| 5,849,179 A | 12/1998 | Emerson et al. |
| 5,858,186 A | 1/1999 | Glass |
| 5,863,421 A | 1/1999 | Peter |
| 5,938,634 A | 8/1999 | Packard |
| 5,938,938 A * | 8/1999 | Bosetto .............. A61M 1/16 210/739 |
| 5,944,684 A | 8/1999 | Roberts |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,230,059 B1 | 5/2001 | Duffin |
| 6,248,093 B1 | 6/2001 | Moberg |
| 6,251,167 B1 | 6/2001 | Berson |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,521,184 B1 | 2/2003 | Glass |
| 6,554,798 B1 | 4/2003 | Mann |
| 6,555,986 B2 | 4/2003 | Moberg |
| 6,565,525 B1 | 5/2003 | Burbank et al. |
| 6,585,675 B1 | 7/2003 | O'Mahony et al. |
| 6,589,229 B1 | 7/2003 | Connelly |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,726,647 B1 | 4/2004 | Sternby |
| 6,773,412 B2 | 8/2004 | O'Mahony et al. |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,878,283 B2 | 4/2005 | Thompson |
| 6,890,315 B1 | 5/2005 | Levin et al. |
| 6,923,782 B2 | 8/2005 | O'Mahony et al. |
| 6,960,179 B2 | 11/2005 | Gura |
| 7,023,359 B2 | 4/2006 | Goetz |
| 7,029,456 B2 | 4/2006 | Ware et al. |
| 7,074,332 B2 | 7/2006 | Summerton |
| 7,077,819 B1 | 7/2006 | Goldau |
| 7,128,750 B1 | 10/2006 | Stergiopulos |
| 7,169,303 B2 | 1/2007 | Sullivan |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,326,576 B2 | 2/2008 | Womble et al. |
| 7,384,543 B2 | 6/2008 | Jonsson et al. |
| 7,462,161 B2 | 12/2008 | O'Mahony et al. |
| 7,500,958 B2 | 3/2009 | Asbrink |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers et al. |
| 7,776,210 B2 | 8/2010 | Rosenbaum et al. |
| 7,785,463 B2 | 8/2010 | Bissler |
| 7,790,103 B2 | 9/2010 | Shah |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |

(56) References Cited

U.S. PATENT DOCUMENTS

| | | | |
|---|---|---|---|
| 7,955,291 | B2 | 6/2011 | Sternby |
| 7,967,022 | B2 | 6/2011 | Grant |
| 7,981,082 | B2 | 7/2011 | Wang et al. |
| 8,002,726 | B2 | 8/2011 | Karoor |
| 8,034,161 | B2 | 10/2011 | Gura et al. |
| 8,070,709 | B2 | 12/2011 | Childers |
| 8,080,161 | B2 | 12/2011 | Ding et al. |
| 8,096,969 | B2 | 1/2012 | Roberts |
| 8,182,673 | B2 | 5/2012 | Childers et al. |
| 8,183,046 | B2 | 5/2012 | Lu |
| 8,187,250 | B2 | 5/2012 | Roberts |
| 8,197,439 | B2 | 6/2012 | Wang |
| 8,202,241 | B2 | 6/2012 | Karakama |
| 8,206,591 | B2 | 6/2012 | Kotanko et al. |
| 8,211,048 | B2 | 7/2012 | Szamosfalvi et al. |
| 8,221,529 | B2 | 7/2012 | Childers et al. |
| 8,226,595 | B2 | 7/2012 | Childers et al. |
| 8,246,826 | B2 | 8/2012 | Wilt |
| 8,267,881 | B2 | 9/2012 | O'Mahony et al. |
| 8,273,049 | B2 | 9/2012 | Demers |
| 8,292,594 | B2 | 10/2012 | Tracey |
| 8,313,642 | B2 | 11/2012 | Yu |
| 8,317,492 | B2 | 11/2012 | Demers |
| 8,357,113 | B2 | 1/2013 | Childers |
| 8,357,298 | B2 | 1/2013 | Demers et al. |
| 8,366,316 | B2 | 2/2013 | Kamen |
| 8,366,655 | B2 | 2/2013 | Kamen |
| 8,376,999 | B2 | 2/2013 | Busby et al. |
| 8,377,012 | B2 | 2/2013 | Chapman et al. |
| 8,377,308 | B2 | 2/2013 | Kreymann et al. |
| 8,388,567 | B2 | 3/2013 | Rovatti |
| 8,409,441 | B2 | 4/2013 | Wilt |
| 8,449,487 | B2 | 5/2013 | Hovland et al. |
| 8,491,517 | B2 | 7/2013 | Karoor |
| 8,496,809 | B2 | 7/2013 | Roger |
| 8,499,780 | B2 | 8/2013 | Wilt |
| 8,500,672 | B2 | 8/2013 | Caleffi |
| 8,500,676 | B2 | 8/2013 | Jansson |
| 8,500,994 | B2 | 8/2013 | Weaver |
| 8,512,271 | B2 | 8/2013 | Moissl |
| 8,518,258 | B2 | 8/2013 | Balschat |
| 8,518,260 | B2 | 8/2013 | Raimann |
| 8,521,482 | B2 | 8/2013 | Akonur |
| 8,535,525 | B2 | 9/2013 | Heyes |
| 8,560,510 | B2 | 10/2013 | Brueggerhoff |
| 8,562,822 | B2 | 10/2013 | Roger |
| 8,580,112 | B2 | 11/2013 | Updyke |
| 8,597,227 | B2 | 12/2013 | Childers |
| 8,696,626 | B2 | 4/2014 | Kirsch |
| 8,903,492 | B2 | 12/2014 | Soykan |
| 8,906,240 | B2 | 12/2014 | Crnkovich |
| 2002/0042561 | A1 | 4/2002 | Schulman |
| 2002/0045851 | A1 | 4/2002 | Suzuki |
| 2002/0062098 | A1 | 5/2002 | Cavicchioli et al. |
| 2002/0104800 | A1 | 8/2002 | Collins |
| 2002/0112609 | A1* | 8/2002 | Wong .............................. 96/131 |
| 2003/0010717 | A1 | 1/2003 | Brugger |
| 2003/0080059 | A1 | 5/2003 | Peterson |
| 2003/0097086 | A1 | 5/2003 | Gura |
| 2003/0105435 | A1 | 6/2003 | Taylor |
| 2003/0114787 | A1 | 6/2003 | Gura |
| 2003/0138348 | A1 | 7/2003 | Bell et al. |
| 2004/0019312 | A1* | 1/2004 | Childers .............. A61M 1/1656 604/4.01 |
| 2004/0030277 | A1 | 2/2004 | O'Mahony et al. |
| 2004/0037986 | A1 | 2/2004 | Houston et al. |
| 2004/0054315 | A1 | 3/2004 | Levin et al. |
| 2004/0068219 | A1 | 4/2004 | Summerton |
| 2004/0082903 | A1* | 4/2004 | Micheli .......................... 604/29 |
| 2004/0084358 | A1 | 5/2004 | O'Mahony et al. |
| 2004/0099593 | A1 | 5/2004 | DePaolis |
| 2004/0143173 | A1 | 7/2004 | Reghabi |
| 2004/0147900 | A1 | 7/2004 | Polaschegg |
| 2004/0168969 | A1 | 9/2004 | Sternby |
| 2004/0215090 | A1 | 10/2004 | Erkkila |
| 2005/0065760 | A1 | 3/2005 | Murtfeldt |
| 2005/0113796 | A1 | 5/2005 | Taylor |
| 2005/0115898 | A1 | 6/2005 | Sternby |
| 2005/0126961 | A1 | 6/2005 | Bissler |
| 2005/0131331 | A1 | 6/2005 | Kelly |
| 2005/0131332 | A1 | 6/2005 | Kelly |
| 2005/0126998 | A1 | 7/2005 | Childers |
| 2005/0150832 | A1 | 7/2005 | Tsukamoto |
| 2005/0153904 | A1* | 7/2005 | Fager ................... A61K 31/195 210/646 |
| 2005/0230313 | A1 | 10/2005 | O'Mahony et al. |
| 2005/0234381 | A1 | 10/2005 | Niemetz |
| 2005/0274658 | A1 | 12/2005 | Rosenbaum |
| 2006/0025661 | A1 | 2/2006 | Sweeney |
| 2006/0217771 | A1 | 2/2006 | Soykan |
| 2006/0054489 | A1 | 3/2006 | Denes |
| 2006/0076295 | A1 | 4/2006 | Leonard |
| 2006/0157335 | A1 | 7/2006 | Levine |
| 2006/0157413 | A1* | 7/2006 | Bene ....................... A61M 1/16 210/646 |
| 2006/0189926 | A1 | 8/2006 | Hall et al. |
| 2006/0195064 | A1 | 8/2006 | Plahey |
| 2006/0226079 | A1 | 10/2006 | Mori |
| 2006/0241709 | A1 | 10/2006 | Soykan |
| 2006/0264894 | A1 | 11/2006 | Moberg |
| 2007/0007208 | A1 | 1/2007 | Brugger |
| 2007/0055296 | A1 | 3/2007 | Stergiopulos |
| 2007/0066928 | A1 | 3/2007 | Lannoy |
| 2007/0072285 | A1 | 3/2007 | Barringer |
| 2007/0138011 | A1 | 6/2007 | Hofmann |
| 2007/0175827 | A1 | 8/2007 | Wariar |
| 2007/0179431 | A1 | 8/2007 | Roberts |
| 2007/0213653 | A1 | 9/2007 | Childers |
| 2007/0213665 | A1 | 9/2007 | Curtin |
| 2007/0215545 | A1 | 9/2007 | Bissler |
| 2007/0255250 | A1 | 11/2007 | Moberg |
| 2008/0006570 | A1 | 1/2008 | Gura |
| 2008/0015493 | A1 | 1/2008 | Childers et al. |
| 2008/0021337 | A1 | 1/2008 | Li |
| 2008/0053905 | A9 | 3/2008 | Brugger |
| 2008/0067132 | A1 | 3/2008 | Ross |
| 2008/0093276 | A1 | 4/2008 | Roger |
| 2008/0154543 | A1 | 6/2008 | Rajagopal |
| 2008/0215247 | A1 | 9/2008 | Tonelli |
| 2008/0217245 | A1* | 9/2008 | Rambod .................. A61M 1/16 210/637 |
| 2008/0230473 | A1 | 9/2008 | Herbst |
| 2008/0253427 | A1 | 10/2008 | Kamen |
| 2009/0012450 | A1 | 1/2009 | Shah |
| 2009/0020471 | A1 | 1/2009 | Tsukamoto |
| 2009/0078636 | A1 | 3/2009 | Uchi |
| 2009/0084721 | A1 | 4/2009 | Yardimci |
| 2009/0101549 | A1 | 4/2009 | Kamen |
| 2009/0101577 | A1 | 4/2009 | Fulkerson |
| 2009/0105629 | A1 | 4/2009 | Grant |
| 2009/0124963 | A1 | 5/2009 | Hogard |
| 2009/0127193 | A1 | 5/2009 | Updyke et al. |
| 2009/0131858 | A1 | 5/2009 | Fissell |
| 2009/0149795 | A1 | 6/2009 | O'Mahony et al. |
| 2009/0157877 | A1 | 6/2009 | Baek |
| 2009/0171261 | A1 | 7/2009 | Sternby |
| 2009/0182263 | A1 | 7/2009 | Burbank |
| 2009/0187138 | A1 | 7/2009 | Lundtveit |
| 2009/0216045 | A1 | 8/2009 | Singh |
| 2009/0223539 | A1 | 9/2009 | Gibbel |
| 2009/0275849 | A1 | 11/2009 | Stewart |
| 2009/0275883 | A1 | 11/2009 | Chapman |
| 2009/0281484 | A1 | 11/2009 | Childers |
| 2009/0282980 | A1 | 11/2009 | Gura et al. |
| 2009/0314063 | A1 | 12/2009 | Sternby |
| 2010/0004588 | A1 | 1/2010 | Yeh |
| 2010/0007838 | A1 | 1/2010 | Fujimoto |
| 2010/0010429 | A1 | 1/2010 | Childers |
| 2010/0018923 | A1 | 1/2010 | Rohde et al. |
| 2010/0022936 | A1 | 1/2010 | Gura |
| 2010/0030151 | A1 | 2/2010 | Kirsch |
| 2010/0042035 | A1 | 2/2010 | Moissl |
| 2010/0051529 | A1 | 3/2010 | Grant et al. |
| 2010/0076364 | A1 | 3/2010 | O'Mahony et al. |

(56) References Cited

U.S. PATENT DOCUMENTS

| | | |
|---|---|---|
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0114001 A1 | 5/2010 | O'Mahony |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0168641 A1 | 7/2010 | O'Mahony et al. |
| 2010/0192686 A1 | 8/2010 | Kamen |
| 2010/0199670 A1 | 8/2010 | Robertson |
| 2010/0217180 A1 | 8/2010 | Akonur |
| 2010/0224492 A1 | 9/2010 | Ding |
| 2010/0234795 A1 | 9/2010 | Wallenas |
| 2010/0241045 A1 | 9/2010 | Kelly |
| 2010/0274171 A1 | 10/2010 | Caleffi |
| 2010/0312174 A1 | 12/2010 | Hoffman |
| 2010/0326911 A1 | 12/2010 | Rosenbaum et al. |
| 2010/0327586 A1 | 12/2010 | Mardirossian |
| 2011/0017665 A1 | 1/2011 | Updyke et al. |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0184340 A1 | 7/2011 | Tan |
| 2011/0189048 A1 | 8/2011 | Curtis |
| 2011/0220562 A1 | 9/2011 | Beiriger |
| 2011/0272337 A1 | 11/2011 | Palmer |
| 2011/0315611 A1 | 12/2011 | Fulkerson |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0006128 A1 | 1/2013 | Olde et al. |
| 2013/0018301 A1 | 1/2013 | Weaver |
| 2013/0019994 A1 | 1/2013 | Schaer |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0030347 A1 | 1/2013 | Sugioka |
| 2013/0030348 A1 | 1/2013 | Lauer |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1* | 9/2013 | Jonsson et al. ............... 210/646 |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |

FOREIGN PATENT DOCUMENTS

| | | |
|---|---|---|
| EP | 0022370 A1 | 1/1981 |
| EP | 0187109 | 7/1986 |
| EP | 266795 A2 | 11/1987 |
| EP | 0 614 081 A1 | 10/1993 |
| EP | 0298587 | 6/1994 |
| EP | 0743071 | 11/1996 |
| EP | 1124599 | 5/2000 |
| EP | 0 614 081 B1 | 7/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 1490129 | 9/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |

(56) References Cited

FOREIGN PATENT DOCUMENTS

| | | |
|---|---|---|
| EP | 2701580 | 11/2012 |
| EP | 2701595 | 11/2012 |
| EP | 1684825 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 1787666 | 11/2015 |
| FR | 2237639 | 2/1977 |
| JP | 2002306904 | 10/2002 |
| JP | 5099464 | 10/2012 |
| WO | WO9106326 A1 | 5/1991 |
| WO | 1996040313 | 12/1996 |
| WO | 9937342 | 7/1999 |
| WO | WO2000038591 A2 | 7/2000 |
| WO | 0057935 | 10/2000 |
| WO | 200066197 A1 | 11/2000 |
| WO | 2000066197 | 11/2000 |
| WO | 200170307 A1 | 9/2001 |
| WO | 2001085295 A2 | 9/2001 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004105589 A2 | 12/2004 |
| WO | 2005044339 | 5/2005 |
| WO | 2004105589 A3 | 6/2005 |
| WO | 2005061026 | 7/2005 |
| WO | 2005123230 A2 | 12/2005 |
| WO | 2006023589 | 3/2006 |
| WO | 2007010164 A2 | 1/2007 |
| WO | 2007089855 A2 | 8/2007 |
| WO | 2007146162 A2 | 12/2007 |
| WO | 2007146162 A3 | 12/2007 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009064984 | 5/2009 |
| WO | 2009071103 | 6/2009 |
| WO | 2009094184 | 7/2009 |
| WO | 2009132839 A1 | 11/2009 |
| WO | 2009157877 A1 | 12/2009 |
| WO | 2009157878 A1 | 12/2009 |
| WO | WO 2009/157877 A1 | 12/2009 |
| WO | 2010028860 | 3/2010 |
| WO | 2010028860 A1 | 3/2010 |
| WO | 2010042666 | 4/2010 |
| WO | 2010042666 A2 | 4/2010 |
| WO | 2010052705 A1 | 5/2010 |
| WO | 2010062698 | 6/2010 |
| WO | 2010096659 | 10/2010 |
| WO | 2010121820 | 10/2010 |
| WO | 2011017215 A1 | 2/2011 |
| WO | 2011025705 A1 | 3/2011 |
| WO | 2012026978 | 3/2012 |
| WO | 2012042323 | 4/2012 |
| WO | 2012050781 | 4/2012 |
| WO | 2012051996 | 4/2012 |
| WO | 2012067585 | 5/2012 |
| WO | 2010042666 A3 | 6/2012 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013025844 | 2/2013 |
| WO | 2013025844 A2 | 2/2013 |
| WO | 2013027214 | 2/2013 |
| WO | 2013028809 A2 | 2/2013 |
| WO | 2013028809 A3 | 2/2013 |
| WO | WO/2013/019994 A2 | 2/2013 |
| WO | WO2013019179 A1 | 2/2013 |
| WO | WO2013022024 A1 | 2/2013 |
| WO | WO2013022837 A1 | 2/2013 |
| WO | WO2013030642 A1 | 3/2013 |
| WO | WO2013030643 A1 | 3/2013 |
| WO | 2013019994 A3 | 4/2013 |
| WO | 2013025844 A3 | 5/2013 |
| WO | WO2012162515 A3 | 5/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | 2014117000 | 7/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

St. Peter et al., Liver and kidney preservation by perfusion, 359 The Lancet 604, 606 (2002).*
Dasselaar et al., Measurement of relative blood volume changes during haemodialysis: merits and limitations, 20 Nephrol. Dial. Transpl. 2043, 2043-2044 (2005).*
Dasselaar et al., Measurement of relative blood volume changes during haemodialysis: merits and limitations, 20 Nephrol. Dial. Transpl. 2043, 2043-2044 (2005). (Year: 2005).*
U.S. Appl. No. 13/757,693, Medtronic, Inc.
U.S. Appl. No. 13/757,709, Medtronic, Inc.
U.S. Appl. No. 13/757,728, Medtronic, Inc.
U.S. Appl. No. 61/760,033, Medtronic, Inc.
U.S. Appl. No. 13/836,538, Medtronic, Inc.
U.S. Appl. No. 13/565,733, Medtronic, Inc.
U.S. Appl. No. 13/100,847, filed Nov. 10, 2011, C-Tech BioMedical, Inc.
Culleton, BF et al. Effect of Frequent Nocturnal Hemodialysis vs. Conventional Hemodialysis on Left Ventricular Mass and Quality of Life. 2007 Journal of the American Medical.
Gotch FA, Sargent JA "A mechanistic analysis of the National Cooperative Dialysis Study (NCDS)", Kidney int. 1985; 28:526-34.
Daugirdas JT, "Second generation logarithmic estimates of single-pool variable volume Kt/V: and analysis of error." J Am Soc Nephrol. 1993; 4:1205-13.
Steil et al., Int'l Journ Artif Organs, 1993, In Vivo Verification of an Automatic Noninvasive System for Real Time Kt Evaluation, ASAIO J., 1993, 39:M348-52.
International Search Report and Written Opinion in App. No. PCT/US2012/049398 dated Feb. 25, 2013.
Office Action in European App. No. 12819714.2 dated Aug. 5, 2016.
Office Action in Chinese Application No. 201280047921.2 dated Jun. 11, 2015.
Examination report for Australian Application No. AU2014212135 dated May 25, 2017.
Office Action for Chinese Application 20148007136.3, dated Jun. 15, 2017.

(56) References Cited

OTHER PUBLICATIONS

European Office Action in Application 14746793.0 dated Apr. 13, 2017.
Franks, Gene, Cabon Filtration: What it does, What it doesn't, Mar. 14, 2012, pp. 1-3.
EP Search Report for Application No. 16204175.0 dated Mar. 29, 2017.
Office Action for Chinese Application 201510713880.1 dated Apr. 1, 2017.
Written Opinion of the International Searching Authority for PCT/US2012/049398 dated Feb. 25, 2013.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Siegenthaler, et al., Pulmonary fluid status monitoring with intrathoracic impedance, Journal of Clinical Monitoring and Computing, 24:449-451, 2010.
Wang, Fundamentals of intrathoracic impedance monitoring in heart failure, Am. J. Cardiology, 2007, 3G-10G: Suppl.
Gambro AK 96 Dialysis Machine Operator's Manual, Dec. 2012.
European Search Report 12819714.2-1651/2739325 PCT/US2012049398, dated Jun. 12, 2015.
Office Action in U.S. Appl. No. 13/586,824 dated Dec. 21, 2015.
Office Action in U.S. Appl. No. 13/586,824 dated Jun. 4, 2016.
Office Action in U.S. Appl. No. 13/791,755 dated Apr. 20, 2015.
Office Action in U.S. Appl. No. 13/791,755 dated Sep. 10, 2015.
Office Action in U.S. Appl. No. 13/791,755 dated Mar. 16, 2016.
Office Action in U.S. Appl. No. 13/791,755 dated Aug. 9, 2016.
U.S. Appl. No. 13/757,693, filed Feb. 1, 2013.
PCT/US2014/14343 Int'l Search Report & Written Opinion, dated May 9, 2014.
EP 14746791 Supplementary European Search Report dated Aug. 19, 2016.
PCT/US2014/014350 International Search Report and Written Opinion dated May 2014.
EP 14746793 Supplementary European Search Report dated Aug. 18, 2016.
U.S. Appl. No. 29/446,285, filed Feb. 1, 2013.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2014/014345 International Search Report and Written Opinion, dated May 2014.
Leifer et al., 'A Study on the Temperature Variation of Rise Velocity for Large Clean Bubbles,' J. Atmospheric & Oceanic Tech., vol. 17, pp. 1392-1402.
Talaia, 'Terminal Velocity of a Bubble Rise in a Liquid Column,' World Acad. of Sci., Engineering & Tech., vol. 28, pp. 264-268.
The FHN Trial Group. In-Center. Hemodialysis Six Times per Week versus Three Times per Week, New England Journal of Medicine, 2010 Abstract.
PCT/US2014/014357 International Search Report and Written Opinion.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/757,792, filed Feb. 2, 2013.
U.S. Appl. No. 13/837,287, filed Mar. 15, 2013.
U.S. Appl. No. 13/757,794, filed Feb. 2, 2013.
Weissman, S., et al., "Hydroxyurea-induced hepatitis in human immunodeficiency virus-positive patients." Clin. Infec. Dis, (Jul. 29, 1999): 223-224.
MacLean, et, al., Effects of hindlimb contraction on pressor and muscle interstitial metabolite responses in the cat, J. App. Physiol., 1998, 1583-1592, 85(4).
Overgaard, et. al., Activity-induced recovery of excitability in K+-depressed rat soieus muscle, Am. J. P.
Overgaard. et. al., Relations between excitability and contractility in rate soleus'muscle: role of the NA+-K+ pump and NA+-K-S gradients. Journal of Physiology, 1999, 215-225, 518(1).
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Roberts M, The regenerative dialysis (REDY) sorbent system. Nephrology, 1998, 275-278:4.
Ronco et al. 2008, 'Cardiorenal Syndrome,' Journal American College Cardiology, 52:1527-1539, Abstract.
U.S. Appl. No. 61/480,544.
PCT/US2014/067650 International Search Report Written Opinion dated Mar. 9, 2015.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, dated Aug. 13, 2013.
PCT/US/2012/034329, International Search Report, dated Dec. 3, 2012.
PCT/US2012/034331, International Search Report, dated Jul. 9, 2012.
PCT/US2012/034332, International Search Report, dated Jul. 5, 2012.
PCT/US2012/034334, International Search Report, dated Jul. 6, 2012.
PCT/US2012/034335, International Search Report, dated Sep. 5, 2012.
Redfield, et. al, Restoration of renal response to atria! natriuretic factor in experimental low-output heat failure, Am. J. Physiol., 1989, R917-923:257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Coast, et al. 1990, An approach to Cardiac Arrhythmia analysis Using Hidden Markov Models, IEEE Transactions on Biomedical Engineering. 1990, 37 (9):826-835.
U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
U.S. Appl. No. 61/480,532.
PCT/US2012/034330, International Preliminary Report on Patentability, dated Oct. 29, 2013.
PCT Application, PCT/US20013/020404, filed Jan. 4, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, dated Oct. 29, 2013.
PCT/US2012/034333, International Search Report, dated Aug. 29, 2013.
U.S. Appl. No. 13/424,429.

(56) References Cited

OTHER PUBLICATIONS

U.S. Appl. No. 13/424,479.
U.S. Appl. No. 13/424,525.
U.S. Appl. No. 61/480,528.
U.S. Appl. No. 61/480,530.
U.S. Appl. No. 61/480,535.
U.S. Appl. No. 61/480,539.
U.S. Appl. No. 61/480,541.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Bleyer, et. al., Sudden and cardiac death rated in hemodialysis patients, Kidney International. 1999, 1553-1559: 55.
EP 14746799 Supplementary European Seach Report dated Aug. 18, 2016.
EP13182115.9-1651 European Search Report, dated Feb. 3, 2014.
International Search Report for PCT/US2015/060090 date of completion is Feb. 9, 2016 (3 pages).
Marchant, et. al., In vivo Biocompatibility Studies 1: The Cage Implant System and a Biodegradable Hydrogel, J. Biomed. Mat. Res., 1983, 301-325: 17.
Bleyer, et al, Kidney International. Jun. 2006; 69(12):2268-2273.
PCT/US2012/025711, International Search Report dated Jul. 4, 2012.
PCT/US2012/051011, International Search Report, dated Jan. 17, 2014.
Ralph T. Yang, Adsorbents: Fundamentals and Applications 109 (2003).
Henny H. Billett, Hemoglobin and Hematocrit, in Clinical Methods: The History, Physical, and Laboratory Examinations 719(HK Walker, WD Hall, & JW Hurst ed., 1990).
Office Action for Chinese Application 201510761050.6 dated Aug. 2, 2017.
Examination report for Australian Application 2015361083 dated Jul. 20, 2017.
International Preliminary Report on Patentability for PCT2015/060090 dated Jun. 13, 2017.
Indian Office Action for App. No. 244/KOLNP/2014, dated Feb. 12, 2020.

\* cited by examiner

- ▶◀ Closed valve
- ▶◁ Open valve
- ● Pressure sensor
- ▢ Ammonium sensor (specific, pH or conductivity)
- ▪ Blood leak detector
- ○ Air-saline detector
- ---- Inactive flow path
- —— Active flow path

- Closed valve
- Open valve
- Pressure sensor
- Ammonium sensor (specific, pH or conductivity)
- Blood leak detector
- Air-saline detector
- ---- Inactive flow path
- —— Active flow path

HEMODIALYSIS SYSTEM HAVING A FLOW PATH WITH A CONTROLLED COMPLIANT VOLUME

CROSS-REFERENCE TO RELATED APPLICATIONS

This application claims benefit of priority to U.S. Provisional Patent Application No. 61/514,469 filed on Aug. 2, 2011, which is incorporated herein by reference.

FIELD OF THE INVENTION

This disclosure relates to an apparatus for hemodialysis and hemofiltration for the treatment of pathological conditions such as End Stage Renal Disease (ESRD) on a frequent or continuous basis. The systems and methods include a system having a dialyzer, control components, dialysate regeneration cartridge and fluid reservoirs configured to be of a weight and size to be worn or carried by an individual requiring treatment. The disclosure further relates to the treatment of Chronic Kidney Disease (CKD) through methods and apparatuses that allow an individual to remain ambulatory during treatment. The disclosure further relates to the treatment of ESRD through methods and apparatuses that are small, lightweight, and portable.

BACKGROUND

Chronic Kidney Disease (CKD), also known as chronic renal disease, is a progressive loss in renal function over a period of months or years. As the disease progresses, a patient with severe renal failure can develop many symptoms that if left untreated may eventually result in death. The most severe stage of CKD is End Stage Renal Disease (ESRD), which occurs when the glomerular filtration rate (GFR) is lower than about 15 ml/min/1.73 m$^2$. ESRD, also referred to as kidney failure or renal failure, is the medical condition wherein a person's kidneys fail to sufficiently remove toxins, waste products, and excess fluid, and to maintain proper electrolyte levels. In the US, the two main causes of CKD are diabetes and high blood pressure, which are responsible for up to two-thirds of the cases. Heart disease is the leading cause of death for all people having CKD.

Current treatments for CKD seek to manage comorbidities and, if possible, slow the progression of the disease. However, as the disease progresses, renal function decreases and eventually renal replacement therapy is employed to compensate for lost kidney function. Renal replacement therapy typically entails transplantation of a new kidney, or dialysis. Kidney dialysis is a medical procedure that is performed to aid or replace some of the kidney functions in severe renal failure. Hemodialysis, hemofiltration, hemodiafiltration, and peritoneal dialysis are all replacement therapies for patients who have lost most or all of their kidney function. Dialysis can remove many of the toxins and wastes that the natural kidney would remove. In addition, these therapies are used to balance the electrolyte or blood salt levels and to remove excess fluid that accumulates in patients with renal failure.

Hemodialysis treatment can be performed to remove waste products from the blood that are no longer being effectively removed by the kidneys, such as urea, creatinine and phosphates. Although the population of patients afflicted with CKD grows each year, there is no cure. The excess fluid accumulated in patients suffering from renal failure is generally removed by direct ultrafiltration or by the ultrafiltration action of a dialysis procedure.

Hemodialysis procedures are usually carried out three times a week in three to five hour sessions. Dialysis emulates kidney function by removing waste solutes, excess electrolytes and excess fluid from a patient's blood. During dialysis, the patient's blood that contains a high concentration of waste solutes is exposed to a semi-permeable membrane in contact with a solute-deficient dialysis solution (dialysate). Solute removal and electrolyte balancing is accomplished via diffusion across the membrane, while fluid removal is accomplished via pressure-driven ultrafiltration. Once the blood is purified, it is then returned to the patient. Although effective at removing wastes from blood, dialysis treatments are administered intermittently and therefore do not emulate the continuous function of a natural kidney. Moreover, there are many inconveniences associated with dialysis, such as the necessity of committing to time consuming, thrice-weekly treatments.

The mortality rate of ESRD patients who receive traditional hemodialysis therapy is 23% per year with an even higher mortality rate among diabetic patients. Excessive fluid can accumulate in patients suffering from ESRD. Fluid accumulates in ESRD patients because the kidneys can no longer effectively remove water and other compounds from the body. The fluid accumulates first in the blood and then accumulates throughout the body resulting in swelling of the extremities and other tissues as edema. This accumulation of fluid causes increased stress on the heart, in turn causing significant increases in blood pressure or hypertension, which can lead to heart failure.

Although hemodialysis removes excess fluid, the thrice-weekly hemodialysis schedule creates variations in the patient's waste removal, impurity removal, fluid removal and electrolyte balance. These variations result in patient complications and the high rates of patient morbidity and mortality. Since the mid 1990s a number of physicians have prescribed treatment regimens with increased dialysis frequency and treatment time to try to eliminate the problems associated with the thrice-weekly hemodialysis schedule. Two recent randomized controlled clinical studies have shown statistically significant benefits of a more frequent dialysis regimen. Culleton et al. (Culleton, B F et al. Effect of Frequent Nocturnal Hemodialysis vs. Conventional Hemodialysis on Left Ventricular Mass and Quality of Life. 2007 Journal of the American Medical Association 298 (11)) reported that when compared with conventional hemodialysis (3 times weekly) daily nocturnal hemodialysis improved left ventricular mass (a surrogate for mortality), reduced the need for blood pressure medications and improved some measures of mineral metabolism. The FHN trial (The FHN Trial Group. In-Center Hemodialysis Six Times per Week versus Three Times per Week, New England Journal of Medicine, 2010) was a comparison of increased treatment frequency of 5.2 hemodialysis treatments a week compared with the traditional thrice-weekly regimen: "Frequent hemodialysis, as compared with conventional hemodialysis, was associated with favorable results with respect to the composite outcomes of death or change in left ventricular mass and death or change in a physical-health composite score." Based on this data it would be desirable to have a hemodialysis system that would allow kidney patients to dialyze from five to seven days a week if not continuously.

Despite the clinical results from the Culleton and FHN research, few patients presently undergo a higher frequency of dialysis treatment. More frequent hemodialysis is only used on a small part of the patient population due to the burden and cost of more frequent therapies. Even the thrice weekly-regime is a significant burden to ESRD patients, and an increase in treatment frequency can often be difficult due to the deficiencies in known devices and the cost of the additional treatments. Most dialysis is performed in a dialysis center; hence, there is a need for the practical implementation of more frequent hemodialysis using a simple, wearable/portable, and safe technology that can be used by a patient at home.

Although dialysis equipment for home use is available, a patient must still remain relatively immobile during the course of treatment due to the non-portable nature of such dialysis equipment. Typical home-dialysis equipment employs an amount of dialysis fluid greater than 20 liters and typically up to 120 to 200 liters that require a dedicated water system. Due to the volume and weight requirements of the needed dialysis fluid, even during home-based dialysis treatment a patient is not ambulatory during treatment, which may affect how often treatment is undertaken.

The large volume of dialysate fluid required for dialysis is in part attributable to the large quantity of solution necessary for the diffusion of waste products removed and the balancing of electrolytes within the dialysate from the blood of a dialysis patient. Regeneration of spent dialysate is one way to reduce the total volume of a dialysis system by eliminating the need for a large reserve of fresh dialysate. In order for spent dialysate to be reused, accumulated waste products and impurities must be removed from the spent dialysate, and the composition and pH of the regenerated dialysate must be regulated for physiological compatibility. Devices that regenerate spent dialysis fluid are primarily directed toward the removal of urea, ammonium ions, uric acid, creatinine, and phosphate via various sorbents. For example, the Recirculating Dialysate System ("REDY system"), which was introduced in the 1970s, employs a sorbent cartridge through which spent dialysate is recirculated and regenerated. However, the regenerated dialysate produced by REDY systems is subject to variations in pH and sodium concentrations non-conducive to physiological norms. Additionally, REDY systems have limited or no ability to remove sulfates, and are not portable.

Moreover, traditional dialysis systems employing sorbent technology, such as the REDY system usually employ low-flux dialyzers and adjust dialysate pressure to achieve net patient fluid removal. The UF coefficient of a dialyzer specifies the rate of filtration through the dialyzer due to pressure differences across the dialyzer membrane, typically called the trans-membrane pressure. The trans-membrane pressure is calculated by the formula TMP=((Blood Inlet Pressure+Blood Outlet Pressure)/2)−((Dialysate Inlet Pressure+Dialysate Outlet Pressure)/2). This formula is usually shortened to TMP=Venous Return Pressure−Dialysate Pressure. Low flux hemodialyzers have a UF coefficient of less than 8 ml of water flux per hour per mmHg of trans-membrane pressure. To illustrate fluid removal with the traditional sorbent system, a typical low flux dialyzer could have a UF coefficient of 4 mL/hr/mmHg. To calculate the pressure necessary to achieve the rate of fluid removal, the desired hourly fluid removal is divided by the dialyzer UF coefficient. For example, an hourly rate of 0.5 L/hr yields a required trans-membrane pressure (TMP) of 125 mmHg if the UF coefficient is 4 mL/hr/mmHg. 125 mmHg is the trans-membrane pressure required to remove fluid at a rate of 0.5 L per hour. The venous pressure is a function of the blood flow rate and the blood return restriction (needle and access). As the Venous Return Pressure cannot be set, to control the fluid removal rate it is necessary calculate the required dialysate pressure. The operator calculates dialysate pressure via the formula Dialysate Pressure=Venous Pressure−TMP, if the venous return pressure were 75 mmHg, (DP=75−125=−50 mmHg). In this example the user must adjust the dialysate pressure to −50 mmHg to achieve the TMP of 125 mmHg. The venous pressure fluctuates during treatment so the operator must adjust the dialysate pressure on a regular basis, which is not suitable for a non-medical professional or a home patient. With high-flux dialyzers, pressure alone is not accurate enough to control ultrafiltration because fluid moves more freely across the dialyzer membrane. To control ultrafiltration in conventional hemodialysis using high-flux dialyzers, balancing chambers, flow sensors or other methods to balance flow to and from the dialyzer are employed. In CRRT (continuous blood purification machine) equipment, pumps controlled by precise scales are required to control the flow to and from the dialyzer very accurately.

Development of dialysate recirculating techniques has resulted in systems that employ a variety of sorbent media, including activated carbon, urease, and zirconium-, aluminum-, and magnesium-based materials. Yet one of the problems associated with sorbent regeneration of spent dialysate is the buildup of sodium ions released as a byproduct of the adsorption process, thus necessitating a high degree of sodium concentration control which has yet to be achieved by current wearable or portable dialysis systems. Deionization resins have been explored to combat the buildup of sodium ions with mixed results. Further, electrolytes such as calcium, magnesium, and potassium are removed from spent dialysate by sorbent and deionization media and must be added back to the dialysate prior to reuse. Additionally, carbon dioxide gas is generated during the absorption process, especially in systems employing urease, and accumulates in the dialysate. Accordingly, sorbent-based dialysis regeneration systems typically must maintain large reservoirs of electrolytic solutions to regulate sodium concentration and maintain electrolyte concentration, and must also include a means for removing accumulated carbon dioxide gas, thus defeating the intended purpose of reducing total system volume and size.

Some systems have attempted to address the volume and weight problems by allowing for external connections to a tap water source in order to replenish system volume as needed. However, the introduction of tap water into a dialysis system necessitates additional purification measures, thus adding to system complexity and size. As a result, such systems may not be useful for mobile or portable use.

Sorbent-based dialysate regeneration systems can be found in U.S. Pat. No. 3,669,878 Marantz et al., which describes sorbent removal of urea and ammonium ions from spent dialysate via urease, ammonium carbonate, and zirconium phosphate; U.S. Pat. No. 3,669,880 Marantz et al., which describes directing a controlled volume of dialysate through zirconium phosphate, activated carbon, and hydrated zirconium oxide columns; U.S. Pat. No. 3,850,835 Marantz et al., which describes production of a zirconium hydrous oxide ion exchange media; and U.S. Pat. No. 3,989,622 Marantz et al., which describes adsorption of urease on aluminum oxide and magnesium silicate media to convert liquid urea to ammonium carbonate.

U.S. Pat. No. 4,581,141 Ash, describes removal of uremic substances from dialysate via a calcium-based cation exchanger, urease, and aliphatic carboxylic acid resin. U.S. Pat. No. 4,826,663 Alberti et al. describes a method of preparing a zirconium phosphate ion exchanger. U.S. Pat. No. 6,627,164 Wong describes production of sodium zirconium carbonate for ion exchange in renal dialysis, and U.S. Pat. No. 7,566,432 Wong describes production of zirconium phosphate particles for ion exchange in regenerative dialysis. U.S. Pat. No. 6,818,196 Wong, U.S. Pat. No. 7,736,507 Wong, U.S. Application Publication 2002/0112609 Wong, U.S. Application Publication 2010/0078387 Wong, and U.S. Application Publication 2010/00784330 Wong, describe cartridges for purification of dialysis solutions using sodium zirconium carbonate.

U.S. Pat. No. 6,878,283 Thompson, U.S. Pat. No. 7,776,210 Rosenbaum et al., U.S. Application Publication 2010/0326911 Rosenbaum et al., U.S. Application Publication 2010/0078381 Merchant, U.S. Application Publication 2009/0127193 Updyke et al. and U.S. Application Publication 2011/0017665 Updyke et al. describe filter cartridges having a plurality of types of filter media including zirconium compounds, urease, and alumina for dialysis systems. WO 2009/157877 A1 describes a urease material having urease immobilized on a substrate intermixed with a cation exchange material or zirconium phosphate material to improve workability for the reduction of clogging and to improve absorption of ammonium ions generated by the urease.

Management of impurities in regenerated dialysate can be found in U.S. Pat. No. 4,460,555 Thompson and U.S. Pat. No. 4,650,587 Polak et al., which describes magnesium phosphate media for removal of ammonia from aqueous solutions. U.S. Application Publication 2009/0282980 Gura et al. describes degassing devices for use in dialysate systems having urease media.

However, none of the dialysis systems known in the art and commercialized are mobile such that the weight and volume of the system is sufficiently appropriate to be used by a patient while ambulatory. Hence, there is a need for such devices, which can facilitate regular usage, but is also conducive to operation by a patient without the assistance of a medical professional. Accordingly, there remains a need for a patient-friendly wearable and/or portable dialysis system that is capable of operating on a small volume of dialysate and suitable for daily continuous or short-term dialysis.

SUMMARY OF THE INVENTION

The invention is directed to a hemodialysis system having a size and weight suitable to be carried or worn by a patient during a dialysis treatment. It is to be understood by one skilled in the art that hemodialysis can include hemodialysis, hemofiltration, and hemodiafiltration. In certain embodiments, a system for kidney replacement therapy has a sorbent cartridge for regenerating a dialysate or replacement fluid and a dialyzer or hemofilter for performing hemodialysis and/or hemofiltration wherein water, urea, NaCl, electrolytes, and waste substances are removed from the blood and water can also be removed from the blood during treatment. The dialyzer is incorporated in a housing having a blood inlet and a blood outlet, and a dialysate inlet and a dialysate outlet of the housing in fluid communication with the sorbent cartridge. The hemofilter is housed in a housing having a blood inlet and a blood outlet and an outlet for ultrafiltrate to exit the hemofilter.

In any embodiment, a system for performing kidney replacement therapy has a dialysis system having a controlled compliance dialysis circuit, a dialyzer having a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane. Blood is circulated through the dialyzer with an extracorporeal circuit having a conduit for receiving blood from a subject and a conduit for returning blood to a subject, a blood pump for conveying blood from the subject through the extracorporeal circuit and the dialyzer, wherein blood is conveyed from the subject, to the dialyzer and back to the subject. Dialysate is conveyed through the dialyzer with a dialysis circuit having a sorbent cartridge for removing impurities from the dialysate, one or more conduits for carrying dialysate between the sorbent cartridge and the dialyzer, and a dialysate pump for conveying dialysate from the sorbent cartridge, to the dialyzer and back to the sorbent cartridge, the sorbent cartridge having a dialysate input end and a dialysate output end. A control pump controls the bi-directional movement of fluid into and out of the dialysis circuit, where a flux of fluid moving between the extracorporeal circuit and the dialysis circuit is changed by the rate at which the control pump is operating, and a first control reservoir stores fluid removed from the dialysis circuit by the control pump or stores fluid that can be added to the dialysis circuit by the control pump. One or more controllers are provided with the system for controlling the rate of the dynamic control pump, a rate of the blood pump, and a rate of the dialysate pump. Optionally, a second control reservoir can store fluid such as tap water that can be added to the dialysis circuit by the control pump when the first control reservoir is used only for storing fluid from the dialysis circuit by the control pump.

In any embodiment, one or more of a blood pump and a dialysate pump are peristaltic pumps.

In any embodiment, the system has an infusate reservoir containing an infusate containing one or more electrolytes selected from potassium ions, calcium ions, and magnesium ions. The infusate is added to the dialysate under the control of a controller in order to maintain the concentration of potassium ion, calcium ion and/or magnesium ion within predetermined ranges.

In any embodiment, an infusate reservoir contains an infusate solution, the infusate solution comprising a potassium salt, and an infusate pump adds the solution to a dialysis circuit.

In any embodiment, an infusate container contains fresh water.

In any embodiment, an infusate container contains bicarbonate or a buffer.

In any embodiment, a conductivity meter measures the conductivity of dialysate in a dialysis circuit.

In any embodiment, a conductivity meter measures the conductivity of the dialysate at a position located between a dialysate outlet end of a sorbent cartridge and a dialysate inlet end of the dialyzer.

In any embodiment, the amount of conductive species entering and leaving a dialysis circuit is calculated by operation of a control pump and storing the value in a memory of a controller.

In any embodiment, one or more controllers calculate the amount of urea absorbed by the sorbent cartridge over a course of kidney replacement treatment.

In any embodiment, one or more controllers display the amount of urea absorbed by the sorbent cartridge to the subject or other individual.

In any embodiment, one or more controllers signal an alert if the difference between the conductivity measured by a first conductivity meter and a second conductivity meter are substantially equal.

In any embodiment, a system has a means for preventing the conveyance of dialysate to a dialyzer.

In any embodiment, one or more controllers calculate and store in a memory the amount of conductivity entering and leaving a dialysis circuit.

In any embodiment, one or more controllers calculate and store in a memory the amount of sodium ions entering and leaving a dialysis circuit by accounting for the amount of conductivity of an infusate solution entering the dialysis circuit.

In any embodiment, an anticoagulant container contains a solution comprising an anticoagulant, and an anticoagulant pump adds the anticoagulant solution to an extracorporeal circuit.

In any embodiment, an anticoagulant is heparin.

In any embodiment, heparin or another anticoagulant is covalently bond to a surface of an extracorporeal circuit.

In any embodiment, a volume of fluid added to a dialysis circuit by a control pump results in substantially the same volume of fluid transferred to the body of a subject. In any embodiment, a net volume of fluid removed from a dialysis circuit by a control pump results in substantially the same volume of fluid transferred from the body of a subject to a system for performing kidney replacement treatment.

In any embodiment, a dialysis circuit has a first pathway for conveying dialysate between a sorbent cartridge, a dialysate pump, and a dialyzer, and a second bypass pathway for conveying the dialysate between a dialysis outlet end of the sorbent cartridge and a dialysis inlet end of the sorbent cartridge without the dialysate passing through the dialyzer, and optionally one or more controllers direct the conveyance of the dialysate through the second bypass pathway when the conductivity of the dialysate is above a first predetermined level or below a second predetermined level, or optionally the one or more controllers direct the conveyance of the dialysate through the first pathway when the conductivity of the dialysate is within a predetermined range.

In any embodiment, a dialysate pump operates at a rate from about 10 to about 400 mL/min, at a rate from about 0 to about 200 mL/min, at a rate from about 0 to about 100 mL/min, or at a rate from about 0 to about 50 mL/min.

In any embodiment, a blood pump operates at a rate from about 50 to about 600 mL/min.

In any embodiment, one or more pressure meters measure the pressure of dialysate in a dialysis circuit, and one or more pressure meters measure the pressure of the blood entering a dialyzer at a blood inlet end and the pressure of the blood exiting the dialyzer at a blood outlet end.

In any embodiment, the total volume of dialysate within a dialysis circuit is less than about 1 L.

In any embodiment, a dialysis circuit has an air trap for removing air from the dialysate, the air trap located between a dialysate outlet end of a sorbent cartridge and a dialyzer, where optionally the air trap has a hydrophobic membrane for allowing air to pass through the membrane and blocking the movement of fluid across the membrane.

In any embodiment, a sorbent or a sorbent cartridge has or contains urease and zirconium phosphate.

In any embodiment, a sorbent or a sorbent cartridge has or contains a zirconium phosphate material intermixed with a urease-containing material.

In any embodiment, a sorbent or a sorbent cartridge has or contains zirconium oxide and activated carbon.

In any embodiment, a sorbent or a sorbent cartridge has or contains urease and magnesium phosphate.

In any embodiment, an impedance detector determines a tissue fluid volume in a subject, the impedance detector configured to send information to one or more controllers, and optionally the one or more controllers operates a control pump to maintain a ratio of tissue fluid volume to blood fluid volume in the range from about 5:1 to about 9:1.

In any embodiment, one or more controllers are configured to operate the control pump at a rate not exceeding the rate of a blood pump.

In any embodiment, a hematocrit sensor determines a hematocrit level of the blood in an extracorporeal circuit, the hematocrit sensor configured to send information to one or more controllers, wherein the hematocrit sensor can optionally be an oximeter, be a light source for emitting red or infrared light and a detector for detecting the emitted light, or be a monitor for measuring the velocity of ultrasonic sound waves in blood to indicate the level of protein concentration in the blood.

In any embodiment, a hematocrit sensor determines the fluid volume of blood in an extracorporeal circuit and optionally determines the fluid volume of the blood at a position to the blood entering a dialyzer.

In any embodiment, a dialysis membrane has high permeability.

In any embodiment, the dialysate is conveyed through the dialysis system by a dialysate pump, where the rate of the dialysate pump is controlled by a controller.

In any embodiment, blood from a patient is conveyed through the dialysis system by a blood pump, wherein the blood pump is controlled by a controller.

In any embodiment, the pressure of blood entering the dialyzer forming part of the dialysis system is measured entering the dialyzer by a pressure meter and/or the pressure of the blood exiting the dialyzer is measured by a pressure meter.

In any embodiment, the pressure of the dialysate entering the dialyzer forming part of the dialysis system is measured entering the dialyzer by a pressure meter and/or the pressure of the dialysate exiting the dialyzer is measured by a pressure meter.

In any embodiment, operation of a control pump in an influx direction removes protein present on a surface of a dialysis membrane of a dialyzer.

In any embodiment, the dialysis circuit comprises a first pathway for conveying the dialysate between the sorbent cartridge, the dialysate pump, and the dialyzer, and a second bypass pathway for conveying the dialysate between the dialysis output end of the sorbent cartridge and the dialysis input end of the sorbent cartridge without the dialysate passing through the dialyzer. A controller controls the conveyance of the dialysate through either the first pathway or the second bypass pathway based at least in part upon the conductivity of the dialysate.

In any embodiment, the hemodialysis system has a bicarbonate container containing a solution having a bicarbonate salt and a bicarbonate pump for adding the bicarbonate solution to the dialysis circuit. The bicarbonate is added to the dialysate under the control of a controller in order to maintain the concentration of bicarbonate ion within predetermined ranges.

In any embodiment, a volume of the dialysis circuit is larger than the volume of the extracorporeal circuit.

In any embodiment, a system for kidney replacement therapy is primed by attaching a container containing a priming fluid to the system, the system having an extracorporeal circuit having a first end that draws the priming fluid from the container and a second end that allows priming fluid to exit the extracorporeal circuit; and a dialysis circuit, the extracorporeal circuit and the dialysis circuit in fluid communication through a dialysis membrane. A blood pump is operated to convey the priming fluid from the container and through the extracorporeal circuit to fill the extracorporeal circuit with the priming fluid. The first and second ends of the extracorporeal circuit are attached to the cardiovascular system of a subject and dialysate pump is operated to draw the priming fluid across the dialysis membrane from the extracorporeal circuit into the dialysis circuit and to draw blood from the subject into the extracorporeal circuit such that the blood reaches an inlet of a dialyzer housing the dialysis membrane; and after the blood reaches the inlet, the blood pump, ultrafiltrate pump, and the dialysate pump are operated where the ultrafiltrate pump is operated at a rate sufficient to transfer the volume of priming fluid present in the extracorporeal circuit into the dialysis circuit through the dialysis membrane. When the extracorporeal circuit is filled with blood from the subject, the ultrafiltrate pump is operated at a rate sufficient to draw fluid from the blood into the dialysis circuit to complete filling the dialysis circuit with fluid.

In any embodiment, a system for kidney replacement therapy is primed by attaching a container containing a priming fluid to the system, the system having an extracorporeal circuit having a first end that draws the priming fluid from the container and a second end that allows priming fluid to exit the extracorporeal circuit; and a dialysis circuit, the extracorporeal circuit and the dialysis circuit in fluid communication through a dialysis membrane. A blood pump is operated to convey the priming fluid from the container and through the extracorporeal circuit to fill the extracorporeal circuit with the priming fluid. The first and second ends of the extracorporeal circuit are attached to the cardiovascular system of a subject and the dialysate pump is operated to draw the priming fluid across the dialysis membrane from the extracorporeal circuit into the dialysis circuit and to draw blood from the subject into the extracorporeal circuit such that the blood reaches an inlet of a dialyzer housing the dialysis membrane; and after the blood reaches the inlet of a dialyzer housing, the blood pump and the dialysate pump are operated, where the dialysate pump is operated at a lower rate than the blood pump rate to transfer the volume of priming fluid present in the extracorporeal circuit into the dialysis circuit through the dialysis membrane. When the extracorporeal circuit is filled with blood from the subject, the dialysate pump is operated at a rate lower than the blood pump to draw fluid from the blood into the dialysis circuit to complete filling the dialysis circuit with fluid.

In an embodiment, a system for kidney replacement therapy is primed by attaching a container containing a priming fluid to the system, the system having an extracorporeal circuit having a first end that draws the priming fluid from the container and a second end that discharges the priming fluid from the extracorporeal circuit, where the extracorporeal circuit is in fluid communication with a dialysis circuit through a dialysis membrane. A blood pump is operated to convey the priming fluid from the container and through the extracorporeal circuit to fill the extracorporeal circuit with the priming fluid, and a dialysate pump is operated to draw the priming fluid across the dialysis membrane from the extracorporeal circuit into the dialysis circuit until the dialysis circuit is filled with the priming solution. Air is vented from the dialysis circuit to allow the priming fluid to enter the dialysis circuit.

In any embodiment of priming a system, a lower rate of a dialysis pump is about 66% or less than the rate of a blood pump or is about 60% or less than the rate of a blood pump.

In any embodiment of priming a system, a priming fluid is a saline solution.

In any embodiment of priming a system, the system is primed without introducing any priming fluid to a subject.

In any embodiment of priming a system, one or more of potassium ion, calcium ions, magnesium ions and bicarbonate ions is added to the priming fluid to convert the priming fluid in the dialysis circuit to a physiologically compatible dialysate.

In any embodiment, one or more controllers calculate the volume of fluid transferred from blood of a subject to a dialysis circuit and stores the value of the volume in memory selected from one or more of RAM, Dynamic RAM, microprocessor cache, FLASH memory and memory card.

In any embodiment, a blood pump pumps fluids through a dialyzer in a first direction and a dialysate pump pumps fluids through the dialyzer in a second direction opposite to the first direction.

In any embodiment, a blood pump and a dialysate pump are independently selected from the group consisting of peristaltic pumps, diaphragm pumps, centrifugal pumps and shuttle pumps.

In an embodiment, a system for kidney replacement therapy performs enhanced convective clearance with reduced risk of blood clotting. The vasculature of a subject is attached to a system for kidney replacement therapy having an extracorporeal circuit having a first end that draws blood from the subject and a second end that returns blood to the subject, the extracorporeal circuit and the dialysis circuit in fluid communication through a dialysis membrane housed in a dialyzer. Blood is conveyed from the subject through the extracorporeal circuit and the dialyzer and then returned to the subject. A dialysate is conveyed through the dialysis circuit such that the dialysate moves from a sorbent cartridge, to the dialyzer and back to the sorbent cartridge, where at least one waste species diffuses from the blood to the dialysate through the dialysis membrane and the sorbent cartridge substantially removes at least one impurity or waste species from the dialysate. A control pump, which adds fluid from a control reservoir to the dialysis circuit in an influx direction via a conduit or removes fluid from the dialysis circuit to the control reservoir in an efflux direction via the conduit, is operated to intermittently switch the control pump between the efflux direction to move fluid across the dialysis membrane from the extracorporeal circuit to the dialysis circuit and the influx direction to move fluid across the dialysis membrane from the dialysis circuit to the extracorporeal circuit. The intermittent switching of the control pump accomplishes the convective clearance of at least one waste species.

In any embodiment, a waste species has a molecular weight less than albumin, about 66000 g/mol.

In any embodiment, a species removed by a sorbent cartridge is urea.

In any embodiment, a control pump is intermittently switched between the efflux direction and the influx direction at least once every minute.

In any embodiment, a control pump is intermittently switched between an efflux direction and an influx direction such that the pump is not operated continuously in either the efflux or the influx direct for a time period exceeding about 45 seconds.

In any embodiment, a control pump is intermittently switched between an efflux direction and an influx direction such that the pump is not operated continuously in either the efflux or the influx direct for a time period exceeding about 30 seconds.

In any embodiment, a control pump is intermittently switched between an efflux direction and an influx direction such that the pump is not operated continuously in either the efflux or the influx direct for a time period exceeding about 15 seconds.

In any embodiment, a control pump does not operate in an efflux direction and an influx direction for equal period of times.

In any embodiment, a control pump does not operate to pump an equal volume in an efflux direction and an influx direction over a period of time.

In any embodiment, a control pump operates to pump a larger volume in an efflux direction compared with an influx direction over a period of time.

In any embodiment, a control pump operates to pump a volume in an efflux direction that is at least about 10% greater compared to a volume pumped in an influx direction over a period of time.

In any embodiment, a control pump operates to pump a volume in an efflux direction that is at least about 20% greater compared to a volume pumped in an influx direction over a period of time.

In any embodiment, a control pump operates to pump a volume in an efflux direction that is at least about 30% greater compared to a volume pumped in an influx direction over a period of time.

In any embodiment, a control pump is operated in a manner to cause the net removal of about 100 to about 1000 mL of fluid from the subject per hour of treatment.

In any embodiment, a control pump is operated in a manner such that the net removal of fluid from the subject does not exceed about 30% of Qp, where Qp=Blood Flow Rate×(1-hematocrit).

In any embodiment, the volume of fluid entering or leaving a subject during a period of time is calculated by a controller and optionally stored in a memory of the controller, and wherein the volume of fluid pumped by the control pump and the volume of fluid pumped by the infusate pump is considered in calculating the volume of fluid entering or leaving the subject.

In an embodiment, a system for kidney replacement therapy is operated by attaching the vasculature of a subject to a system for kidney replacement therapy having an extracorporeal circuit having a first end that draws blood from the subject and a second end that returns blood to the subject, and a controlled compliance dialysis circuit, the extracorporeal circuit and the dialysis circuit in fluid communication through a dialysis membrane housed in a dialyzer. Blood is conveyed from the subject through the extracorporeal circuit and the dialyzer and returned to the subject. A dialysate is conveyed through the dialysis circuit such that the dialysate moves from a sorbent cartridge, to the dialyzer and back to the sorbent cartridge, where at least one waste species diffuses from the blood to the dialysate through the dialysis membrane and the sorbent cartridge substantially removes at least one impurity or waste species from the dialysate. A control pump, which adds fluid from a control reservoir to the dialysis circuit in an influx direction via a conduit or removes fluid from the dialysis circuit to the control reservoir in an efflux direction via the conduit, is operated to intermittently switch the control pump between the efflux direction to move fluid across the dialysis membrane from the extracorporeal circuit to the dialysis circuit and the influx direction to move fluid across the dialysis membrane from the dialysis circuit to the extracorporeal circuit. A volume of fluid added to the dialysis circuit by the control pump results in substantially the same volume of fluid transferred to the body of the subject, and a volume of fluid removed from the dialysis circuit by the control pump results in substantially the same volume of fluid transferred from the body of the subject to the system for performing kidney replacement treatment.

In any embodiment, a system for kidney replacement therapy to quantify urea removal is operated by attaching the vasculature of a subject to a system for kidney replacement therapy having an extracorporeal circuit having a first end that draws blood from the subject and a second end that returns blood to the subject, and a dialysis circuit, where the extracorporeal circuit and the dialysis circuit are in fluid communication through a dialysis membrane housed in a dialyzer. Blood is conveyed from the subject through the extracorporeal circuit and the dialyzer and returning the blood to the subject. Dialysate is conveyed through the dialysis circuit such that the dialysate moves from a sorbent cartridge, to the dialyzer and back to the sorbent cartridge, where urea diffuses from the blood to the dialysate through the dialysis membrane. The conductivity of the dialysate is monitored at an inlet end of the sorbent cartridge and at an outlet end of the sorbent cartridge. The amount of urea absorbed by the sorbent cartridge is calculated based at least in part upon the conductivity measured at the inlet end of the sorbent cartridge and at the outlet end of the sorbent cartridge.

In any embodiment, a system for kidney replacement therapy to quantify urea removal has a dialyzer with a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane. An extracorporeal circuit has a conduit for receiving blood from a subject and a conduit for returning blood to a subject and a blood pump for conveying blood from the subject, to the dialyzer and back to the subject. A dialysis circuit has a sorbent cartridge for removing urea from the dialysate, one or more conduits for carrying dialysate between the sorbent cartridge and the dialyzer, and a dialysate pump for conveying dialysate from the sorbent cartridge, to the dialyzer and back to the sorbent cartridge, the sorbent cartridge having a dialysate input end and a dialysate output end. A first conductivity meter is present for measuring the conductivity of the dialysate at the dialysate input end of the sorbent cartridge. A second conductivity meter is present for measuring the conductivity of the dialysate at the dialysate output end of the sorbent cartridge. One or more controllers compare the conductivity measured by the first conductivity meter and the second conductivity meter and calculate the amount of urea absorbed by the sorbent cartridge.

In any embodiment, the amount of urea absorbed by a sorbent cartridge is communicated to the subject or other individual.

In any embodiment, the system has a relative blood volume monitor for monitoring changes in the relative blood volume hydration status of the subject's blood over the course of treatment.

In any embodiment, a system for performing kidney replacement therapy has a dialysis system having a controlled compliance dialysis circuit, a dialyzer having a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane. Blood is circulated through the dialyzer with an extracorporeal circuit having a conduit for receiving blood from a subject and a conduit for returning blood to a subject, a blood pump for conveying blood from the subject through the extracorporeal circuit and the dialyzer, wherein blood is conveyed from the subject, to the dialyzer and back to the subject. Dialysate is conveyed through the dialyzer with a dialysis circuit having a sorbent cartridge for removing impurities from the dialysate, one or more conduits for carrying dialysate between the sorbent cartridge and the dialyzer, and a dialysate pump for conveying dialysate from the sorbent cartridge, to the dialyzer and back to the sorbent cartridge, the sorbent cartridge having a dialysate input end and a dialysate output end. A control pump moves fluid between the dialysis circuit and the extracorporeal circuit by removing fluid from the dialysis circuit, where a flux of fluid moving between the extracorporeal circuit and the dialysis circuit is changed by the rate at which the control pump is operating, and a first control reservoir stores fluid removed from the dialysis circuit by the control pump. A second reservoir and a second reservoir pump is present to add water to the dialysis circuit, where fluid added to the dialysis circuit causes movement of fluid from the dialysis circuit to the extracorporeal circuit. In any embodiment, the second reservoir can store water, tap water or purified water. One or more controllers are provided with the system for controlling a rate of the control pump, a rate of the blood pump, a rate of the second reservoir pump and a rate of the dialysate pump. This second reservoir can be located either before the dialysate pump, after the dialysate pump or after the sorbent cartridge.

In any embodiment, a control pump operates in a bidirectional fashion to move fluid between the dialysis circuit and the extracorporeal circuit.

In any embodiment, a second reservoir contains water, tap water or purified water.

In any embodiment, a system for performing kidney replacement treatment has a hemofiltration system having a controlled compliance filtration circuit, a hemofilter with a hemofiltration membrane, a blood inlet end for receiving blood, a blood outlet end for allowing blood out of the hemofilter, and an ultrafiltration outlet for allowing an ultrafiltrate out of the hemofilter. An extracorporeal circuit has a conduit for receiving blood from a subject and a conduit for returning blood to the subject, and a blood pump for conveying blood from the subject, to the hemofilter and back to the subject. A hemofiltration circuit has a sorbent cartridge for removing at least one impurity or waste species from the ultrafiltrate to generate a replacement fluid, wherein the ultrafiltrate enters an inlet end of the sorbent cartridge and a replacement fluid exits an outlet end of the sorbent cartridge, the hemofiltration circuit having one or more conduits and a filtrate pump for conveying the ultrafiltrate from the hemofilter to the sorbent cartridge and for infusing the replacement solution into the extracorporeal circuit, where one or more controllers control a rate of the blood pump and a rate of the filtrate pump.

In any embodiment, a rate of conveyance of the replacement solution is substantially equal to the rate of operation of the filtrate pump.

In any embodiment, a rate of conveyance of the replacement solution is substantially equal to the rate of operation of the filtrate pump within about 5 mL/min.

In any embodiment, a control pump removes a portion of ultrafiltrate from a hemofiltration circuit, where the removed portion of the ultrafiltrate is not generated into a replacement fluid and infused into an extracorporeal circuit.

In any embodiment, replacement kidney therapy is performed by hemofiltration including attaching the vasculature of a subject to a system for kidney replacement therapy having an extracorporeal circuit having a first end that draws blood from the subject and a second end that returns blood to the subject. Blood is conveyed from the subject through the extracorporeal circuit and the blood returned to the subject via a blood pump, where the blood passes through a hemofilter having a hemofiltration membrane, the hemofilter attached to a controlled compliant hemofiltration circuit. A filtrate pump is operated that draws an ultrafiltrate from the blood in the hemofilter and passes the ultrafiltrate through a sorbent cartridge to remove one or more waste species or impurities from the ultrafiltrate to generate a replacement fluid; and infusing the replacement fluid into the extracorporeal circuit.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 3A shows a sorbent cartridge having multiple sorbent materials in a single housing. FIG. 3B shows a schematic for a sorbent cartridge having sorbent materials housed in several housings. FIG. 3C shows a side view of an individual housing from the sorbent cartridge depicted in FIG. 3B. FIG. 3D shows a top view of an individual housing from the sorbent cartridge depicted in FIG. 3B and a top view of a spacer frit. FIG. 3E shows a bottom view of an individual housing from the sorbent cartridge depicted in FIG. 3B and a bottom view of a spacer frit.

FIG. 4A shows a top view of a carrier for sorbent housings. FIG. 4B shows a top view of the carrier of FIG. 4A with several sorbent housings placed within the carrier. FIG. 4C shows a side view of a sorbent cartridge having five separate sorbent housings.

DETAILED DESCRIPTION OF THE INVENTION

Figure 1A:
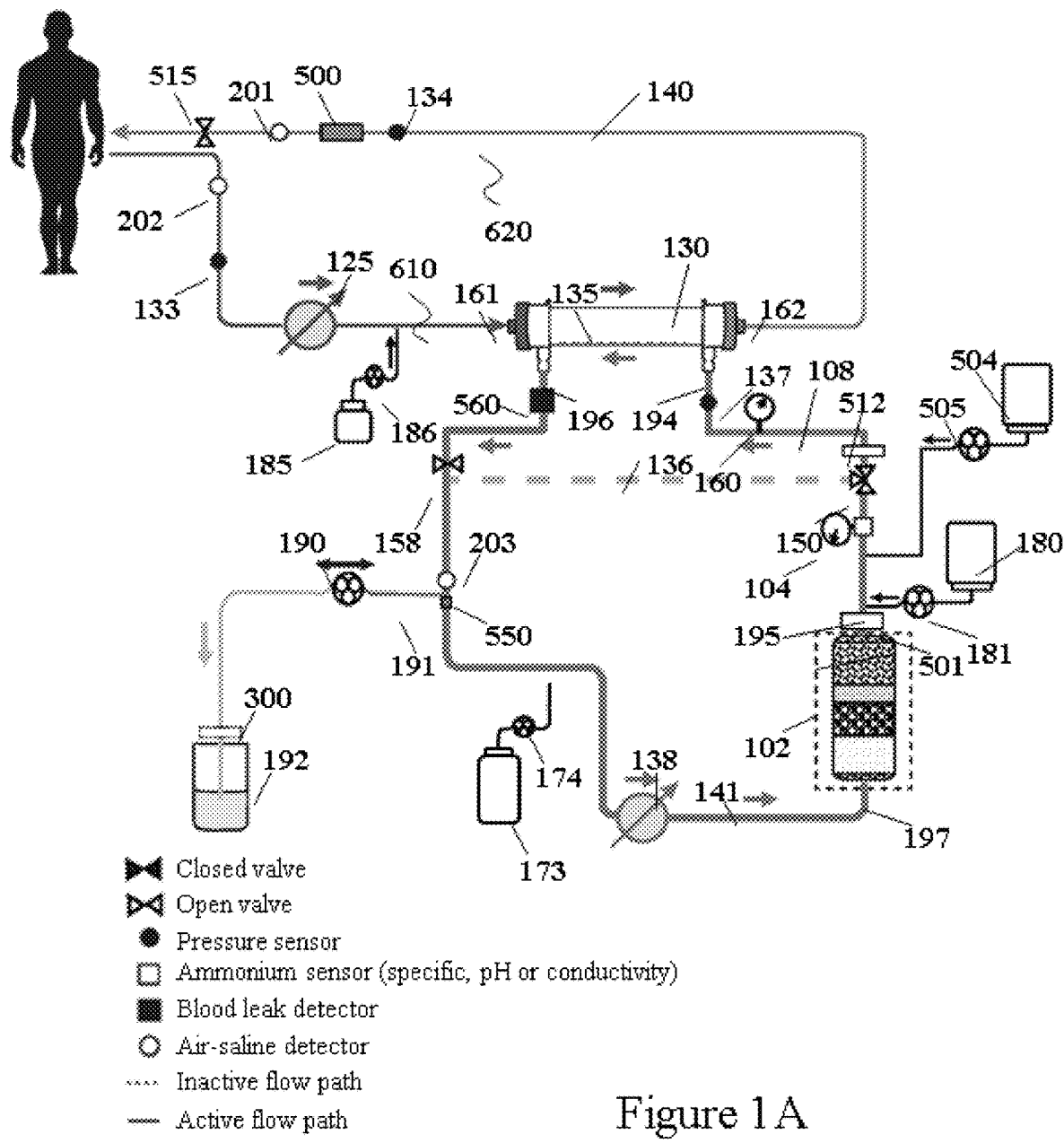
FIG. 1A shows a hemodialysis device having a controlled compliant dialysis circuit operating in accordance with certain embodiments.

Dialysis is the most commonly applied physical principle to address the build-up of urea and other toxins, to balance electrolytes, and to remove excess fluid in patients with kidney failure. Dialysis as a renal or kidney replacement therapy can include hemodialysis, hemodiafiltration, or hemofiltration to remove toxins and impurities from a patient's blood. Dialysis membranes employed in dialysis treatment are typically only selective toward molecular weight and not toward other properties such as electrical charge. As such, urea, ions and other small molecules can move across the dialysis membrane unimpeded from a higher concentration to a lower concentration via diffusion thereby lowering the concentration of such species in the patient's blood through the process of hemodialysis.

Hemofiltration and hemodiafiltration employ techniques involving removing fluid from the patient by drawing bulk fluid across the dialysis membrane thereby pulling out waste products with a solute drag effect. Further, both hemofiltration and hemodiafiltration can be employed for ultrafiltration to accomplish the removal of accumulated fluid from a subject. Hemofiltration and hemodiafiltration are more effective for removing mid-weight and other impurities that otherwise have a low coefficient of diffusion and cannot be efficiently removed by hemodialysis.

During operation of typical dialysis machines to perform hemodiafiltration, blood is passed through a dialysis chamber on one side of a dialysis membrane and a dialysate is passed on the other side of the dialysis membrane. In addition to diffusion of solutes across the dialysis membrane, a difference in pressure between the blood-side and the dialysate-side of the dialysis membrane drives the bulk movement of water from higher pressure to lower pressure. This flow is in excess to the patient's net fluid removal requirements, so the blood must be rehydrated with a sterile substitution or replacement solution. The pressure generated on a particular side of the dialysis membrane depends on several factors including flow rate, viscosity of the fluid, geometry of the dialyzer and the physiological condition of the patient. Pressure and the subsequent net movement of water across the dialysis membrane requires large and expensive equipment to control with a high degree of accuracy.

A system or apparatus for kidney replacement therapy can also be configured to perform hemofiltration. Blood is passed through a hemofilter having a hemofiltration membrane to contact one side of the hemofiltration membrane. A negative pressure is applied to the side of the hemofiltration membrane not in contact with the blood to draw the movement of water from the blood across the hemofiltration membrane. The amount or volume of water transversing the hemofiltration membrane also depends on several factors including the blood flow rate, viscosity, geometry of the hemofilter and the physiological condition of the patient. Removal of impurities from the blood by convection during hemofiltration is usually only accomplished by the removal of a large volume of fluid from the blood. Substitution or replacement fluid needs to be introduced to the subject. Expensive equipment is normally required to balance fluid removal with replacement or substitution fluid.

A portable dialysis system is contemplated herein having a controlled compliance dialysis circuit. In general, portable dialysis systems rely upon the regeneration of spent dialysate (i.e. dialysate having urea and/or other waste species therein) to form refreshed dialysate that can be reused to perform dialysis or to dialyze the patient utilizing a smaller dialysate volume. Regeneration of the dialysate allows for the volume of fluid that needs to be supplied to perform a session of dialysis treatment to be limited and enable a portable system. The systems of the invention can employ a reservoir of working dialysate solution that varies in volume depending upon bulk movement of water across the dialysis membrane and/or water added to dilute sodium ion concentration and reduce conductivity. Further, a system for kidney replacement therapy employing hemofiltration is contemplated wherein ultrafiltrate is treated to generate a replacement solution for reintroduction to the subject. Use of the ultrafiltrate to generate a replacement solution simplifies the balancing of fluid removal with the replacement solution; specifically, scales or gravimetric methods are not required to balance fluid removal with fluid replacement. Systems where the volume of working dialysate and/or ultrafiltrate vary during the course of treatment complicate accurate control over removal of fluid from a patient through techniques such as ultrafiltration and hemodiafiltration. In the present invention, a controlled compliance dialysis circuit is provided for conveying and re-circulating a dialysate between a dialyzer, where the dialysate picks up impurities such as urea, and a sorbent cartridge where waste species are removed from the dialysate to form refreshed dialysate after the addition of cation electrolytes. The dialysate flow path described herein has active control of fluid flow entering and exiting the flow path in a manner that allows for the accurate performance of ultrafiltration, the quantization of urea removal and the performance of conductive clearance of mid-weight uremic impurities without an excessive risk for blood clotting.

Alternatively, a controlled compliance hemofiltration circuit is provided for conveying an ultrafiltrate from a hemofilter to a sorbent cartridge where waste species are removed from the ultrafiltrate. The ultrafiltrate with the impurities removed can then be reintroduced to the subject as a replacement fluid. The controlled compliance hemofiltration circuit provides for the accurate control of fluid removal and introduction of replacement fluid to the subject without the use of scales or gravimetric methods. The controlled compliance dialysis circuit described herein controls the inputs and outputs of fluid to the dialysis circuit by using a flow path having a substantially inflexible volume wherein all of the complexity associated with scale control is eliminated. Fluid balancing is accomplished very accurately. In any embodiment described herein, an operator or user need only set the fluid removal rate and the device can control the fluid removal accurately without the use of scales or balancing chambers to control flow.

Definitions

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "activated carbon" refers to a porous carbon material having a surface area greater than 500 $m^2$ per gram. Activated carbon can be capable of absorbing several species including heavy metals such as lead, mercury, arsenic, cadmium, chromium and thallium among others, oxidants such as chlorine and chloramine, fluoride ions, and waste species such as phosphate and certain nitrogen-containing waste species such as creatinine and uric acid The terms "administering," "administer," "delivering," "deliver," "introducing," "bolus," and "introduce" can be used interchangeably to indicate the introduction of water or an agent into the body of a patient, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane or other means.

The term "air trap" refers to a structure for separating a gas from a mixture of a gas and a liquid or any other separation means known in the art. An air trap can include a hydrophobic membrane for allowing gases to pass and for preventing the passage of water.

The term "anticoagulant" is a substance that prevents or delays the clotting of blood, such as heparin, fragmin, and sodium citrate.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "conduit" refers to a vessel or passageway having a void volume through which a fluid can travel or move. A conduit can have a dimension parallel to the direction of travel of the fluid that is significantly longer than a dimension orthogonal to the direction of travel of the fluid.

"Chronic kidney disease" (CKD) is a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "conductivity meter" or "conductivity sensor" refers to a device for measuring the electrical conductance of a solution.

The term "consisting of" includes and is limited to whatever follows the phrase "consisting of:" Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "control pump" refers to a pump that is operable to pump fluid bi-directionally to actively control the transfer of fluid volume into or out of a compartment or circuit.

The term "control reservoir" refers to a substantially inflexible, or non-flexible vessel or container accessible by the control pump that contains a variable amount of fluid.

A "control system" consists of combinations of components that act together to maintain a system to a desired set of performance specifications. The control system can use processors, memory and computer components configured to interoperate to maintain the desired performance specifications. It can also include fluid control components, and solute control components as known within the art to maintain the performance specifications.

A "controller," "control unit," "processor," or "microprocessor" is a device which monitors and affects the operational conditions of a given system. The operational conditions are typically referred to as output variables of the system, which can be affected by adjusting certain input variables.

The terms "controlled compliance" and "controlled compliant" describe the ability to actively control the transfer of fluid volume into or out of a compartment or circuit. In certain embodiments, the variable volume of fluid in a dialysate circuit expands and contracts via the control of one or more pumps. The volume of fluid in the system minus the attached reservoirs once the system is in operation is generally constant. The attached reservoirs allow the system to adjust the patient fluid volume by withdrawing fluid and storing the desired amount in an attached control reservoir and/or by providing rebalanced fluids to the patient and removing waste products. Alternatively, the fluid stored in a control reservoir attached to the dialysate circuit can be used for ultrafiltration (UF) and/or delivery of an infusate. The terms "controlled compliance" and "controlled compliant" are not to be confused with the term "non-compliant volume," which simply refers to a vessel, conduit, container, pathway or cartridge that resists the introduction of a volume of fluid after air has been removed from a defined space such as a vessel, conduit, container, pathway or cartridge.

The term "convective clearance" refers to the movement of solute molecules or ions across a semi-permeable barrier due to force created by solvent molecules moving across the semi-permeable barrier.

The term "dialysate" describes a fluid into which solutes from a fluid to be dialyzed diffuse through a membrane. A dialysate typically contains electrolytes that are close in concentration to the physiological concentration of electrolytes found in blood.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "dialysis membrane" or "hemofiltration membrane" can refer to a semi-permeable barrier selective to allow diffusion of solutes of a specific range of molecular weights through the barrier, or optionally a high permeability membrane, which is a type of semipermeable membrane that is more permeable to water than the semipermeable membrane of a conventional hemodialysis system, which has a semipermeable membrane that has a sufficiently low permeability to water such that an ultrafiltration controller is not required to prevent excessive loss of water from the patient's blood. During high permeability hemodialysis, the system removes toxins or excess fluid from the patient's blood using the principles of convection (via a high ultrafiltration rate) and/or diffusion (via a concentration gradient in dialysate). In certain non-limiting examples, the semipermeable membrane during high permeability hemodialysis or hemofiltration has an in vitro ultrafiltration coefficient (Kuf) greater than 8 milliliters per hour per conventional millimeter of mercury, as measured with bovine or expired human blood.

The term "diluent" refers to a fluid having conductivity less than a fluid to which the diluent is added.

The term "electrolyte" refers to an alkali or alkali earth cation dissolved in an aqueous medium.

The term "filtration" refers to a process of separating solutes from a fluid, by passing the fluid through a filter medium across which certain solutes or suspensions cannot pass. Filtration is driven by the pressure difference across the membrane.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Those skilled in the art will recognize that a minimal amount of expansion or contraction of the vessel or container can occur in a substantially inflexible volume; however, the addition or subtraction of a significant volume of fluid over a maximum or minimum will be resisted.

The term "fluid communication" refers to at least two fluids that are contained in separated compartments that are able to exchange matter, either solvent or solute molecules or ions, through a semi-permeable barrier.

The terms "frit" and "spacer frit" refer to a material that is biocompatible and has a porosity between about 1 μm and 300 μm. The material can be one or more of biocompatible, compressible, an open cell polymer or foam or similar material.

"Hemofiltration" is a therapy in which blood is filtered across a semi-permeable membrane. Water and solutes are removed from the blood via pressure-driven convection across the membrane. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. The dialysate employed during hemodialysis has soluble ions such as sodium, calcium and potassium ions and is not pure water. The sieving properties of the membrane exclude all solutes above a certain threshold from crossing the membrane. One common sieving property is "albumin sieving." In most situations it is not desirable to remove Albumin during renal replacement therapy, as lower blood serum Albumin is associated with increased mortality rates.

The term "albumin sieving coefficient" can be used to describe the amount of albumin that will cross a membrane.

The term "hematocrit" refers to the fraction of blood volume occupied by erythrocytes.

"Hemodiafiltration" is a therapy that combines hemofiltration and hemodialysis.

The term "impedance meter" refers to a device for measuring the opposition of an object or structure to an alternating current.

The term "impurity species" refers to a molecular or ionic species that originates from tap water, a sorbent cartridge or a source other than a patient's or subject's blood including chlorine, fluoride ions, and aluminum-containing species.

The term "infusate container" refers to a vessel, which can be substantially inflexible or non-flexible for holding a solution of one or more salts for the adjustment of the composition of a dialysate.

The term "infusate solution" refers to a solution of one or more salts for the adjustment of the composition of a dialysate, such as salts of calcium, magnesium and potassium.

The term "waste species" or "waste products" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system. For example, nitrogen-containing waste products are generally at a level less than 30 mg/dL in the blood for individuals with a healthy renal system and inorganic phosphate can be generally in a range between 2.5-4.5 mg/dL but not necessarily limited to this range. The level of waste products in the blood is elevated for individuals with impaired kidney function.

The term "nitrogenous waste" refers to any non-polymeric nitrogen-containing organic compound originating from the blood of a patient. Nitrogenous waste includes urea and creatinine.

The term "oximeter" refers to a device for measuring the amount of oxygen carried by a volume of blood.

The term "luer connector" or "luer adapter" refers to adapters or connectors conforming with International Standards Organization (ISO) standards 594-2.

The term "memory" refers to a device for recording digital information that can be accessed by a microprocessor, such as RAM, Dynamic RAM, microprocessor cache, FLASH memory, or memory card.

The term "mid-weight uremic wastes" refers to substances that can pass through a dialysis membrane that have a molecular weight less than about 66,000 g/mol and greater than about 1000 g/mol.

The term "moving fluid bi-directionally" refers to the ability to move a fluid across a barrier, such as a semi-permeable membrane, in either direction.

"Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

A "patient" or "subject" is a member of any animal species, preferably a mammalian species, optionally a human. The subject can be an apparently healthy individual, an individual suffering from a disease, or an individual being treated for a disease.

The terms "pathway" and "conveyance pathway" refer to the route through which a fluid, such as dialysate or blood travels.

The term "peristaltic pump" refers to a pump that operates by compression of a flexible conduit or tube through which the fluid to be pumped passes.

The terms "portable system" or "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The terms "pressure differential" and "pressure drop" refer to the difference in pressure measurements of a fluid between two points of measurement.

The term "pressure meter" refers to a device for measuring the pressure of a gas or liquid in a vessel or container.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pulsatile pump" refers to a pump that mimics the action of a mammalian heart where the pumped fluid undergoes periodic variation in velocity.

The term "pump" refers to any device that causes the movement of fluids or gases by the application of suction or pressure.

The term "quick connector" refers to any structure for making an attachment that is operable by an individual using their hands or fingers without the assistance of additional tools. The quick connector may have a valve that shuts off flow when the connector is disconnected.

The term "relative blood volume monitor" refers to any device measuring the concentration of any solute or solid material in the blood. Non-limiting examples of relative blood volume monitors include devices for measuring the concentration of oxyhemoglobin, deoxyhemoglobin, hematocrit or red blood cell count, osmolarity or total protein concentration of the blood.

The term "relative blood volume hydration status" refers to the relative change in the level of any target solute or solid material in the blood over a period of time. Non-limiting examples of target solute or solid materials include oxyhemoglobin, deoxyhemoglobin, hematocrit or red blood cell count, osmolarity or total protein concentration of the blood. Relative blood volume hydration status can be monitored by observation of a change in a signal responsive to the level of any target solute or solid material in the blood without a requirement that the absolute concentration of the target solute or solid material be determined.

The term "spent dialysate" refers to a dialysate that has been contacted with blood through a dialysis membrane and contains one or more impurity, or waste species, or waste substance, such as urea.

The term "sorbent cartridge" refers to a cartridge containing one or more sorbent materials for removing specific solutes from solution, such as urea.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, hemodiafiltration, or filtration process.

The term "void volume" refers to a specific volume that can be occupied by a fluid in a defined space such as a dialysate circuit of the invention including all components contained therein.

"Diffusive permeability" is a property of a membrane describing permeation by diffusion. Diffusion is the process of solutes moving from an area of higher concentration to an area of lower concentration The term "porosity," as used herein describes the fraction of open pore volume of a membrane.

The term "shunt," as used herein describes a passage between channels, such as blood vessels, where the shunt diverts or permits flow from one pathway or region to another.

The term "plumbing," as used herein generally describes any system of valves, conduits, channels, and lines for supplying any of the fluids used in the invention.

The term "extracorporeal," as used herein means situated or occurring outside the body.

The term "effluent dialysate," as used herein describes the discharge or outflow after the dialysate has been used for dialysis.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "working dialysate solution" refers to a dialysate solution that is undergoing active circulation or movement through a system including conduits, pathways, dialyzers and cartridges.

Controlled Compliance Dialysis Circuit and Portable Dialysis System

In the controlled compliance dialysis circuit disclosed herein, passive movement of fluid across the dialysis membrane due to operational pressure change is eliminated. The invention provides for the ability to accurately control net patient fluid status, and/or diffusion combined with increased clearance via convection, and/or active provisioning of extra fluid to a patient. The invention can actively provide fluid to the patient when the patient becomes hypotensive or hypovolemic, and replace a blood circuit with a physiological solution when a patient is taken off a system. The invention can also provide for adjusting convective clearance. Any combination of the above mentioned features is contemplated by the invention. The system allows for the return of blood from the system back to the patient without necessarily providing for additional fluids. The system can optionally account for an infusate volume, provide additional convective clearance, and/or provide control of the entire process. In contrast, non-expandable volume systems do not allow for ultrafiltration (UF), the ability to give fluid to the patient, convective clearance or return of blood to the patient without additional fluids. Instead of a fixed or non-compliant volume used in known systems, the present invention can intentionally change a volume to push fluid to or from the patient where the system controls volume and compliance (both of which are dynamic and changing) to achieve the desired goals of a therapy. The controlled compliance dialysis circuit also simplifies the entire system. Specifically, scales or gravimetric methods are not required to balance fluid removal with fluid replacement.

In certain embodiments, the controlled compliance dialysis circuit has two points where fluid can enter the dialysate flow path: 1) infusate pumps and 2) a control pump that controls the movement of fluid across the dialysis membrane. The controlled compliance dialysis circuit operates by employing two principle components: 1) an extracorporeal circuit that is attached to the vasculature and the circulation of a patient, and 2) a dialysis circuit having a limited void volume for the circulation of a dialysate. The extracorporeal circuit is an extension of the patient's circulatory system external to the patient's body. Any fluid added to the dialysate circuit can enter the patient's body; likewise, any fluid drawn out of the extracorporeal circuit can originate from the patient's body. Due to the connection between the extracorporeal circuit and the vascular system, there is freedom of movement for fluid to flow into and out of the extracorporeal circuit due to the relatively large volume of the patient's body to accommodate an influx of fluid or to serve as a reservoir of fluid.

The extracorporeal circuit is maintained such that a point of exit or entry of a significant fluid volume to the extracorporeal circuit, other that the patient's body, can be the movement of fluid across a dialysis membrane allowing for the diffusion of solutes between the patient's blood and the dialysate present in the dialysis circuit. A small volume of heparin or other anticoagulant can be added to the extracorporeal circuit to prevent clotting. The components of the dialysis circuit have a controlled compliant volume. Fluid is blocked from passively flowing from the extracorporeal circuit to the dialysis circuit due to the controlled compliant volume of the dialysis circuit. Fluid is prevented from passively flowing from the dialysis circuit to the extracorporeal circuit since such a movement of fluid will leave a vacuum in the dialysate circuit. Since the dialyzer can be a high-flux type there is some fluid flux back and forth across the dialyzer membrane due to the pressure differential on the blood and dialysate sides of the membrane. This is a localized phenomenon due to the low pressure required to move solution across the membrane and is called backfiltration, however results in no net fluid gain or loss by the patient.

While the components forming the dialysis circuit have a controlled compliant volume, the dialysis circuit further incorporates a control pump that can be operated to selectively adjust the volume of the dialysis circuit. Specifically, the action of typical pumps functions by expanding or contracting a space. When the control pump is provided on the dialysate circuit, the volume of the dialysate circuit can be expanded or contracted in a controlled fashion allowing for the movement of fluid across the dialysis membrane to be actively controlled by the user or a programmed controller. The control pump allows for fluid to move from the dialysate circuit to the extracorporeal circuit without creating a vacuum, wherein the operation of the control pump is controlled. Likewise, the control pump allows for fluid to move from the extracorporeal circuit, and hence the patient's body via the action of the control pump by selectively expanding the volume of the dialysis circuit. Movement of fluid between the extracorporeal circuit and the dialysis circuit can be accurately controlled and metered.

In certain embodiments, a control pump used in the invention can be a peristaltic pump, a volumetric metering pump, diaphragm pump, or a syringe style pump. During operation, the volume of the dialysate circuit changes continually during the treatment even when the system does not push fluid back into the patient. This volume changes in a controlled way. One typical dialysis blood pump peristaltic segment is 8 mm wherein during one rotation of the pump, two rollers can move approximately 14 mL. Depending on the position of the roller with this segment, there is 0 mL to 7 mL difference in dialysate flow path volume with this pump segment. This pump description is for illustration purposes and is non-limiting. The amount of the stroke volume will be dependent on the specific pump segment and the length of the blood pump race. A syringe pump can also always have a changing volume, as can a simple metering device such as a diaphragm flow meter. As the flow path volume changes, the volume will expand and contract based on the stroke of the pumps. This change can be controlled. Hence, the dialysate circuit has substantially a substantially inflexible volume except for controlled changes in volume modulated by the control pump, the infusion pump(s) and optionally a second control reservoir pump that reflect the changes in volume due to the position of the peristaltic roller, syringe plunger or meter diaphragm and whether the pump is run forward or in reverse. In another embodiment, the blood pump and dialysate pump can be run in-phase, or not run 180 degrees out-of-phase. In contrast, known systems run the blood pump and dialysate pump 180 degrees out-of-phase, i.e., when the blood pump pumps, the dialysate is stopped and vice versa. However, because the amount of water crossing into the blood during the dialysate stroke must be removed during the blood pump stroke, there is a tendency for the blood to hemoconcentrate and violate the blood filtration fraction. The ultrafiltration rate cannot exceed the acceptable filtration fraction. Filtration fraction (FF) is defined as FF (%)=(Ultrafiltration Rate×100)/Plasma flow. Plasma flow (Qp) is defined as Qp=Blood Flow Rate×(1-hematocrit). The maximum ultrafiltration rate cannot be greater than plasma flow×30%. The invention can also be programmed to have a physician prescribed maximum ultrafiltration rate which is lower than the filtration fraction derived maximum ultrafiltration rate. In the invention, the fluid flows, into and out of the circuits, are controlled so that the blood pump is running when the fluid is removed to avoid violation of the filtration fraction, and to avoid hemoconcentration for less clotting.

In certain embodiments, the invention contemplates a volume of dialysate less than about 1 L being conveyed through the dialysis system at any one time. In other embodiments, less than is 0.5 L is contemplated. FIG. 1A shows a system for circulating blood and a dialysate through a dialyzer 130. A shunt such as a needle or catheter is connected to a patient's vasculature to draw blood and circulate the patient's blood through an extracorporeal circuit 140. The portion of the extracorporeal circuit 140 that contains drawn blood from the patient can be referred to as the arterial line 610, which by convention is understood to mean a line for transporting blood from the patient regardless of whether blood is drawn from an artery or vein of the patient. Similarly, the portion that returns blood to the patient can be referred to as the venous line 620. In certain embodiments, the arterial line 610 and the venous line 620 connect with one or more veins of the patient. Locomotive power for moving the blood through the extracorporeal circuit 140 is provided by a blood pump 125, which is typically located along the arterial 610 line. Blood is typically conveyed through the extracorporeal circuit 140 at a rate of 50 to 600 mL/min and can be adjusted by a controller to any required rate suitable for a procedure performed by the invention. Blood pump 125 can be a peristaltic pump, although those skilled in the art will readily understand that other types of pumps can be used including diaphragm pumps, centrifugal pumps, and shuttle pumps. In certain embodiments, the blood pump 125 conveys blood through the dialyzer 130 where the blood is contacted with a blood side of a high permeability dialysis membrane 135. Blood enters the dialyzer 130 through a blood inlet 161 and exits through a blood outlet 162. The pressure of the blood prior to the blood pump 125 is measured by a pressure meter 133 and post dialyzer 130 by a pressure meter 134. The pressure at pressure meter 133 provides an indication of the adequacy of the blood flow into the circuit where increased vacuum is an indication of a less adequate access flow. The pressure indication at pressure meter 134 can serve to detect obstructions in the venous bloodline. An air trap 500 is placed along the extracorporeal circuit 140 to prevent the introduction of air into the circulatory system of the patient. The air trap 500 is not limited to a particular design. Typical air traps employ a hydrophobic membrane that allows air to be separated from an air-liquid mixture by allowing air to pass through the membrane and retaining water-based fluids. Alternatively the air trap 500 can be run full, where a pressure meter can use a flexible impermeable membrane to transmit pressure pulses to a pressure transducer such that there is no direct air blood interface. Air-fluid detectors 201 and 202 are present to confirm that air is not present in the extracorporeal circuit 140. Air fluid detectors 201 and 202 can be ultrasonic sensors that can detect a change in solution density or scattering due the presence of air or air bubbles.

During the course of conveyance of blood along the extracorporeal circuit 140, heparin or other anticoagulant is added to the blood to prevent clotting of blood within the dialyzer 130 or blood conveyance pathway/extracorporeal circuit 140. Heparin or another anticoagulant is added from an anticoagulant container 185 at a metered rate using an anticoagulant pump 186. The anticoagulant pump 186 can be any pump capable of accurately metering heparin.

Dialysate within the system is conveyed through one of a first dialysate pathway 108 in the dialysate circuit, which carries dialysate to the dialyzer 130, or a second bypass pathway 136 shown in a dashed line, which serves to bypass the dialyzer 130. The first and second pathways 108 and 136 have one or more conduits for conveying the dialysate. Access to the second bypass pathway 136 is controlled by valve 150. It is understood by one skilled in the art that three-way valve 150 can be replaced with a two-way valve with the same result to control the flow through the dialyzer 130 or bypass pathway 136. The first dialysate pathway 108, the second bypass pathway 136, and residual volume in the dialyzer 130 including conduits for conveying the dialysate together form a dialysis circuit 141 that houses the circulating volume of the dialysate present in the system. It is understood by one skilled in the art that three-way valve 150 could be replaced with two-way valves with the same result to control the flow through the dialyzer or bypass loop.

Dialysate that is conveyed through the dialyzer 130 on the dialysate side of the dialysis membrane 135 picks up waste produces from the blood, including urea, by diffusion, hemofiltration or hemodiafiltration. Dialysate enters the dialyzer at a dialysate inlet end 194 and exits at an outlet end 196. The dialysate exiting the dialyzer 130 passes through a blood leak detector 560 that can determine the presence of blood in the dialysate indicating a breach in the dialysis membrane 135. Flow of dialysate from the dialyzer 130 can be stopped or controlled through the operation of valve 158 as well as to prevent the backup of dialysate into the dialyzer 130. The dialysate is conveyed through a sorbent cartridge 102 to remove waste products before being re-conveyed through the dialyzer 130. The dialysate enters the sorbent cartridge 102 at a dialysate inlet end 197 and exits at an outlet end 195. An air trap 501 can be positioned before or after outlet end 195 to remove gasses introduced into the dialysate by the sorbent cartridge 102. The volume of actively circulating dialysate is determined by the total void volume of the conduits and the sorbent cartridge 102 forming both the dialysis circuit 141. The void volumes of the conduits and of the sorbent cartridge 102 forming the dialysis circuit 141 have an non-expandable or substantially inflexible volume.

The total void volume of the conduits having a substantially inflexible volume prevents the passive inflow and outflow of fluid volume due to pressure changes that can occur over the course of treatment. This results in a benefit because not all of the pressure changes during treatment are under precise control by a user or operator. A controlled compliance dialysis circuit is achieved by actively controlling the inflow (influx) and outflow (efflux) of fluid to and from the dialysis circuit 141 and the extracorporeal circuit 140. In this manner, the volume of fluid crossing the dialysate membrane 135 is under direct control and can be accurately determined. In certain embodiments, the dialysis circuit 141 has a void volume from about 0.15 L to about 0.5 L. In other embodiments, the dialysis circuit 141 has a void volume from about 0.2 L to about 0.4 L or from 0.2 L to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 L to about 5 L, and micro-volumes from as small as 0.1 L to about 0.5 L such as 0.1 L to 0.2 L, 0.1 L to 0.3 L, 0.1 L to 0.4 L, 0.2 L to 0.3 L, 0.3 L to 0.4 L, or 0.3 L to 0.5 L are contemplated by the invention.

The controlled compliance dialysis circuit can be accurately controlled to precisely remove or add fluid to the dialysis circuit. Due to the substantially inflexible void volume of the conduits, the sorbent cartridge 102 and other components of the dialysis circuit 141, the net movement of fluid over any time interval across the dialysate membrane can be accurately controlled by creating a means to accurately introduce or remove fluid from the patient. This capability is used to enhance the convective clearance of the system while controlling the net fluid removed from the patient.

As shown in FIG. 1, the dialysate is moved along the dialysis circuit 141 by a dialysate pump 138. When the control pump 190 is not operating, fluid along the length of the dialysis circuit 141 flows at a rate determined by the dialysate pump 138. When the control pump 190 is operating, fluid exiting the dialyzer 130 and traveling toward the conduit 191 is flowing at a rate that is the combination of the rates of the control pump 190 and the dialysate pump 138. However, the fluid traveling from the entry point of conduit 191 into the dialysis circuit 141 to the dialyzer 130 is traveling at the rate of the dialysate pump 138. As such, the rate of fluid traveling to the dialyzer 130 is not affected by the operation of the control pump 190. The dialysate pump can be operated at a rate from about 10 to about 400 mL/min, the specific rate being dependent on the rate of the blood pump 125 at the desired contact time with the dialysis membrane 125 to achieve diffusion of impurities from blood to the dialysate. The rate of the dialysate pump 138 and the blood pump 125 can be controlled by a controller 801 (shown in FIG. 30).

Refreshed dialysate exiting an outlet end of the sorbent cartridge 102 can be monitored by a conductivity meter 104. The design of any conductivity meter employed in embodiments described herein is not particularly limited; however, a typical conductivity meter has two electrodes where a current between the two electrodes is monitored. The presence of sodium ions in the dialysate is the major contributor to the conductivity measured by conductivity meter 104.

Conductivity is continually monitored and reported to the controller to assess the quality and safety of the dialysate. When the conductivity of the dialysate falls within a predetermined range, the dialysate is directed by valve 150 to a dialysate inlet end 194 of the dialyzer 130; the valve 150 is located between an outlet end 195 of the sorbent cartridge 102 and the dialysate inlet end 194 of the dialyzer 130. In certain embodiments, the valve 150 is a three-way valve. Optionally, the dialysate can be filtered through a microbial filter 512. The pressure of the dialysate entering the dialysate inlet end of the dialyzer 130 is measured by a pressure meter 137. In certain embodiments, the predetermined range for the conductivity of the dialysate is from about 12.6 to about 15.4 mS/cm.

When the conductivity measured by meter 104 is outside of the predetermined range, the valve 150 directs the dialysate to be conveyed through the second dialysis flow path 136 shown as a dashed line. Further, valve 158 can be closed to prevent the dialysate from backing up into the dialyzer 130. As such, the dialysate can be circulated through the sorbent cartridge 102 while bypassing the dialyzer 130 and preventing contact with the patient's blood when required. Since the dialysis circuit 141 is isolated from the extracorporeal circuit 140 when valve 158 is closed, the control pump 190 is not operated when valve 158 is in a closed position during normal operation. When the system is being primed, control pump 190 can operate to vent air from the dialysis circuit 141, as described below.

Due to the substantially inflexible void volume of the conduits and the sorbent cartridge 102, bulk fluid or water is prevented from moving across the membrane 135 from the extracorporeal circuit 140 of the dialyzer 130 to the dialysate circuit 141 of the dialyzer 130. Specifically, due to the controlled compliant feature of the void volume of the dialysis circuit 141, water cannot passively move from the extracorporeal side to the dialysate side through the dialysis membrane. In the event of factors that tend to increase pressure on the extracorporeal side of the dialysis membrane, such as increased blood flow rate or blood viscosity, pressure across the membrane will automatically be equalized due to the limited volume of the dialysis circuit 141 and the non-compressible nature of the dialysate. In the event of factors that tend to increase pressure on the dialysate side of the dialysis membrane 135, such as increased dialysis flow rate, net movement of water from the dialysis circuit 141 to the extracorporeal circuit 140 is prevented by a vacuum that would form in the dialysis circuit 141 in the event of such a movement. Since the dialyzer can be a high flux type, there is some fluid flux back and forth across the dialyzer membrane due to the pressure differential on the blood and dialysate sides of the membrane. This is a localized phenomenon due to the low pressure required to move solution across the membrane and is called backfiltration, however results in no net fluid gain or loss by the patient.

Using the controlled compliance dialysis circuit described herein, net movement of water across the dialysis membrane occurs under active control rather than passively due to pressure differences that develop across the dialysis membrane due to normal operations. A control pump 190 is present and accesses the controlled compliance dialysis circuit 141 through a conduit 191. In certain embodiments, the conduit 191 joins with the controlled compliance dialysis circuit 141 at a point downstream from the dialyzer 130. The control pump 190 can be operated in an influx direction that moves fluid from a control reservoir 192 to the controlled compliance dialysis circuit 141 or in an efflux direction that moves fluid from the controlled compliance dialysis circuit 141 into the control reservoir 192. Due to the substantially inflexible volume of the dialysis circuit 141, volume added to the controlled compliance dialysis circuit when the control pump 190 operates in the influx direction causes net movement of fluid from the dialysate side of the dialysis membrane 135 to the extracorporeal side of the dialysis membrane 135. When the control pump 190 is operated in the efflux direction, fluid is drawn from the extracorporeal side of the dialysis membrane into the controlled compliance dialysis circuit. In certain embodiments, the control pump 190 can be operated at a rate from 0 to about 500 mL/min in either direction. In certain embodiments, the control pump 190 can be operated at a rate from 0 to about 200 mL/min in either direction. In certain other embodiments, the control pump 190 can be operated at a rate from 0 to about 100 mL/min or 0 to 50 mL/min in either direction. Any range from about 0 to about 200 mL/min is contemplated by the invention such as about 15 to about 185 mL/min, about 25 to about 175 mL/min, about 5 to about 75 mL/min, about 61 to about 183 mL/min, about 156 to about 193 mL/min, about 32 to about 63 mL/min, about 145 to about 199 mL/min, about 16 to about 93 mL/min or, about 29 to about 124 mL/min.

Figure 1B:
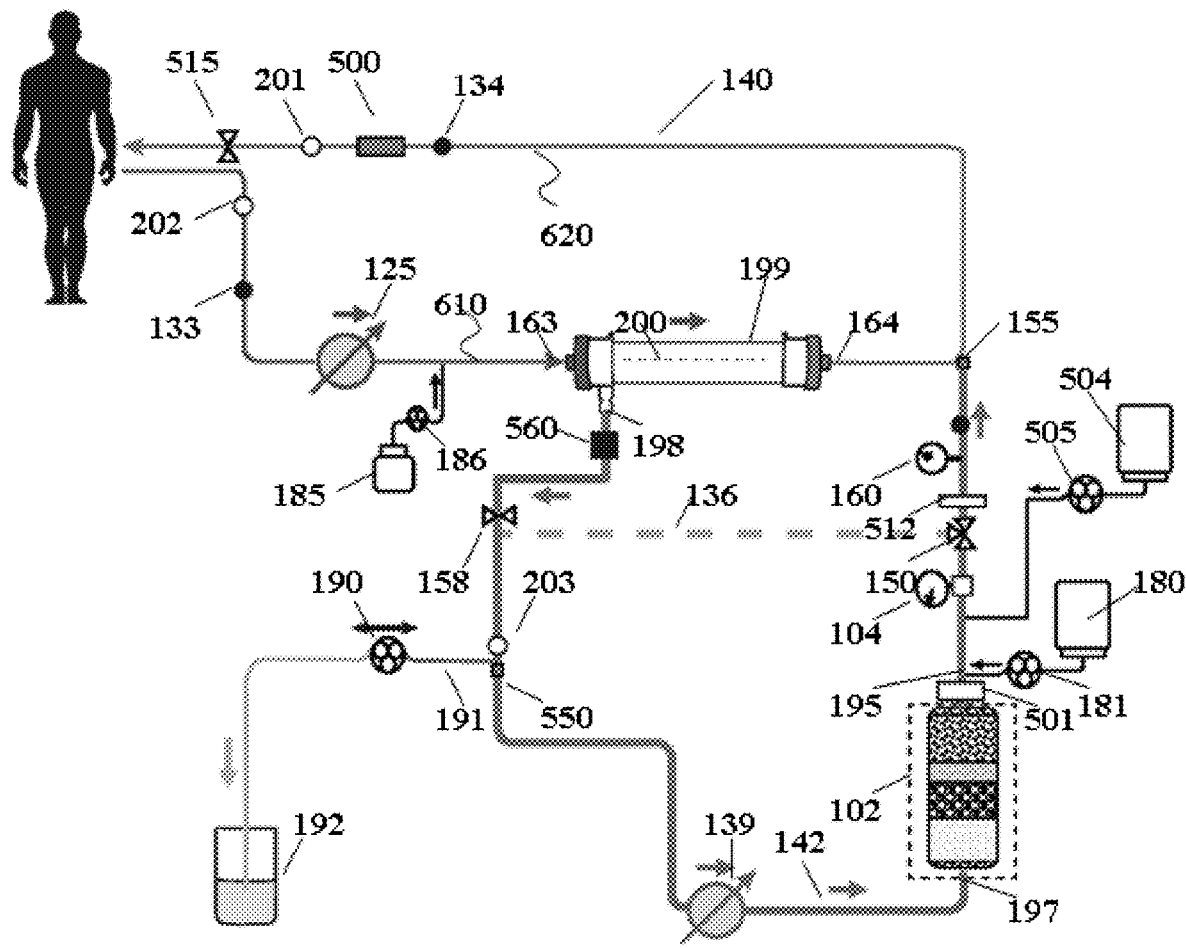
FIG. 1B shows a hemofiltration device having a controlled compliant filtration circuit operating in accordance with certain embodiments.

In embodiments where the control pump 190 is operated in the influx direction, the dialysate pump 138 operates at a rate higher than the control pump 190 to prevent flow of the used dialysate back into the dialyzer 130. The dialysate pump 138 functions to convey the dialysate from the point where line 191 joins the dialysis circuit 141 to the sorbent cartridge 102. A rate of the dialysate pump 138 operating faster than the control pump 190 in the influx direction ensures that the contents of the control reservoir 192 are conveyed to the sorbent cartridge 102 and do not reach the dialyzer 130 without first passing through the sorbent cartridge. In certain embodiments, the dialysate pump 138 operates at a rate that is about 100 mL/min greater and at rates greater than the rate of the control pump 190, when the control pump 190 is operating in the influx direction. For example, if the rate of the control pump 190 is 10 mL/min, the dialysate pump 138 can operate at rates greater than about 110 mL/min such as 130 mL/min, 175 mL/min, 210 mL/min, 510 mL/min, 760 mL/min, 1 L/min, and 1.6 L/min. If the rate of the control pump 190 is 25 mL/min, the dialysate pump 138 can operate at rates greater than about 125 mL/min such as 130 mL/min, 175 mL/min, 210 mL/min, 510 mL/min, 760 mL/min, 1 L/min, and 1.6 L/min. In one embodiment, the dialysate pump 138 operates at a rate that is about 20 mL/min greater and at rates greater than the rate of the control pump 190 or higher, when the control pump 190 is operating in the influx direction. In other embodiments, the dialysate pump 138 operates at a rate that is about twice the rate and at rates greater than that of the control pump 190, when the control pump 190 is operating in the influx direction. In certain embodiments, the dialysate pump 138 operates at a rate that is about 5% higher and at rates higher than the rate of the control pump 190, when the control pump 190 is operating in the influx direction. For example, the dialysate pump 138 can operate at 6%, 7%, 8%, 10%, 15%, 45%, 63%, 75%, 100%, 200%, 500%, 2000%, or any higher percentage than the rate of the control pump 190. The pump rates described herein are also applicable to the controlled compliance hemofiltration circuit 142 configured for use in a hemofiltration system as shown in FIG. 1B.

The control reservoir 192 is not limited to any particular structure. In certain embodiments, the control reservoir 192 can be made from a flexible or collapsible material that expands depending on the volume held. In certain embodiments, the control reservoir 192 can be substantially inflexible. The control reservoir 192 can include a hydrophobic 0.2 micron (μm) sterile, non-pyrogenic, and non-toxic air filter 300 to prevent the entry of bacteria or endotoxin into the control reservoir 192 and dialysis circuit 141. The air filter 300 also sterilizes air exhaust and intake from the control reservoir 192 into the system. Further, the air filter 300 can release air pressure present in the control reservoir 192. The material of air filter 300 may be Millipore Dualex™ filter or an equivalent known to one of ordinary skill. In certain embodiments, the control reservoir 192 can have a valve that allows the patient or subject to empty the volume of the control reservoir 192 without interrupting treatment.

Several sensors and monitors can be employed to determine the state of the dialysis system, as shown in FIG. 1A. Blood leaks across the dialysis membrane 135 can be detected by a blood leak detector 560. The blood leak detector 560 can be an optical detector having a light source and photo detector allowing for the observation of a red color in the dialysate. The presence of air or fluid in the extracorporeal 140 and dialysis circuits 141 can be determined by air-fluid detectors 201, 202, and 203, which can be ultrasonic sensors that can detect a change in solution density or scattering due to the presence of air or air bubbles. Conductivity meters 101, 104 and 160 can be present to monitor the composition of the dialysate within the dialysis circuit. Pressure meters 133, 134 and 137 can be present to determine unsafe operating pressure and/or fluid leak from the system. The pressure meter can be a transducer device that operates through capacitive or piezoelectric principles to convert the amount of force applied to a surface to an electronic signal.

Controlled Compliance Hemofiltration Circuit for Hemofiltration System

As described above, the controlled compliance dialysis circuit 141 is configured to control fluid flow through a dialysis membrane 135. A controlled compliance hemofiltration circuit 142 is similarly configured for use in a hemofiltration system, as shown in FIG. 1B. The controlled compliance hemofiltration circuit 142 has a flow path with a substantially inflexible volume between the ultrafiltrate outlet 198 of a hemofilter 199 and a point of introduction of replacement fluid 155 into the extracorporeal circuit 140. The conduits, sorbent cartridge 102 and other components for conveying fluid between ultrafiltrate outlet 198 and point of introduction of replacement fluid 155 into the extracorporeal circuit 140 have a substantially inflexible volume. A control pump 190 and a filtrate pump 139 can accurately control the removal of fluid and the introduction of a replacement fluid due to the controlled compliant properties of the hemofiltration circuit 142.

In traditional hemofiltration systems, fluid is removed from the blood of a subject through the application of a negative pressure to a hemofilter to draw off an ultrafiltrate. Hemofiltration serves to remove waste species from the blood by convection or solute drag, which has greater effect in removing mid-weight and heavier waste species compared with dialysis methods. However, the human body on average contains about 5 L of blood volume. As such, it is necessary to balance the volume of fluid removed from the extracorporeal circuit 140 with a volume of replacement solution that is added to the extracorporeal circuit 140 to prevent concentration of the blood and hypovolemic episodes. In traditional systems, the replacement solution is separately prepared and infused into the extracorporeal circuit 140, and the filtered volume and the infused/replacement volume is balanced by either gravimetric, volumetric or flow cell techniques to avoid rapid changes in blood volume and concentration while performing hemofiltration.

As shown in FIG. 1B, the controlled compliance filtration circuit 142 eliminates the need for complicated gravimetric (e.g. scales) and volumetric equipment to balance the rate and volume of filtrate removal with the rate and volume of replacement fluid infusion into the extracorporeal circuit. In FIG. 1B, an extracorporeal circuit 140 is provided having a similar configuration as the extracorporeal circuit 140 shown in FIG. 1A, except the dialyzer 130 is replaced with a hemofilter 199 having a hemofiltration membrane 200. Blood enters the hemofilter 199 at a blood inlet 163 and exits at a blood outlet 164 while contacting one side of the hemofiltration membrane 200.

Operation of a filtrate pump 139 generates a negative pressure at the ultrafiltrate outlet 198 of the hemofilter 199. The extracorporeal circuit 142 can be pre-primed or filled with fluid prior to operation and the hemofiltration membrane 200 can be a high-flux type membrane, such that application of negative pressure to the ultrafiltrate outlet 198 does not result in the formation of a vacuum. Operation of the filtrate pump 139 at a specific rate will result in substantially the same rate of ultrafiltrate removal from the extracorporeal circuit 140 to the hemofiltration circuit 142. The rate of ultrafiltration or flux of fluid across the hemofiltration membrane 200 can be precisely controlled due to the substantially inflexible volume of the hemofiltration circuit 142. The ultrafiltrate is conveyed by the filtration pump 139 to a sorbent cartridge 102 that removes waste species, such as urea, from the ultrafiltrate as will be described in greater detail below. The sorbent cartridge 102 also removes electrolytes (e.g. $Ca^{2+}$, $Mg^{2+}$, $K^+$) found in the ultrafiltrate. An infusate pump 181 is used to add a cation infusate 180 into the hemofiltration circuit 142 to generate a fluid having a proper physiological composition to serve as a replacement fluid for introduction into the extracorporeal circuit 140. A bicarbonate solution in a container 504 can further be added by a pump 505 to maintain a physiological pH in the fluid prior to introduction to the extracorporeal circuit as described below. The operation of the valve 150, bypass pathway 136, conductivity meters 102 and 160, air trap 501 and other like elements sharing an element number with those elements found in FIG. 1A have similar structure and operation to element features described elsewhere in this document.

As described, the filtrate pump 139 controls the rate and volume of ultrafiltration occurring during the hemofiltration treatment and further controls the rate of generated replacement fluid infused into the extracorporeal circuit 140. Since the replacement solution is generated from the filtrate, the rate of fluid removal and infusion of replacement infusion is substantially balanced without the use of scales and/or volumetric devices. However, it should be noted that operation of pumps 181 and 505 add a small volume to the replacement fluid for infusion.

It is also possible to perform ultrafiltration with net fluid removal from the patient through use of the control pump 190. Where the filtrate pump 139 and the control pump 190 are used simultaneously, the combined rate of the filtrate pump 139 and the control pump 190 controls the rate of filtration or fluid removal from the extracorporeal circuit. For example, if the filtrate pump 139 is operated at a rate of 50 mL/min and the control pump 190 operates at 12 mL/min, then the rate of fluid removal at ultrafiltrate outlet 198 is 62 mL/min. The control pump 190 drains a portion of the total ultrafiltrate into a control reservoir 192 to be discarded later. The rate of the control pump 190 controls the net volume of fluid removed from the patient over the time course of treatment, since this removed fluid is not infused into the extracorporeal circuit 140 as replacement fluid.

In situations where the filtrate pump 139 and the control pump 190 are used simultaneously, the rate of conveyance of fluid to the sorbent cartridge 102 for treatment to generate a replacement fluid will be the rate of the filtrate pump 139. It should be noted that the rate of the control pump 190 can be adjusted by a controller 801 to compensate for any volume addition by pumps 181 and 505. In the example above where the filtrate pump 139 is operated at a rate of 50 mL/min and the control pump 190 operates at 12 mL/min, filtrate is removed from the subject at a rate of 62 ml/min and replacement fluid is added to the extracorporeal circuit 140 at a rate of 52 ml/min (assuming pumps 181 and 505 operate at 1 mL/min), where net fluid removal from the subject is 10 mL/min or 600 mL over an hour of treatment. One having skill in the art will be able to determine and understand the resultant effects of the rate of ultrafiltrate generation, rate of fluid replacement, and rate and net amount of fluid removal caused by operating any of pumps 505, 181, 190, and 139 at any specific rate.

The same rules for filtration fraction discussed above for the hemodialysis circuit 141 are applicable to the hemofiltration circuit 142. It is desirable to limit the rate of filtration or fluid removal through ultrafiltration port 198 to avoid problems of hemoconcentration and blood clotting. The ultrafiltration rate should not exceed an acceptable filtration fraction. Filtration fraction (FF) is defined as FF (%)= (Ultrafiltration Rate×100)/Plasma flow. Plasma flow (Qp) is defined as Qp=Blood Flow Rate×(1-hematocrit). The maximum ultrafiltration rate cannot be greater than plasma flow× 30%.

For example, FIG. 1B shows a system where hemofiltration occurs at a point prior the addition of replacement fluid at point 155. If blood hematocrit is 30% and blood flow through the hemofilter 199 is 300 mL/min, then Qp=300 mL/min*(1−0.3)=210 mL/min. The maximum rate of ultrafiltration can then be set at 30% of Qp or 63 mL/min. As such, the control pump 190 and the filtrate pump 139 should not be operated at a combined rate higher than 63 mL/min.

In an alternate embodiment, the replacement fluid can be added to the extracorporeal circuit 140 prior to the hemofilter 199. The replacement solution can be added to the arterial line 610 of the extracorporeal circuit 140. Under a scenario where hematocrit is 30% and blood flow rate is 300 mL/min, hematocrit will be reduced to 25.7% upon addition of the replacement fluid, where 50 mL/min of replacement solution is added to the blood flow. Where the total flow rate through the hemofilter 199 is 350 mL/min due to the addition of the replacement fluid, Qp will be equal to 350 mL/min*(1−0.257) or 260 mL/min Qp, which allows for a maximum ultrafiltration rate of 78 mL/min under such a scenario. These examples are provided for illustrative purposes and are not limiting. One having skill in the art can easily calculate Qp for any combination of blood flow rate and hematocrit and set a maximum ultrafiltration rate accordingly.

Ultrafiltration and Increased Convective Clearance

With regard to the systems configured as shown in FIGS. 1A and 1B, the compliance control pump 190 is operated by a controller 801 that accurately accounts for the volume of fluid being removed from the circulation of the patient and/or being infused into the circulation of the patient. As described above, the control pump 190 controls the movement of fluid across the dialysis membrane 135 due to the controlled compliant volume of dialysis circuit 141 or together with the filtrate pump 139 for the hemofiltration circuit 142. In the configurations shown in FIGS. 1A and 1B, operation of the control pump 190 controls the rate and amount of net removal of fluid from the subject during treatment. Many kidney failure patients can have fluid build-up that may be addressed by ultrafiltration, where bulk fluid is removed via the circulatory system. The control pump 190 can be accurately used to determine the precise volume of fluid removed from the patient. In addition to accurately controlling the net fluid removed and the convective clearance of a patient, accurate control of the efflux or influx of fluid via the control pump 190 allows for the amount of sodium removed (mEq $Na^+$) during a course of treatment to be determined, where such result can be calculated and stored in the memory of a controller 801 and/or be displayed on a control panel (not shown).

In the dialysis system of FIG. 1A, accurate control of bulk fluid movement across the dialysis membrane can further be used to enhance clearance of mid-weight impurities by convective clearance, which is particularly beneficial for mid-weight impurities such as $\beta$2-microglobin that are not removed very well by hemodialysis and for which higher serum blood levels are associated with higher patient mortality. To be able to control net patient fluid removal, any fluid removed in excess of the desired patient fluid loss must be reinfused to the blood. This is accomplished in one embodiment by running a control pump in reverse during the treatment and then compensating by ultrafiltration (UF): Control Pump Control=Net patient UF+Convective UF. Control pump backfiltration is controlled to Convective UF volume. For example, a desired 200 mL net patient fluid loss per hour and 1000 ml of convection per hour requires a control pump running at a UF (efflux) rate of 1000 mL/hr and at a backfiltration (influx) rate of 800 mL/hr to achieve the net fluid loss and the desired convective clearance. These same mechanisms allow one to give fluid to the patient when necessary, return blood to the patient and control fluid removal accurately.

The rate of diffusion of a solute is dependent upon the molecular weight of that solute. Small molecules, such as urea, can effectively diffuse from the extracorporeal side of the dialysis membrane to the dialysate side of the dialysis membrane in the absence of net movement of fluid. However, larger, "mid-weight uremic impurities", having a lower rate of diffusion may not be removed as effectively. As used herein, the term "mid-weight uremic impurities" refers to an impurity having a molecular weight less than about 66000 g/mol and greater than about 1000 g/mol and includes uremic toxins, B12, C reactive protein, and $\beta$2-microglobin.

During periods of net movement of fluid from the extracorporeal side to the dialysate side of the dialysis membrane 135, solutes can be dragged across the dialysis membrane 135 along with the net movement of fluid. This process, referred to as convective clearance, removes mid-weight impurities from the patient's blood, which are absorbed by the sorbent cartridge 102. Some convective clearance occurs during the course of ultrafiltration as described above. However, the amount of convective clearance is limited by the volume of fluid that is removed by ultrafiltration. For example, if 1 L of fluid is to be removed from the patient over the course of a 4-hour treatment, then the amount of convective clearance that occurs due to 1 L of fluid crossing the dialysis membrane 135 is the maximum amount of convective clearance that occurs during the treatment regimen. Without infusing the patient with additional fluid, the amount of fluid that can be removed is limited considering that the average individual has about 5 L of blood. Further, it may be desirable to achieve convective clearance without the removal of a large amount of fluid from the patient.

To achieve convective clearance in accordance with certain embodiments, the control pump 190 is operated in the efflux direction to pull fluid from the extracorporeal circuit 140, and hence from the patient, across the dialysis membrane 135. During the net efflux for fluid across the membrane 135, mid-weight solutes and impurities are carried into the circulating dialysate where they can be absorbed by the sorbent cartridge 102. The control pump 190 is periodically reversed to the influx direction to force fluid from the control reservoir 192 into the controlled compliance dialysis circuit and thereby force a corresponding volume of fluid into the extracorporeal circuit 140 and into the patient. During influx, fluid from control reservoir 192 is not returned to the dialyzer 130 and must first pass through the sorbent cartridge 102. As discussed herein, pressures, rates, and control means are adjusted to ensure that used dialysate is not returned to the dialyzer 130 from the dialysate circuit 141.

Under a regime where the control pump 190 is run in the efflux and influx directions for approximately equal amounts of time at the same pump rate, the amount of convective clearance will be approximately the efflux flow rate without causing any net addition or removal of fluid from the patient. For example, if the control pump 190 is run at 10 mL/min for a hour with periodic reversal between efflux and influx directions, then 300 mL of fluid is moved from the extracorporeal circuit into the controlled compliance dialysis circuit 141 to affect convective clearance where the same volume is returned to the patient resulting in no net fluid removal at the end of treatment. In the alternative, the time that the control pump 190 is operated in the efflux or influx direction can be unequal to affect a net volume of ultrafiltration during the course of treatment. For example, if the control pump 190 is operated in the efflux direction for 18-second periods with intervening 12-second periods in the influx direction at a rate of 10 mL/min, then 360 mL/h of fluid is moved in the efflux direction to affect convective clearance and a net of 120 mL/h of fluid is removed from the patient. Those skilled in the art will understand that the interval at which the control pump 190 operates between efflux and influx directions can be modified to further effect the amount of convective clearance and net ultrafiltration occurring over the course of treatment.

The blood pump 125 and the dialysate pump 138 provide the majority of the energy to convey the blood through the extracorporeal circuit 140 and the dialysate through the controlled compliance dialysis circuit 141, respectively. In certain embodiments, the blood pump and the dialysate pump can be independently operated at any rate in a range from about 50 mL/min to about 300 mL/min including from about 60 mL/min to about 295 mL/min. Other rates are contemplated, such as about 76 mL/min to about 185 mL/min, about 85 mL/min to about 287 mL/min, about 25 mL/min to about 115 mL/min, about 45 mL/min to about 273 mL/min, about 156 mL/min to about 293 mL/min, about 32 mL/min to about 163 mL/min, about 145 mL/min to about 199 mL/min, about 167 mL/min to about 193 mL/min or, about 29 mL/min to about 224 mL/min. In certain embodiments, the blood pump and/or the dialysate pump deliver a constant load pressure such that the conveyance rate is constant over at least short periods of times. Pumps that can deliver a constant load pressure include peristaltic pumps. The filtrate pump 139 can be operated at any of these rates as well.

The use of pulsatile pumps, that mimic the pulsing action of the human heart, has been proposed to enable convective clearance. As discussed herein, in known devices, the blood and the dialysate are conveyed by pulsatile pumps that are set 180 degree out of phase in order to achieve periodic filtering across the dialysis membrane. When the blood pump is undergoing a pulse action and the dialysate pump is at rest, convective clearance can occur due to an increase in pressure difference across the dialysis membrane. Conversely, fluid is back filtered across the dialysis membrane when the dialysate pump is undergoing a pulse action and the blood pump is at rest. However, such systems have been subject to increased clotting. It is desirable to stop the administration of heparin or other anticoagulant 30 to 60 minutes prior to the end of dialysis to restore normal clotting by the time treatment ends. However, blood becomes significantly more viscous at low flow rates. In addition, protein coats the membrane surface, starting the clotting cascade. The periodic slow down of blood circulation caused by the action of a pulsatile pump contributes to clotting occurring in the extracorporeal circuit. Blood clotting prevents the completion of treatment.

In the invention, the method for performing convective clearance using pulsatile pumps requires the flow rate of the blood and the dialysate through the dialyzer to be similar to function properly. The pressure generated in the dialyzer on either side of the dialysis membrane is dependent upon the flow rate, where the flow rate of the dialysate and the blood should be close to achieve equal movements of fluid in both directions across the dialysis membrane. Specifically, the ratio of blood flow to dialysis flow has been recommended to be from 3:4 to 4:3 when employing pulsatile pumps to increase convective clearance. The use of pulsatile pumps to perform convective clearance also increases hemoconcentration, which increases the risk for blood clotting. As the flow rate of blood through a dialyzer is lowered relative to the flow rate of dialysate through the dialyzer, any particular volume of fluid pulled from the extracorporeal circuit during a unit value of time causes a greater amount of hemoconcentration. That is, the volume of fluid removed from the extracorporeal circuit is removed from a smaller volume of blood as the flow rate of blood is lowered. As described above, a ratio of blood flow to dialysis flow has been recommended to be from 3:4 to 4:3 when pulsatile pumps are used to create convective clearance. Using the controlled compliance dialysis circuit described herein, the net flux of fluid across the dialysis membrane 135 is controlled by the control pump 190 rather than a ratio of flow rates between blood and dialysate. Hence, the ratio of blood flow to dialysate flow can be set at a value that reduces hemoconcentration as a result of pulling fluid from the extracorporeal circuit. In certain embodiments, the ratio of blood flow to dialysate flow through the dialyzer 130 is from about 1:1.5 to 3:1, and can include any range of ratios in between. In certain other embodiments, the rate of blood flow through the dialyzer 130 is at least about 50% greater than the rate of dialysate flow through the dialyzer 130.

Sodium and Cation Control

As will be described in greater detail below, the sorbent cartridge acts as a cation exchanger to absorb ammonia ions and other cations (e.g. $K^+$, $Ca^{2+}$, and $Mg^{2+}$) and release sodium ions and hydrogen ions in a stoichiometric fashion. In certain embodiments, the dialysate cartridge passes dialysate entering an inlet end 197 of the sorbent cartridge through a flow path having a urease-containing material. The urease in the urease-containing material converts urea to ammonium ions and carbon dioxide. The ammonium ions created through the action of urease are absorbed by a zirconium phosphate material by cation exchange with sodium ions. In certain other embodiments, the sorbent cartridge contains an alternate flow path that allows at least part of the used dialysate from the dialyzer to pass through a mixed bed anion/cation exchange (mixed bed de-I) resin prior to entering the sorbent cartridge to control the concentration of sodium ions in the circulating dialysate. In any embodiment the zirconium phosphate may be replaced with magnesium phosphate.

Without adjustments, sodium ion concentration will increase to unsafe levels over the course of treatment due primarily to the function of the zirconium phosphate material. The normal constituents of the dialysate are $Na^+$ from 137 to 142 mEq/L, $K^+$ from 1 to 4 mEq/L, $Ca^{2+}$ from 2 to 3 mEq/L, $Mg^{2+}$ from 0.5 to 1 mEq/L and $HCO_3^-$ from 32 to 40 mEq/L. There is also typically a small amount of acetic or citric acid and dextrose in the solution. Sodium ions ($Na^+$) are the major ionic content of dialysis solution in the standard composition. Sodium is given off by the sorbent cartridge 102 as a result of the exchange of ammonium, carbonate, calcium, magnesium and potassium by the zirconium phosphate material of the sorbent cartridge 102. To gain an estimate of the magnitude of sodium ions added to the dialysate over the course of a typical treatment, removal of 10 grams urea during a daily therapy would result in the subsequent exchange of ammonium for sodium equal to about 180 mEq of sodium. The further exchange of $Ca^{2+}$, $mg^{2+}$ and $K^+$ for $Na^+$ results in the production of about 240 mEq sodium. The sorbent cartridge 102 acts to remove urea by the conversion of the neutral urea molecule to ammonium ions that are removable by cation exchange. The generation and removal of ammonium ions causes the production of increasing amounts of $Na^+$ ions as urea is removed from the dialysate.

The sorbent cartridge 102 functions to remove substantially all ammonium, $Ca^{2+}$, $Mg^{2+}$ and $K^+$ cations from the dialysate passing though the cartridge in exchange for $Na^+$ and hydrogen ions. The concentration of cations $Ca^{2+}$, $mg^{2+}$ and $K^+$ is maintained at near the physiological concentration in the dialysate; therefore, the dialysis treatment does not have a significant effect on the concentration of these cations by dialysis across the dialysis membrane 138. However, $Ca^{2+}$, $Mg^{2+}$ and $K^+$ must be replenished in the dialysate exiting the sorbent cartridge 102, since the sorbent cartridge 102 removes these cations. Therefore, a concentrated cation solution is added to the dialysate from an infusate container 180 by means of a pump 181. In certain embodiments, the pump 181 is operated at a constant rate to maintain stable amounts of $Ca^{2+}$, $Mg^{2+}$ and $K^+$. The point at which the infusate (i.e. cation) solution is added to the dialysate can be between the sorbent cartridge 102 and the valve 150 in certain embodiments. It should be noted that since the amounts of $Ca^{2+}$, $Mg^{2+}$ and $K^+$ remain stable over the course of treatments, fluctuations in conductivity of the dialysate over the course of treatment is primarily attributable to changes in sodium ion concentration.

Some of the sodium ions produced by the sorbent cartridge 102 are removed by the control pump 190 operating to remove a net volume of fluid from the patient by means of the extracorporeal circuit 140. Since the conductivity of the dialysate is monitored by conductivity meter 104, the controller 801 operating the control pump 190 can calculate the amount of sodium ion removed with a net removal of fluid, since the conductivity contributed by other cations (e.g. $Ca^{2+}$, $Mg^{2+}$ and $K^+$) remains relatively constant during the course of treatment. For example, if the sodium ion concentration in the dialysate is at a normal physiological level, then each net liter removed by the control pump 190 removes 140 mEq of sodium ions. For a typical daily hemodialysis treatment, the average amount of ultrafiltration is 1 to 1.5 liters per session. In the controlled compliance hemofiltration circuit 142 shown in FIG. 1B, the replacement fluid generated by the removal of waste species and impurities from the ultrafiltrate by sorbent cartridge 102 is directly infused to extracorporeal circuit 140 and the subject. Electrolytes are required to be infused into the replacement fluid prior to introduction to the extracorporeal circuit 140. An infusate can be added by pump 181 as described above to generate a physiologically compatible infusate and/or valve 150 can be operated to bypass the replacement fluid through bypass pathway 136 as required if an unsafe conductivity is detected.

Figure 2:
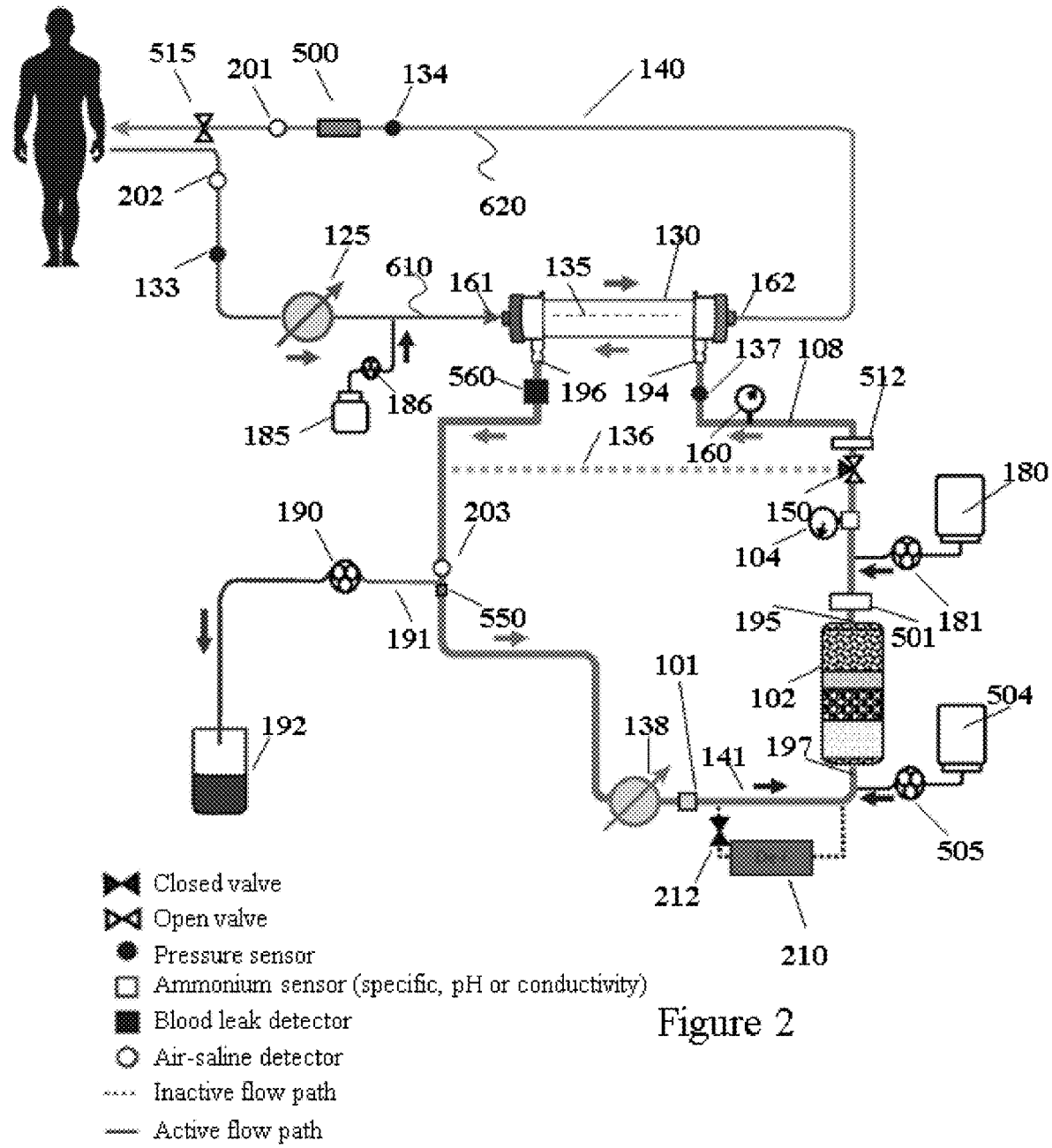
FIG. 2 shows a hemodialysis device having a controlled compliant dialysis circuit and a mixed bed deionization column operating in accordance with certain embodiments.

As required, the content and conductivity of the dialysate can be adjusted. This adjustment can occur without adding any volume of fluid to the dialysis circuit 141. FIG. 2 shows an apparatus sharing features with the apparatus of FIG. 1A. In addition to the sorbent cartridge 102 that serves as a source of sodium ions from cation exchange, an optional deionization cartridge 210 can be placed in the dialysate flow path. The deionization cartridge 210 can be present to assist with the removal of sodium ions from the dialysate in certain embodiments. In embodiments where the deionization cartridge is not present, sodium concentration in the dialysate can be reduced by operation of the control pump 190, where fluid introduced into the dialysis circuit from the blood can act as a diluent. The deionization cartridge 210 has a mixed anion and cation de-ionization (mixed bed de-I) resin that is placed in series with the sorbent cartridge 102. Dialysate that is circulated through the deionization cartridge 210 is outputted as substantially deionized purified water having low conductivity due to the action of the mixed anion/cation resins. Hence, the effluent from deionization cartridge 210 can act a diluent for sodium ion concentration in the dialysate.

A conductivity meter 101 can be present near deionization cartridge 210 for the purpose of controlling the setting of valve 212 for diverting at least a portion of the dialysate flow through deionization cartridge 210. Alternatively, conductivity meter 104 and/or 160 can be used for determining the setting of valve 212. When the conductivity measured by conductivity meters 101, 104 and/or 160 is above a predetermined range, valve 212 is actuated to divert at least part of the dialysate flow through the deionized column prior to being passed to the sorbent cartridge 102. The operation of the valve 212 is under control of the controller 801 monitoring the conductivity measured by conductivity meters 101, 104 and/or 160. If necessary, the valve 150 can be operated to divert dialysate flow through the second flow path 136 to protect the patient from an increase in dialysate conductivity. Flow through the deionization cartridge 210 is controlled in response to the conductivity of dialysate exiting the sorbent cartridge 102 and dialyzer 130. When the conductivity of the dialysate is too high, the valve 212 is opened at least temporarily to divert at least a portion of the flow of dialysate through the deionization cartridge 210. The mixed bed de-I resin removes the electrolytes, including sodium ions, and releases substantially deionized water that acts as a diluent in the system to control sodium ion concentration.

It should be noted that under treatment regimens where the control pump 190 removes a net amount of fluid from the dialysis circuit 141 through operation in the efflux direction, equivalents of $Na^+$ are removed from the system. Operation of the control pump 190 in the efflux direction to remove a net amount of fluid also reduces the sodium level in the dialysate. Specifically, fluid moving from the blood across the dialysis membrane 135 into the dialysis circuit 141 acts as a diluent for $Na^+$ concentration and conductivity. As described above, the controller 801 can calculate and monitor the removal of $Na^+$ from the system. Hence, the deionization cartridge 210 is not the sole means for reducing the $Na^+$ concentration and conductivity of the dialysate.

Regeneration of Dialysate and Generation of Replacement Fluid

The sorbent cartridge 102 acts to remove waste species and impurities in a similar manner for both the dialysis system of FIG. 1A and the hemofiltration system of FIG. 1B. For simplicity, the regeneration of a dialysate will be described where it is understood that the same principles apply to generation of a replacement fluid from a filtrate. The sorbent cartridge 102 removes impurity or waste species transferred to the dialysate in the dialyzer 130 prior to reuse as refreshed dialysate. Sorbent materials that can perform removal of waste products and regenerate the dialysate for use in the controlled compliance dialysis circuit 141 are known. Examples of useful sorbent materials include the REDY sorbent system and U.S. Pat. Nos. 3,669,880; 3,989,622; 4,581,141; 4,460,555; 4,650,587; 3,850,835; 6,627,164; 6,818,196; and 7,566,432 and U.S. Patent Publications 2010/007838; 2010/0084330; and 2010/0078381 and International Patent Publication WO 2009/157877 A1, which are incorporated herein by reference. The sorbent cartridge 102 typically contains at least four different kinds of materials as follows: 1) a urease-containing material, where urease is an enzyme that catalyzes the conversion of urea to ammonium ions and carbon dioxide; 2) a zirconium phosphate (ZrP) material that has the capacity to act as a cation exchanger by absorbing a large quantity of ammonium ions in exchange for sodium and hydrogen ions; 3) a zirconium oxide material (ZrO), which acts as an anion exchanger by exchanging phosphate for acetate; and 4) an activated carbon material that has a surface area for adsorption of wide range of impurities including metal ions and uremic toxins, such as uric acid, creatinine, and β2-microglobin. In some embodiments, the zirconium phosphate material can be replaced with a magnesium phosphate material.

In certain embodiments, the urease-containing material, the zirconium phosphate material, the zirconium oxide material, and the activated carbon material are arranged into discrete layers within the sorbent cartridge 102. As will be described in more detail below, the various sorbent materials can be provided in separate housings or as discrete layers within such housings in certain embodiments. In certain embodiments, the urease-containing material and the zirconium phosphate material are intermixed in the same discrete layer within the sorbent cartridge 102. The urease-containing material can be immobilized or covalently linked to a substrate material. The substrate material is not particularly limited, where suitable substrate materials include organic polymers, carbohydrate-based polymers, polyamides, polyesters, inorganic polymeric materials, chitosal and silica gel. The inclusion of the urease-containing material and the zirconium phosphate material in the same discrete layer can improve workability of the sorbent materials to prevent clogging of the sorbent cartridge 102 or improve absorption of ammonium ions by the zirconium phosphate material.

A typical sorbent cartridge 102 passes dialysate entering the cartridge 102 through the urease-containing material, the ZrP material, the ZrO material and the activated carbon material in that order. Some sorbent cartridges 102 can contain an additional activated carbon material that contacts the used dialysate prior to the urease-containing material to remove metal ions or fluorine ions that can damage the urease-containing material. Still other sorbent cartridges 102 can contain more than one activated carbon layer including an activated carbon layer at the inlet and at the outlet of the sorbent cartridge.

Exemplary sorbent cartridges 102 are shown in FIGS. 3 and 4. The systems and controlled compliant dialysis circuit 141 disclosed herein are not particularly limited to the use of any particular sorbent cartridge. FIG. 3A shows a sorbent cartridge having a conical-shaped body 235 in accordance with certain embodiments. The conical-shaped body 235 is desirable for imparting smooth flow characteristics for the used dialysate 230 entering the sorbent cartridge 102 and the regenerated effluent dialysate 250. A urease-containing material 240, a ZrP material 242, a ZrO material 244 and an activated carbon material 246 are present inside the cartridge body 235, as shown. Those skilled in the art will understand that various frits, baffles, and other internal elements can be present to support the sorbent materials, to compress the sorbent materials and to prevent the escape of fines.

Figure 3A:
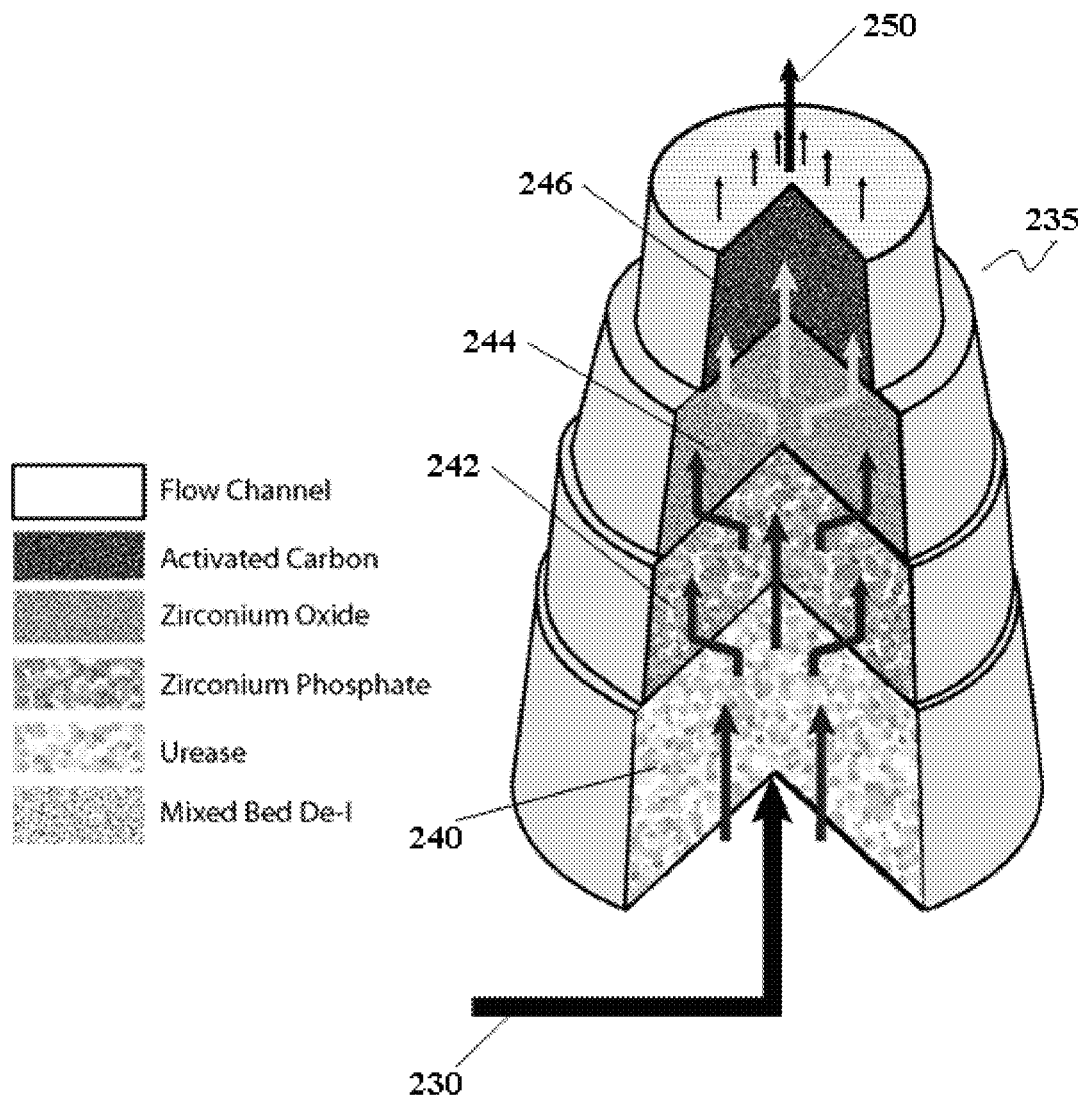
FIGS. 3A through 3E show sorbent cartridges in accordance with certain embodiments.
Figure 3B:
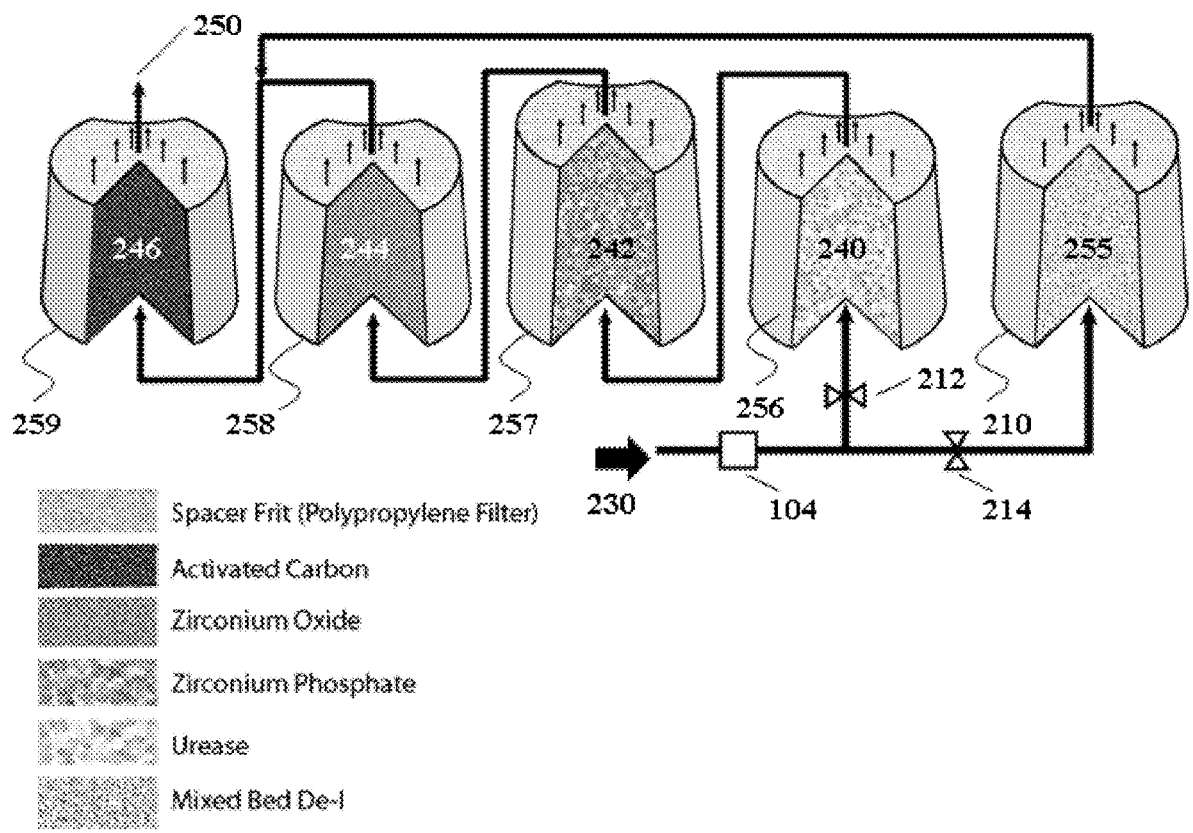

FIG. 3B shows an additional embodiment of a sorbent cartridge 102. As shown in FIG. 3B, the sorbent materials can be divided into five separate housings 210, 256, 257, 258 and 259. Housing 210 can serve as the deionization cartridge and contain a mixed bed de-I resin 255. However, the use of a deionization cartridge is optional and can be omitted in certain embodiments. In such embodiments, housing 210 and valves 212 and 214 can be omitted from the sorbent cartridge 102 shown in FIG. 3B. Housings 256, 257, 258 and 259 contain the urease-containing material 240, the ZrP material 242, the ZrO material 244, and the activated carbon material 246, respectively. As shown in FIG. 3B, each housing 210, 256, 257, 258 and 259 contains only one type of sorbent material. However, those skilled in the art will readily understand that more than one sorbent material can be present in any particular housing and that the number of housings can be reduced or increased, including the complete omission of a mixed bed de-I resin. Optionally, the sorbent cartridge 210 shown in FIG. 3B can have a mechanism for dividing the used dialysate 230 entering the sorbent cartridge between housing 256 and the deionization cartridge 210. As described above, a conductivity meter 101, 104 and/or 160 can control operation of a valve 212 that directs flow of the dialysate. Further, a valve 214 can be present to assist in controlling dialysate flow in addition to valve 212. In FIG. 2, effluent leaving deionization cartridge 210 is directed toward the sorbent cartridge 102, where the effluent contacts all of the sorbent materials present in cartridge 102. As shown in FIG. 3B, the effluent from deionization cartridge 210 can be directed to bypass one or more of the sorbent housings 256, 257, 258 and 259. Hence, the sorbent cartridge 102 can be designed to have two distinct flow paths for the conveyance of dialysate through the sorbent cartridge 102.

Figure 3C:
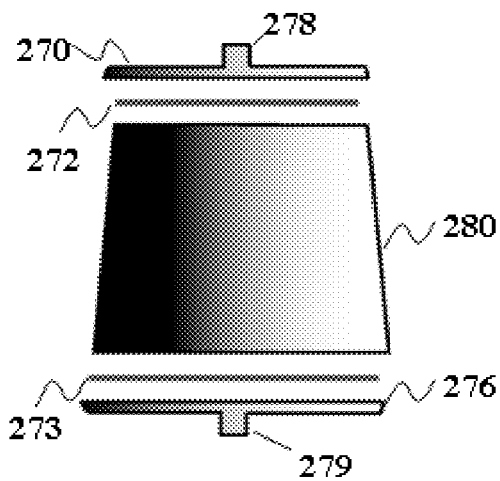

FIG. 3C shows a side view of one of the housings 210, 256, 257, 258 and 259. Each housing has a conical-shaped housing body 280, but can be formed in any suitable shape having a variable or fixed cross section that is substantially circular, rectangular, or triangular. The sorbent material is placed inside the housing body 280 and held in place and/or compressed by a top frit 272 and a bottom frit 273. The top of the housing body 280 is sealed with a top piece 270 that has an outlet port 278 for letting dialysate out of the housing body 280. The bottom of the housing body 280 is sealed with a bottom piece 276 that has an inlet port 279 for letting dialysate into the housing body 280. The housing body, bottom piece 276 and top piece 270 can have a notch 275 therein to facilitate the housing body 280 lying flush with the patient's body when worn.

Figure 3D:
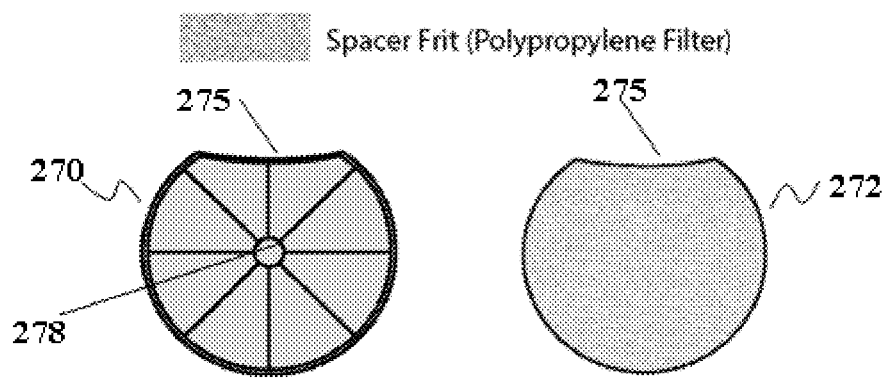
Figure 3E:
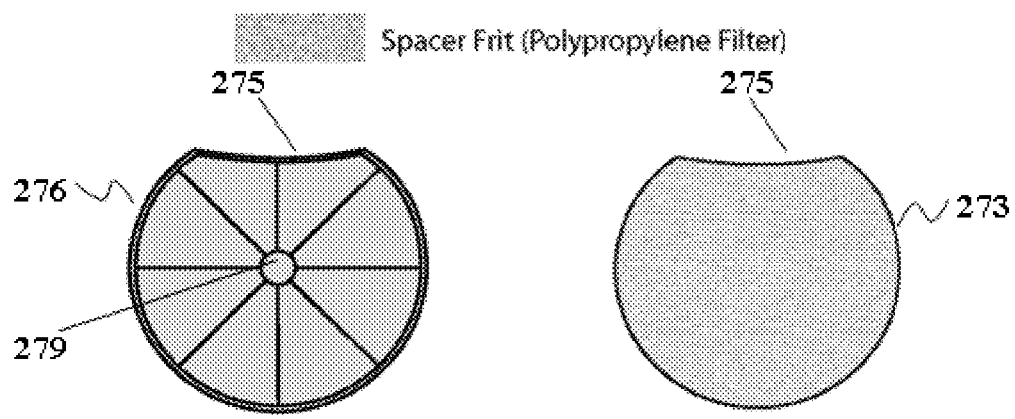

FIG. 3D shows a top view of the top piece 270 and the top frit 272. FIG. 3C shows a bottom view of the bottom piece 276 and the bottom frit 273. The top frit 272 and the bottom frit 276 can be made out of sintered glass or an inert plastic material, such as polypropylene. The top frit 272 and the bottom frit 276 serve to compress the contents of the housing body 280 as well as to prevent the escape of fines.

Figure 4A:
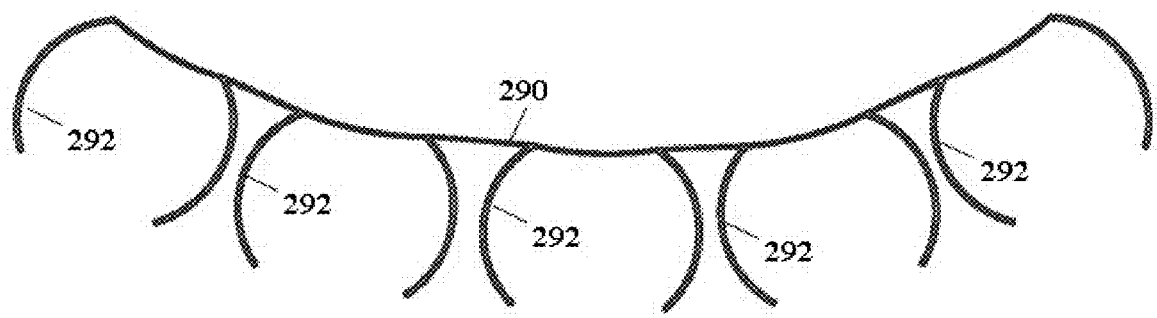
FIGS. 4A, 4B and 4C depict a sorbent cartridge with a carrier.
Figure 4B:
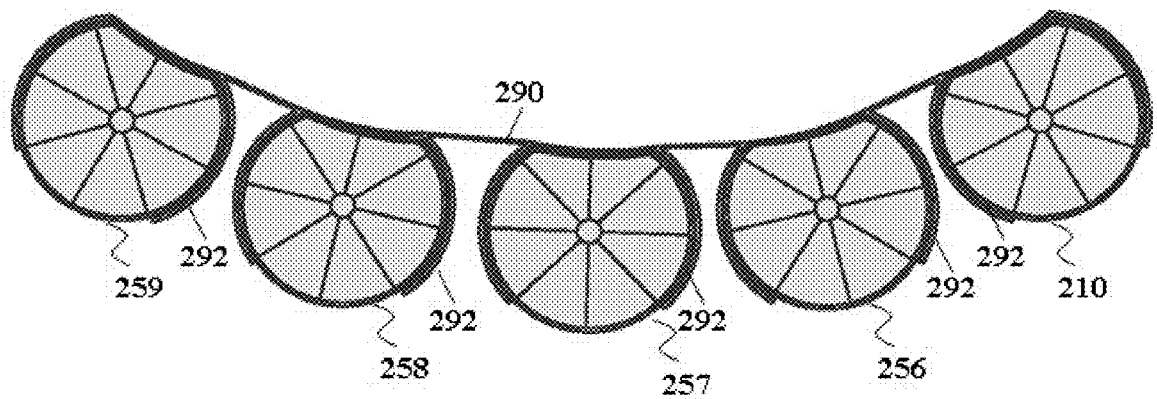

FIG. 4A shows a carrier 290 for organizing the individual sorbent housings 210, 256, 257, 258 and 259. The holder 290 has a plurality of arms 292 for holding the housings by compression arms. One of ordinary skill will understand that any other type of releasably fixing means known for holding the housings within the art is encompassed by the invention. FIG. 4B shows a top view of carrier 290 having sorbent housings 210, 256, 257, 258 and 259 placed therein.

Figure 4C:
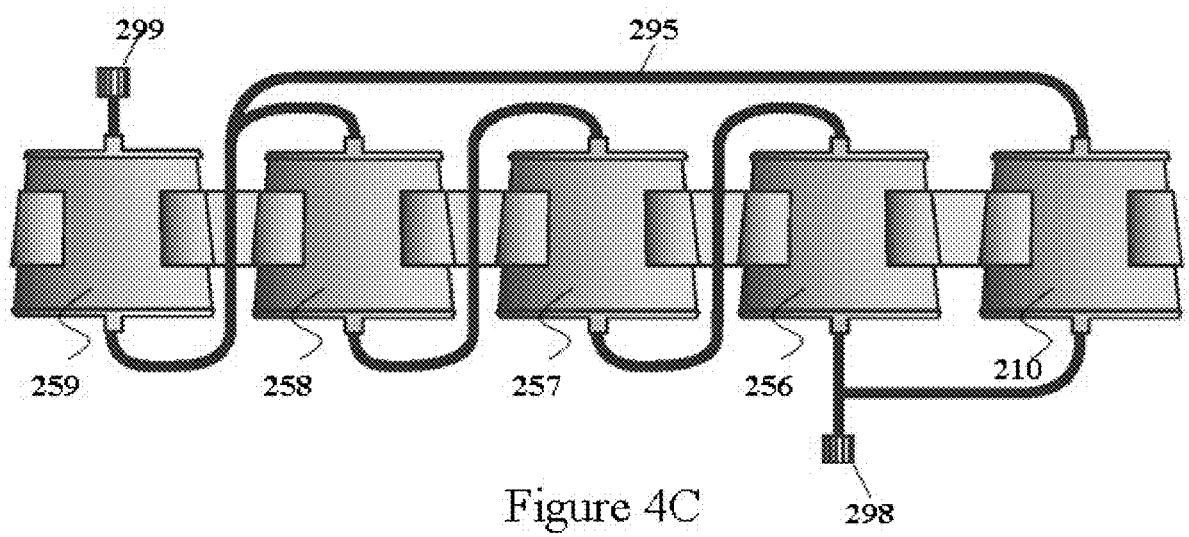

Further shown in FIG. 4C are housings 255, 256, 257, 258 and 259 arranged with connecting tubing 295. Keyed connectors 298 and 299 can be present to ensure that the sorbent cartridge 102 can only be incorporated into the dialysis circuit 141 in one orientation. As shown, fluid entering the sorbent cartridge is passed to either housing 256 having the urease-containing material or to housing/deionization cartridge 210 having the mixed bed de-I resin 255. Fluid leaving the housing 210 can be passed to the housing 259 having the activated carbon material 246 via connecting tubing 295 or flow conduits fashioned by attaching two molded pieces forming a fluid path(s). Fluid leaving the housing 256 is passed through the remaining housings.

Figure 5:
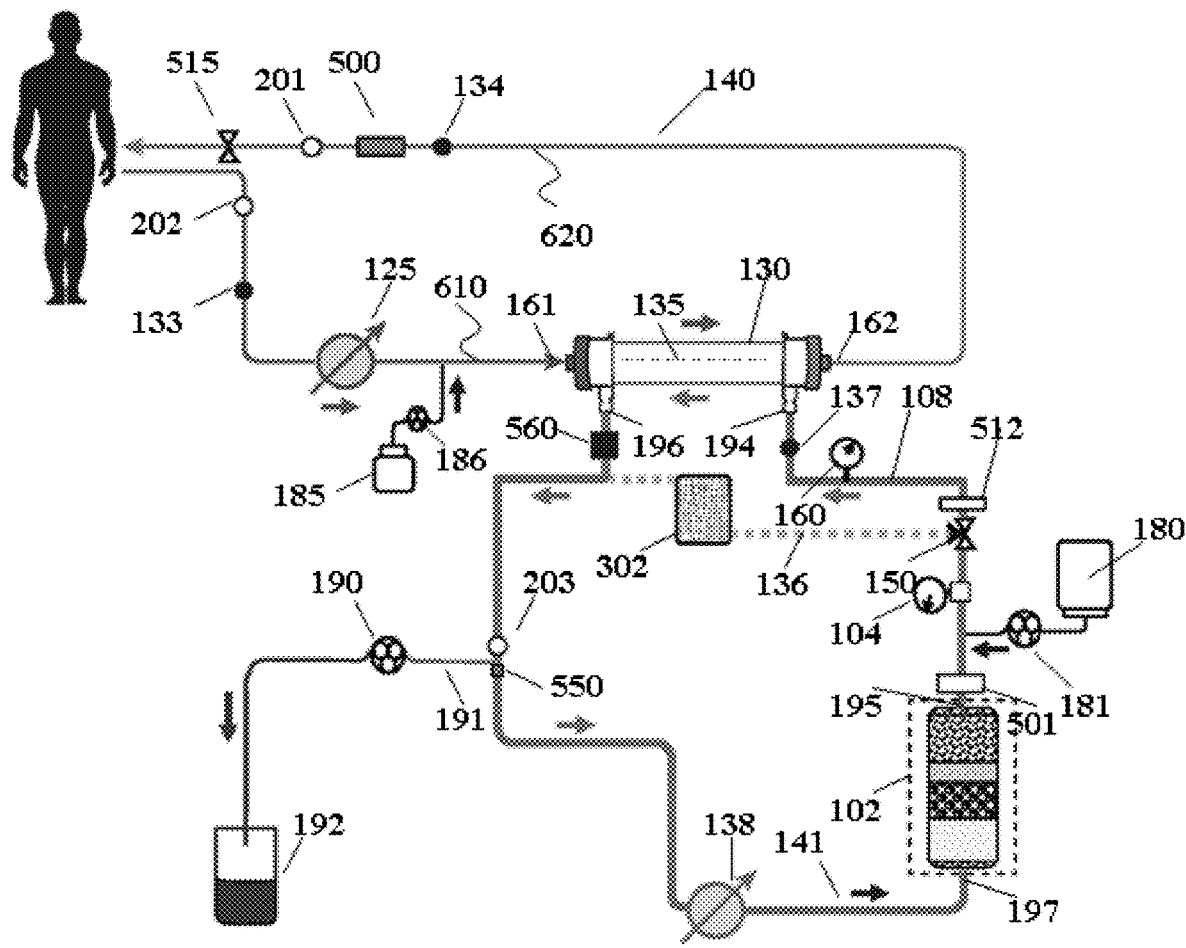
FIG. 5 shows a hemodialysis device having a controlled compliant dialysis circuit and a bicarbonate cartridge operating in accordance with certain embodiments.

The zirconium oxide and zirconium phosphate materials, as well as the optional mixed bed de-I resin, remove substantially all of the $Mg^{2+}$, $Ca^{2+}$, and $K^+$ cations from the dialysate exiting the sorbent cartridge. Hence, a concentrated infusate solution of the relevant cations is added by an infusate pump 181 from an infusate reservoir 180 as shown in FIG. 5. Since the concentrations of $Mg^{2+}$, $Ca^{2+}$, and $K^+$ in the dialysate are desired to be near physiological levels, the concentration of such cations are not largely affected during kidney replacement therapy. In certain embodiments, the infusate solution can be added to the dialysate at a constant or near constant rate during treatment. The addition of the infusate pump 181 is under the control of a controller 801 and the rate of the infusate pump can be modified during treatment.

Due to the nature of the controlled compliance dialysis circuit, the volume of the infusate solution added by the infusate pump 181 drives the flux of the same volume of fluid from the dialysis circuit into the extracorporeal circuit 140. The controller 801 that controls the control pump 190 operates at a rate that compensates for the fluid volume added by the infusate pump. For example, if the infusate pump 181 adds the infusate solution at a rate of 0.5 mL/min, then the control pump 190 will operate at an efflux rate of 0.5 mL/min in order to maintain a net zero flux of fluid exchange between the dialysis circuit and the extracorporeal circuit 140. If, however, the system operates to remove 2 mL/min of fluid from the extracorporeal circuit, then the control will send instructions to the control pump 190 to operate at an efflux rate of 2.5 mL/min to compensate for the fluid volume being added by the infusate pump at a rate of 0.5 mL/min. The operation of the control pump 190 can be modified to adjust for any fluid volume being added by the infusate pump 181 in order to achieve a control flux of fluid between the dialysis circuit and the extracorporeal circuit.

Control of pH

Constant pH in the blood is maintained by the presence of bicarbonate which is equilibrated with $CO_2$ through the action of carbonic anhydrase. Systems employing a sorbent cartridge 102 have a tendency to induce mild acidosis, particularly toward the beginning of treatment, due to adsorption of bicarbonate by the sorbent cartridge 102, where bicarbonate freely diffuses across the dialysis membrane. After the initial loss of bicarbonate to the sorbent cartridge, the sorbent cartridge will add bicarbonate to the dialysate due to hydrogen ion added to the dialysate in exchange for ammonium carbonate.

In certain embodiments, a bicarbonate cartridge containing sodium bicarbonate or another bicarbonate-containing salt can be provided within the system, where dialysate solution can be diverted through the bicarbonate cartridge as required. As shown in FIG. 5, the bicarbonate cartridge 302 is present in the second bypass pathway 136 attached to 3-way valve 150, wherein a portion of the dialysate flow can bypass the dialyzer 130 and be passed through the bicarbonate cartridge 302. The bicarbonate cartridge 302 can contain an amount of solid sodium bicarbonate or another bicarbonate-containing salt that is reconstituted to form a saturating solution during a priming cycle, as described below. Changing the state of the 3-way valve 150 will direct flow to the bicarbonate cartridge 302 to release bicarbonate into the system. Dialysate flow can be diverted through the bicarbonate cartridge 302 as needed to adjust the pH of the dialysate. Further, the bicarbonate cartridge 302 at the beginning of treatment can be used to preload the sorbent cartridge 102 so that the bicarbonate level will not significantly decrease at the beginning of treatment due to absorption of bicarbonate ions by the sorbent cartridge 102. In certain other embodiments, the contents of the bicarbonate cartridge 302 is completely dissolved in the priming process rather than forming a saturated solution. The dissolved bicarbonate can then preload the sorbent cartridge 102 at the beginning of treatment to prevent an excessive drop in pH at the beginning of treatment.

In certain other embodiments, a bicarbonate containing solution can be added via a bicarbonate pump 505, as shown in FIG. 1A. In FIG. 1A, a bag or container 504 containing sodium bicarbonate is attached to the system via a pump 505. The bag or container 504 can contain a premeasured solid amount of sodium bicarbonate that is reconstituted during the priming process by running the pump 505 in reverse. Alternatively, a premade bicarbonate solution can be provided. Bicarbonate infusion is controlled by the pump 505 to maintain a constant and physiological pH in the system. Adjustment of pH using pump 505 is also shown for the hemofiltration system in FIG. 1B.

Figure 6:
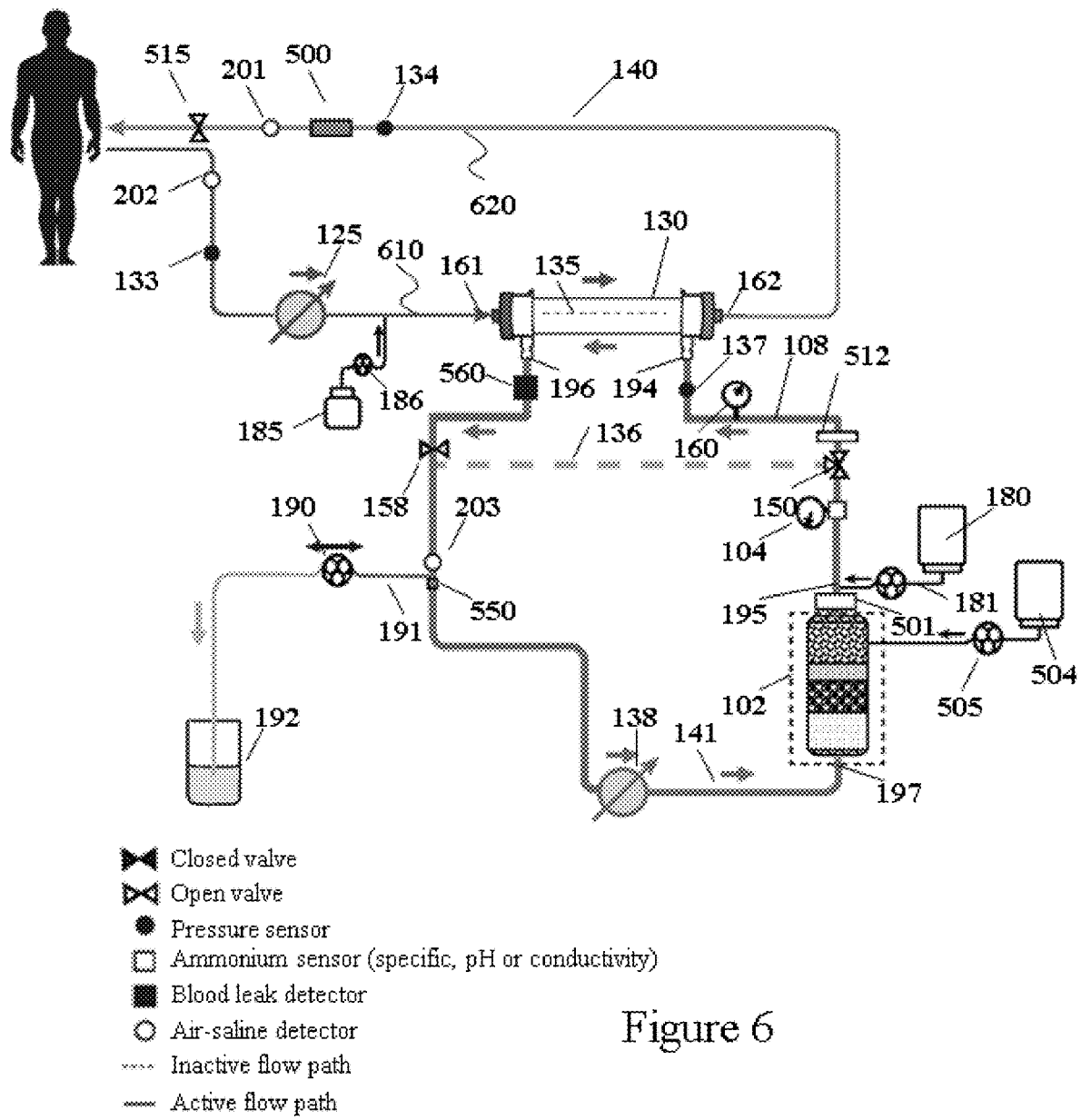
FIG. 6 shows a hemodialysis device having a controlled compliant dialysis circuit and a bicarbonate infusion pump operating in accordance with certain embodiments.
Figure 7:
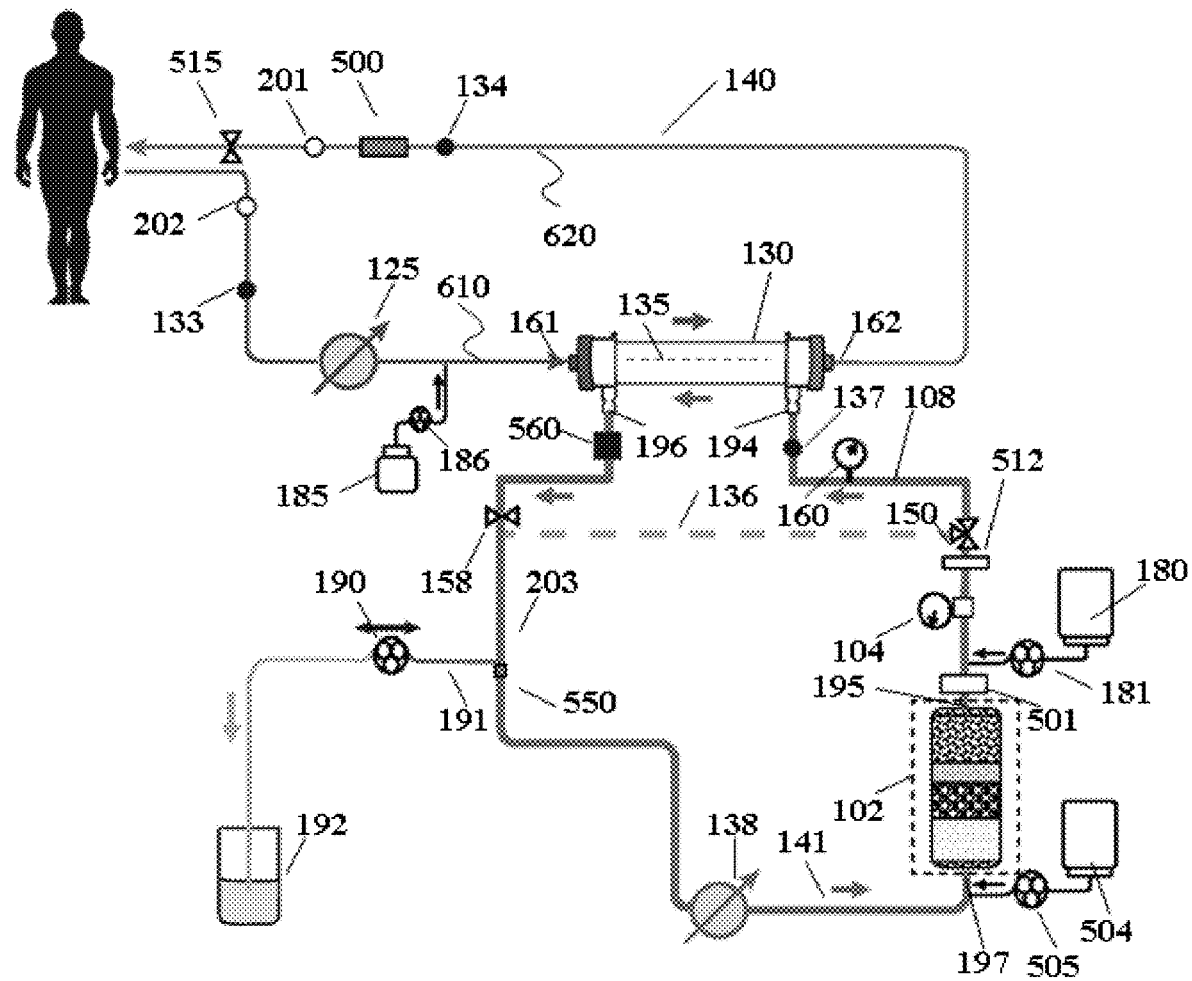
FIG. 7 shows a hemodialysis device having a controlled compliant dialysis circuit and a bicarbonate infusion pump operating in accordance with certain embodiments.

FIGS. 6 and 7 show alternate embodiments for the location of the bicarbonate pump 505. As shown in FIG. 6, the pump 505 can be used to introduce bicarbonate into a side port of the sorbent cartridge 102. Preferably, the bicarbonate solution is introduced at a point after the zirconium phosphate and zirconium oxide materials. Bicarbonate ion can form insoluble salts in the presence of $Mg^{2+}$ and $Ca^{2+}$ ions. Therefore, pH may be more adequately controlled when added at a location where cations have been removed by action of the zirconium phosphate material, and $Mg^{2+}$ and $Ca^{2+}$ ions have not yet been infused into the dialysate. As shown in FIG. 7, certain embodiments can have the pump 505 positioned to deliver bicarbonate ions to spent dialysate prior to entering the sorbent cartridge 102.

The rate of addition of bicarbonate ions to the dialysis circuit 141 can be at a constant rate over the course of treatment in accordance with some embodiments. In certain embodiments, a pH meter can be located within the system to measure the pH of the dialysate within the dialysis circuit 141, where a controller 801 monitoring the pH meter can make appropriate adjustment to the rate of bicarbonate addition to the dialysis circuit 141. Since bicarbonate solutions are conductive, the pH meter may be replaced by a conductivity sensor. As will be described below, certain embodiments allow for the amount of urea absorbed by the sorbent cartridge 102 to be quantified by a controller 801. In certain embodiments, the controller 801 can adjust the rate of bicarbonate addition to the dialysis circuit 141 based up the amount of urea calculated to be absorbed by the sorbent cartridge 102, where there is no requirement for the pH of the dialysate to be directly measured.

Priming of the Portable Kidney Replacement System

The systems and methods described herein are designed for home use outside of a clinical setting with trained medical staff. Further, many users of kidney replacement therapy are in poor health and may have limited vision and manual dexterity due to disease or age. Since dialysis systems require preparation prior to use, set-up can be difficult for some patients. Further, the system has to be properly purged of air (i.e. primed) prior to use such that the various pumps function properly and to protect the patient from an air embolism. In certain embodiments, the systems described herein can be primed and prepared for operation through the provision of only one fluid provided in a single container. This "one-fluid" priming feature is enabled by the nature of the controlled compliance dialysis circuit 141 and the ability to accurately control the movement of fluid between the extracorporeal circuit 140 and the dialysis circuit 141 due to the controlled compliance nature of the dialysis circuit 141.

In certain embodiments, the systems described herein have quick connectors, such as luer connectors, that are large and operable with little force or dexterity. With reference to FIGS. 8 through 12, methods for priming the hemodialysis systems disclosed herein will be described. Reference numbers in FIGS. 8 through 12 equate to like elements in FIG. 1A. Solid-lined areas in the extracorporeal circuit 140 or the dialysis circuit 141 refer to areas containing fluid (e.g. blood, saline, water, etc.) undergoing active flow or conveyance during a stage of priming the hemodialysis system with the direction of movement indicated by arrows. Dashed-line areas indicate areas in the extracorporeal circuit 140 or the dialysis circuit 141 containing air or a non-moving fluid during a stage of priming. Valves are shown as "bowtie-shaped" symbols, where closed valves are shaded and open valves are unshaded.

Figure 8:
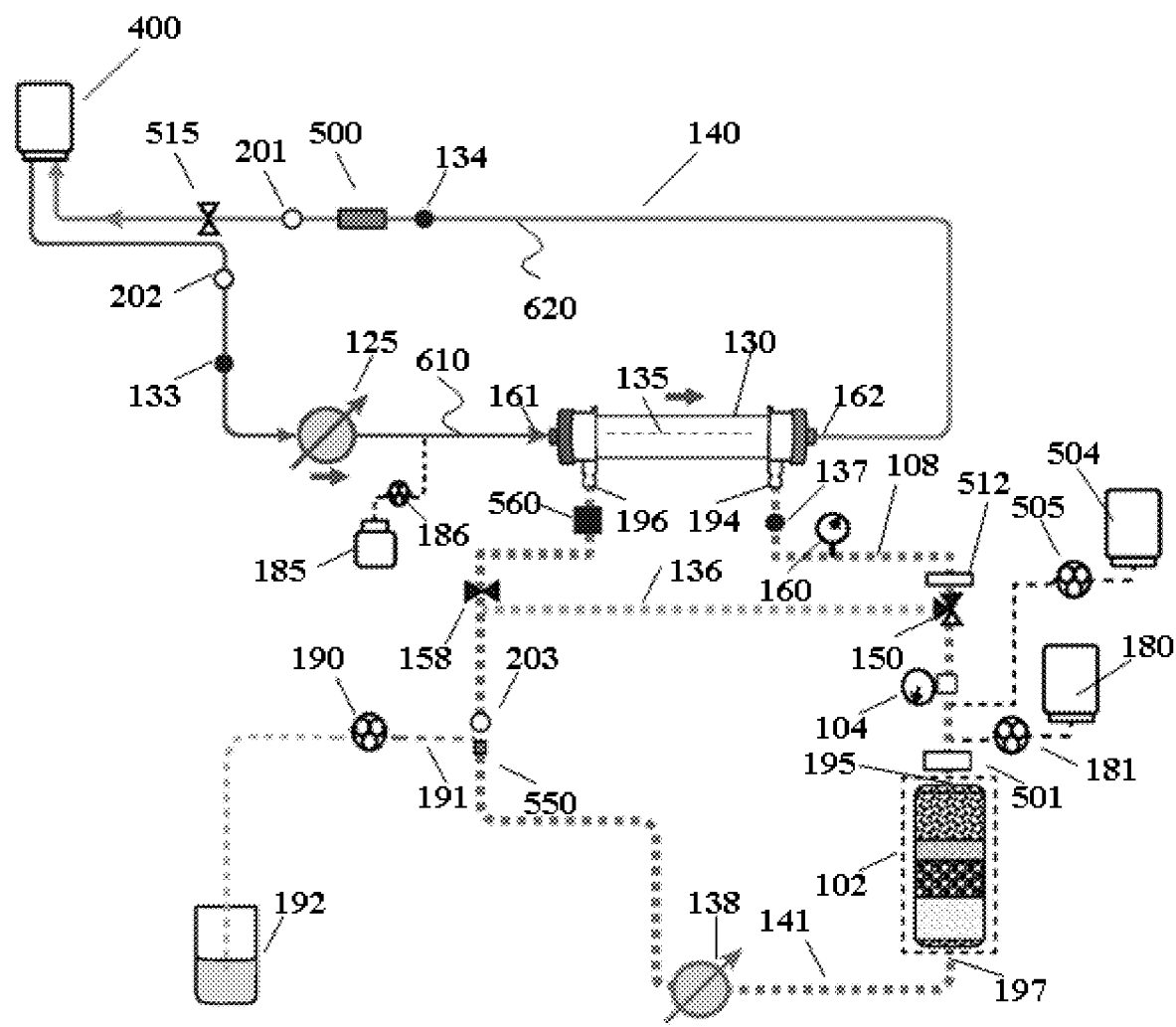
FIG. 8 shows a hemodialysis device having a controlled compliant dialysis circuit undergoing a priming operation to remove air from the extracorporeal circuit.

With reference to FIG. 8, a single source of saline 400 can be attached to the extracorporeal circuit 140 to provide fluid to prime the system. The manner in which the saline 400 is attached to the extracorporeal circuit 140 is not particularly limiting. In certain embodiments, quick connectors located on the extracorporeal circuit 140 can incorporate spikes that can be used to puncture the saline container 400, or quick connectors can be attachable to other luer adapters and tubing that lead to the saline container 400. The same quick connectors can be used to attach to the shunt for accessing a patient's vascular system.

In certain embodiments, the extracorporeal circuit 140 and the dialyzer 130 are provided sterile. After the saline container 400 is attached to the extracorporeal circuit 140, the first step in priming the system is to flush the extracorporeal circuit 140, including the extracorporeal side of the dialyzer 130 with the saline solution. This is accomplished by running the blood pump 125 until all of the air is pushed out of the extracorporeal circuit 140, as shown in FIG. 8. The saline container 400 can contain from about 250 to 1000 mL of saline solution; however, the volume of saline provided is not limited to any particular amount. Saline or another priming fluid is circulated in the extracorporeal circuit 140 until there is no indication of air in the extracorporeal circuit 140 as indicated by air-fluid detectors 201 and 202. Valves 158 and 150 are kept in a closed position that prevents saline for accessing the dialysis circuit 141. The saline container 400 can be placed higher than the extracorporeal circuit 140 flow path such that hydrostatic pressure is provided in addition to the blood pump 125 and to facilitate the removal of air.

Figure 9:
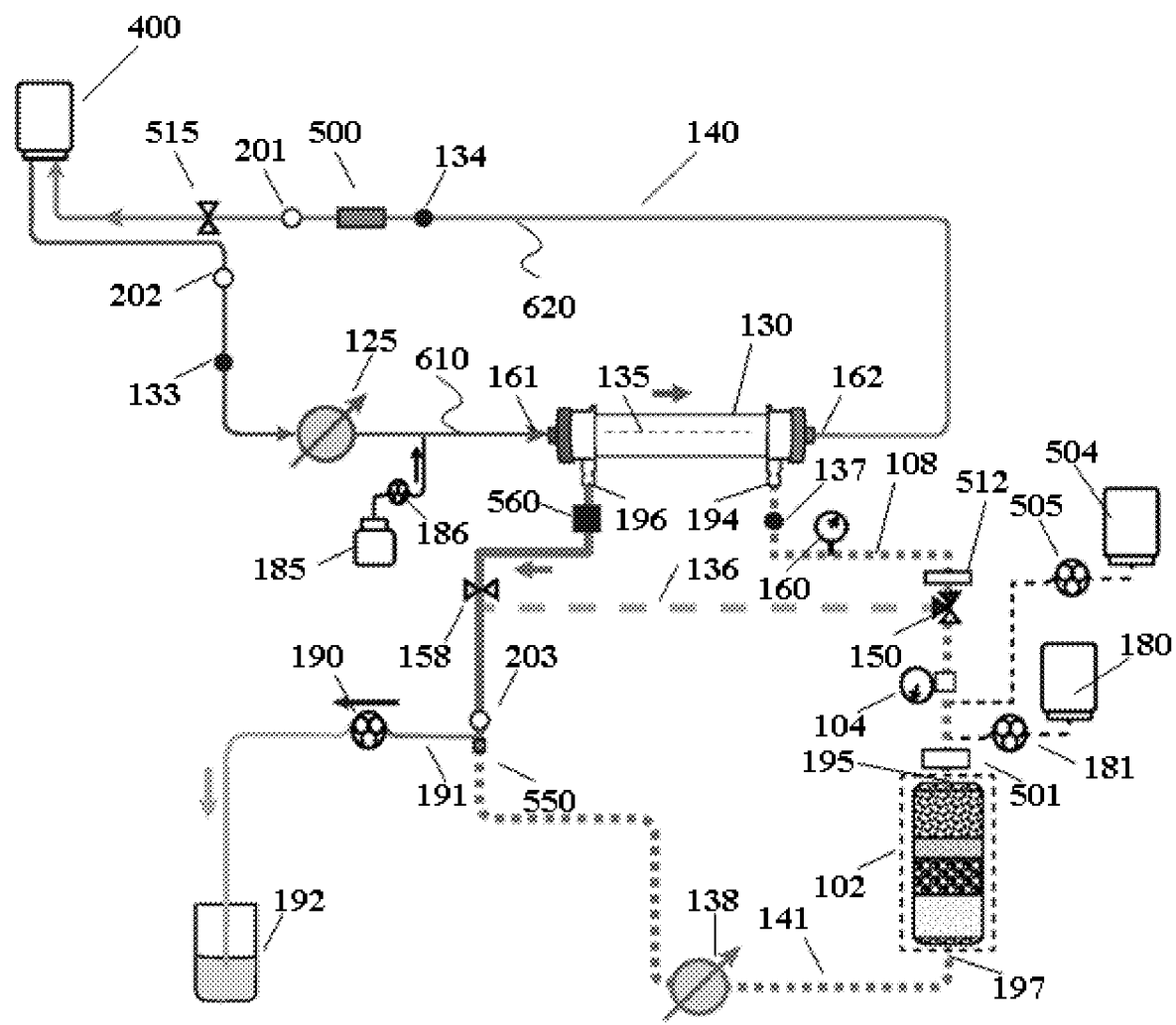
FIG. 9 shows a hemodialysis device having a controlled compliant dialysis circuit undergoing a priming operation to remove air from a portion of the dialysis circuit.

With reference to FIG. 9, after the extracorporeal circuit 140 is free from air, the dialysis circuit 141 is primed. Valve 158 is placed in an open position allowing for flow from the dialyzer 130 to access the dialysis circuit 141; valve 150 is kept in a closed position. The control pump 190 is run in an efflux direction to pull saline solution across the dialysis membrane 135, into the portion of the dialysis circuit 141 shown in solid lines. Air from the dialysis circuit 141 is vented into the control reservoir 192. Air-fluid detector 203 is located in the vicinity of the union of the dialysis circuit 141 and the control pump conduit 191. The control pump 190 is operated in the efflux direction until air-fluid detector 203 indicates that air and bubbles are removed.

Figure 10:
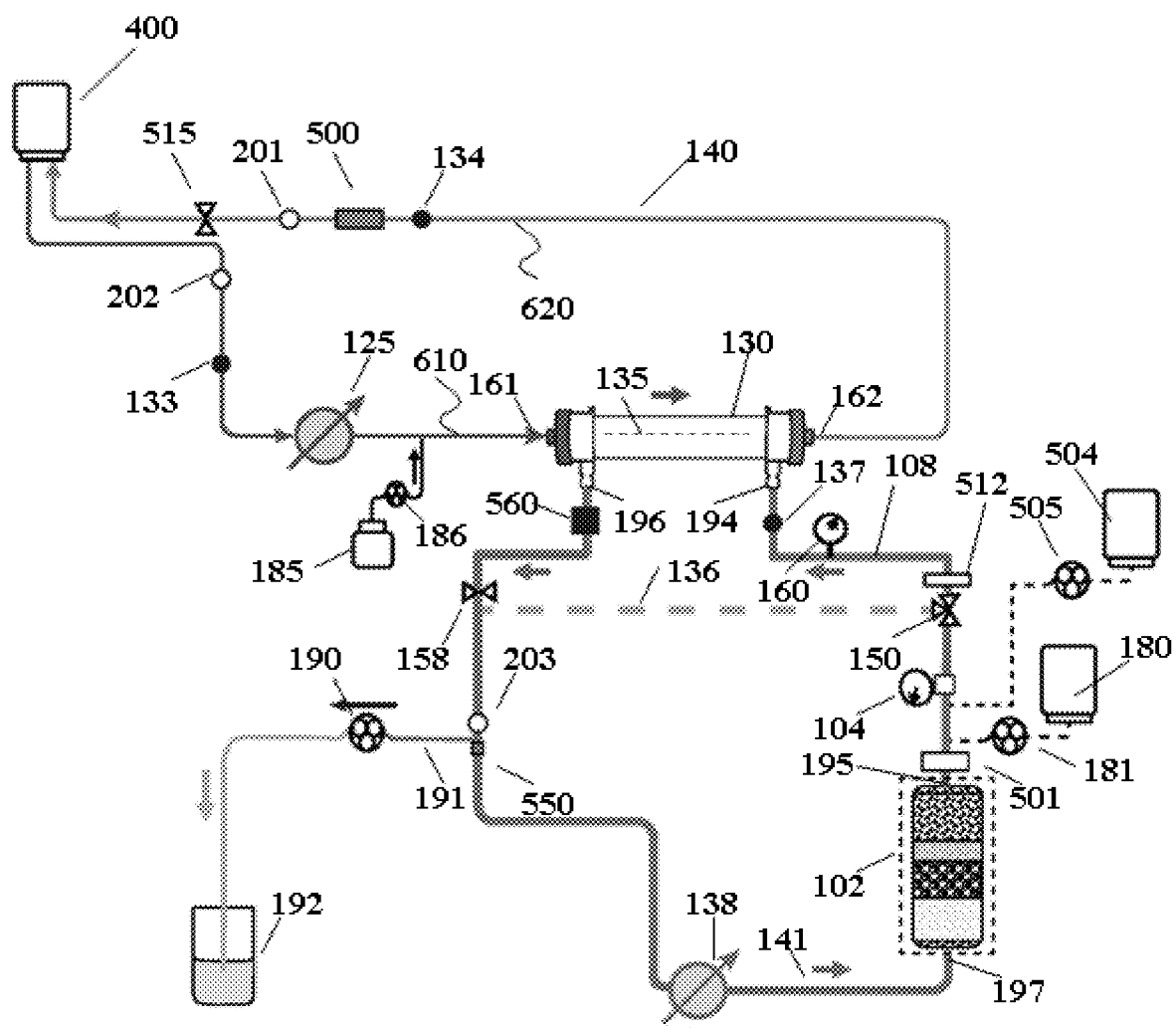
FIG. 10 shows a hemodialysis device having a controlled compliant dialysis circuit undergoing a priming operation to remove air from the dialysis circuit.

With reference to FIG. 10, valves 158 and 150 are both placed in an open position to allow access to the dialysis circuit 141 after air is cleared from air-fluid detector 203. The dialysate pump 138 is run to circulate the saline through the dialysis circuit 141, where additional saline solution is pulled across the dialysis membrane 135. During priming of the dialysis circuit 141 as shown in FIG. 10, the control pump 190 is occasionally operated to remove or vent air from the dialysis circuit 141 that is being displaced by saline solution. In certain embodiments, the control pump 190 is operated in the efflux direction whenever air is detected at air-fluid detector 203. The three-way valve 150 is occasionally operated to direct saline flow through the through the second bypass pathway 136 to accomplish priming of the second bypass pathway 136. Similarly, if an in-series deionization cartridge 210 is present (not shown in FIG. 10), then valve 212 can be opened intermittently to prime the deionization cartridge 210 and tubing associated therewith.

Figure 11:
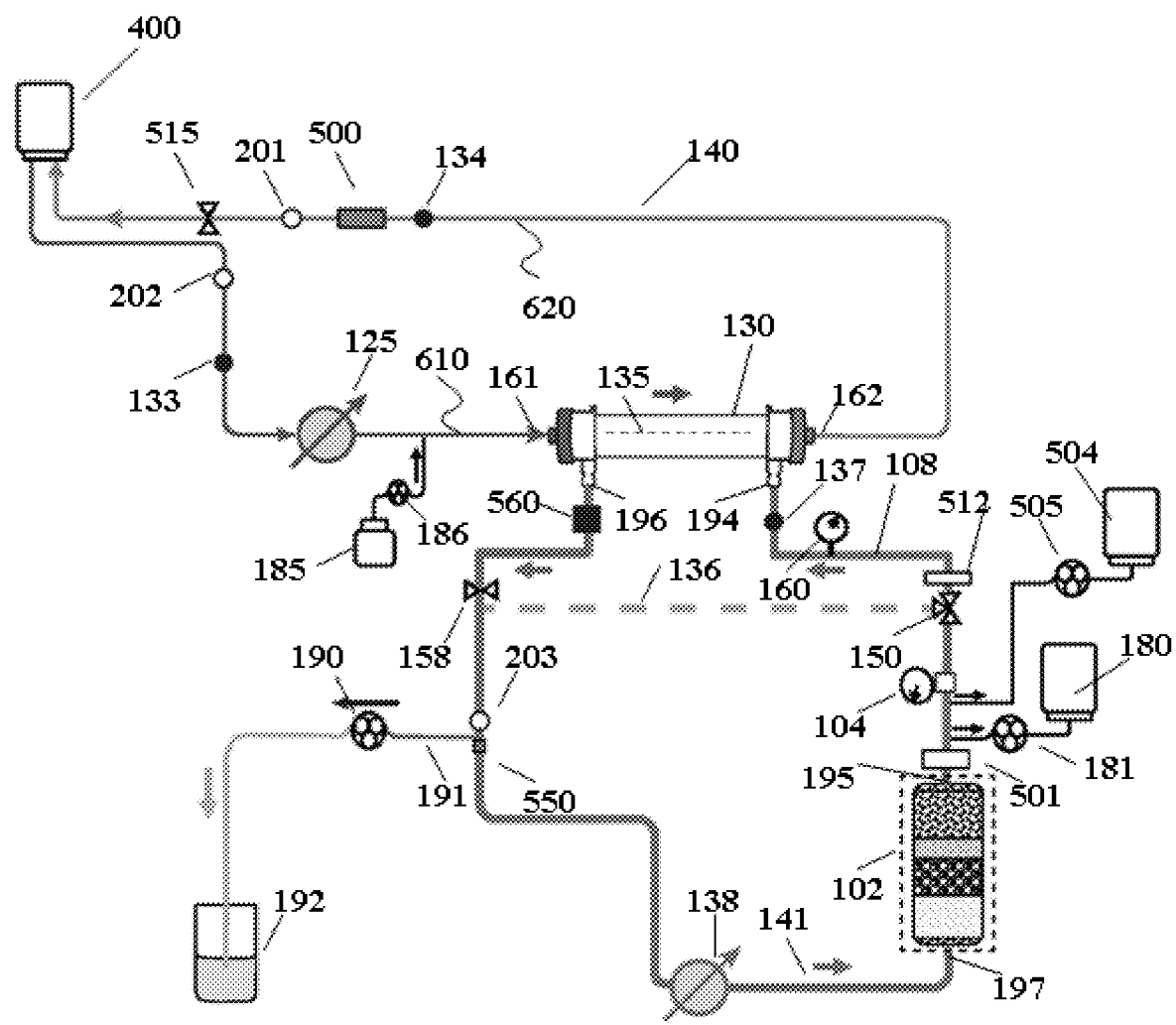
FIG. 11 shows a hemodialysis device having a controlled compliant dialysis circuit undergoing a priming operation to remove air from the dialysis circuit and reconstitute infusate salts.

After air is removed from the dialysis circuit 141, the saline solution can be used to reconstitute a bicarbonate salt and/or infusate salts containing $Ca^{2+}$, $mg^{2+}$, and $K^+$, ions that can be provided in solid form. As shown in FIG. 11, the bicarbonate pump 505 and the infusate pump 181 can be run in a "reverse" direction to drawn saline solution from the dialysis circuit 141 into the bicarbonate reservoir 504 and the infusate reservoir 180, respectively. Pumps 505 and 181 can be used to meter a predetermined volume of saline solution into the bicarbonate reservoir 504 and the infusate reservoir 180, respectively, such that the formed bicarbonate and infusion solutions have a known concentration.

Figure 12:
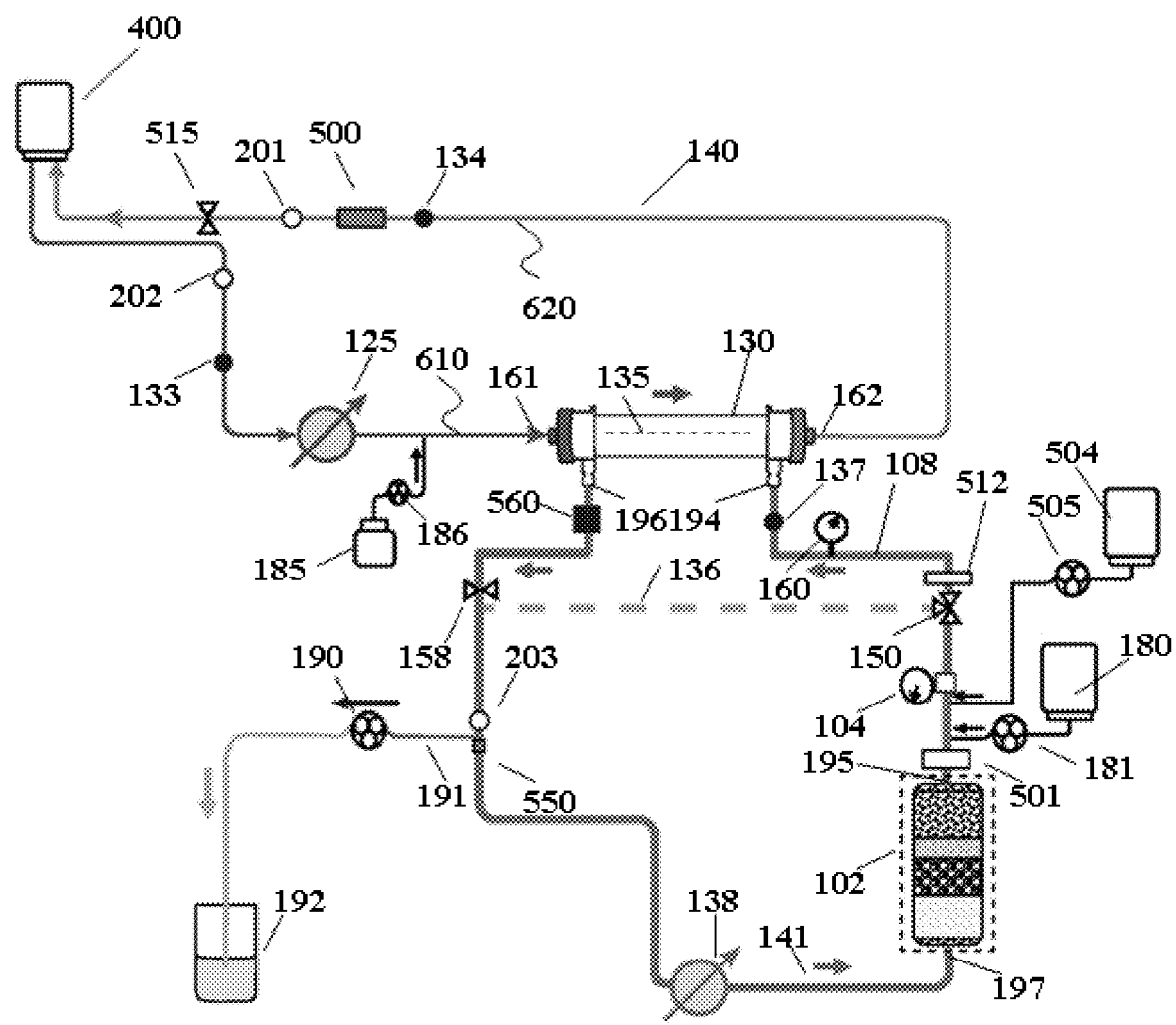
FIG. 12 shows a hemodialysis device having a controlled compliant dialysis circuit undergoing a priming operation to remove air from the dialysis circuit and to adjust the composition of the dialysate.

Prior to readying the system for hemodialysis, the saline solution in the now primed system is to be modified to have an appropriate composition to serve as a dialysate. As shown in FIG. 12, the infusate pump 505 and the bicarbonate pump 181 are run in their normal operating direction while the solution within the dialysate circuit 141 is circulated to adjust the cation (e.g. $Ca^{2+}$, $Mg^{2+}$, $K^+$, etc.) concentration and the pH to form a functional dialysate. After the priming process is complete, the extracorporeal circuit 140 can be connected to the vasculature of the patient and treatment commenced. If the patient does not attach to the extracorporeal circuit 140 within a brief, predetermined period of time, the dialysate pump 138 can be stopped to prevent the consumption of zirconium phosphate within the sorbent cartridge 102 due to absorption of cations from the dialysate. In certain embodiments, the dialysis circuit 141 can include a bypass around the sorbent cartridge in order to preserve the zirconium phosphate therein during priming.

Figure 13:
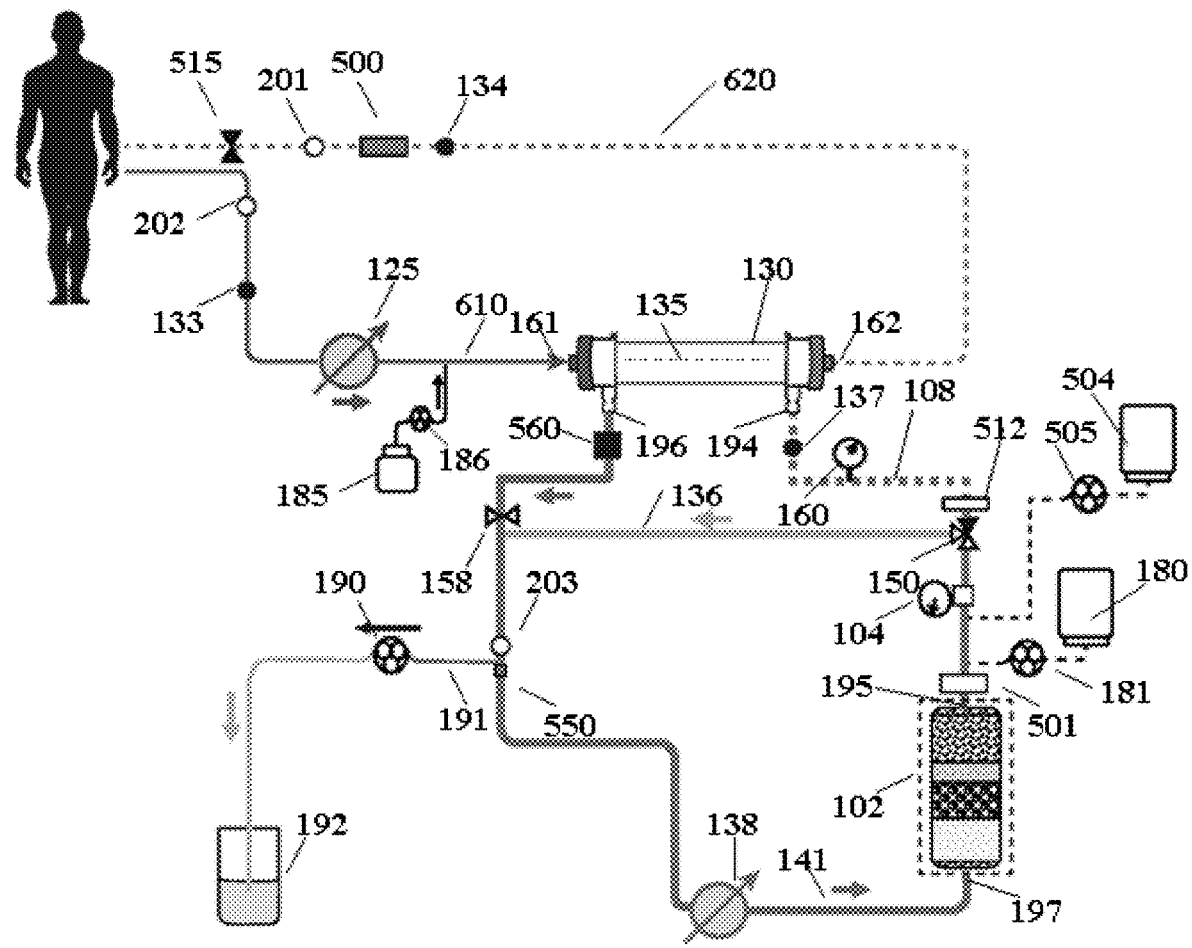
FIG. 13 shows a hemodialysis device having a controlled compliant dialysis circuit undergoing a priming operation to displace a priming fluid from an extracorporeal circuit to the dialysis circuit with blood from a patient.
Figure 14:
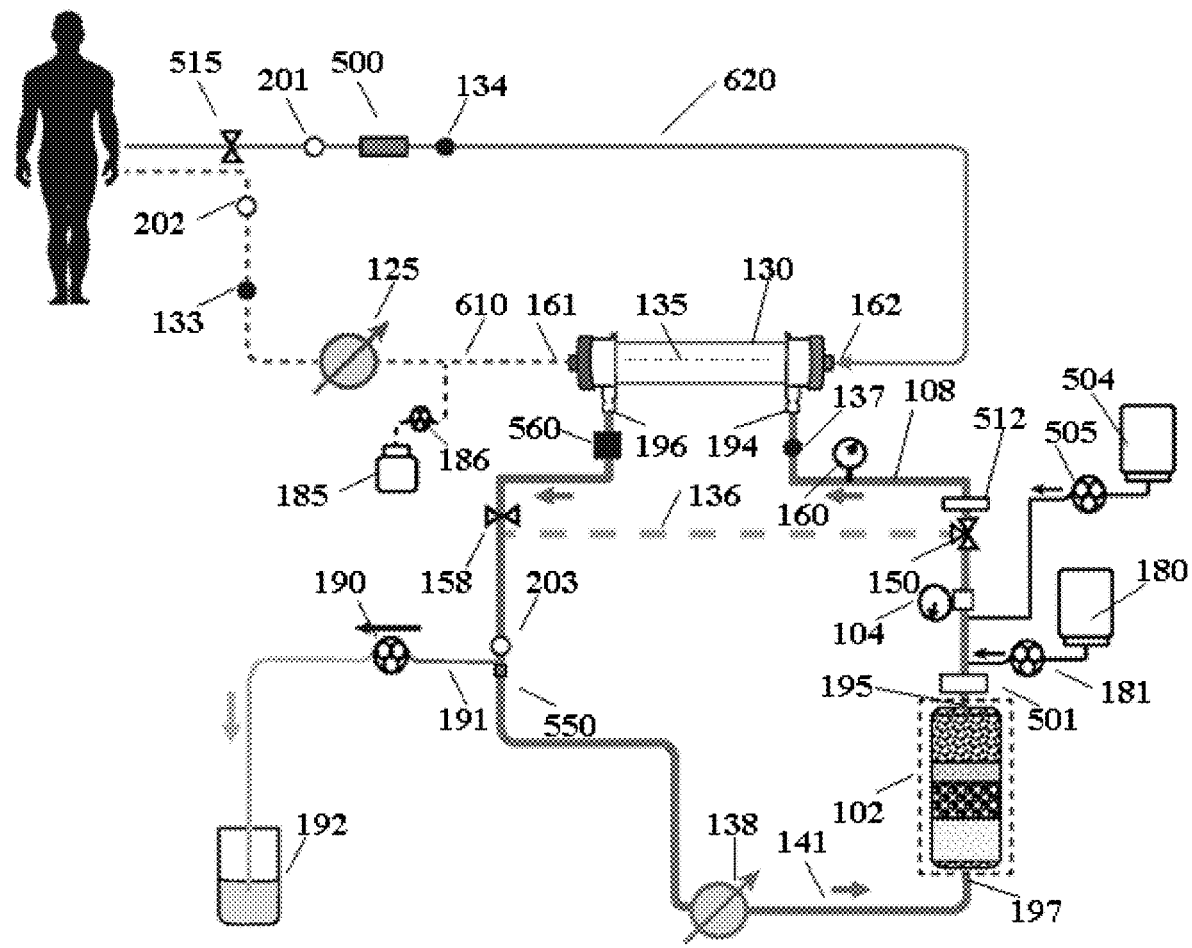
FIG. 14 shows a hemodialysis device having a controlled compliant dialysis circuit undergoing a priming operation to displace a priming fluid from an extracorporeal circuit to the dialysis circuit with blood from a patient.
Figure 15:
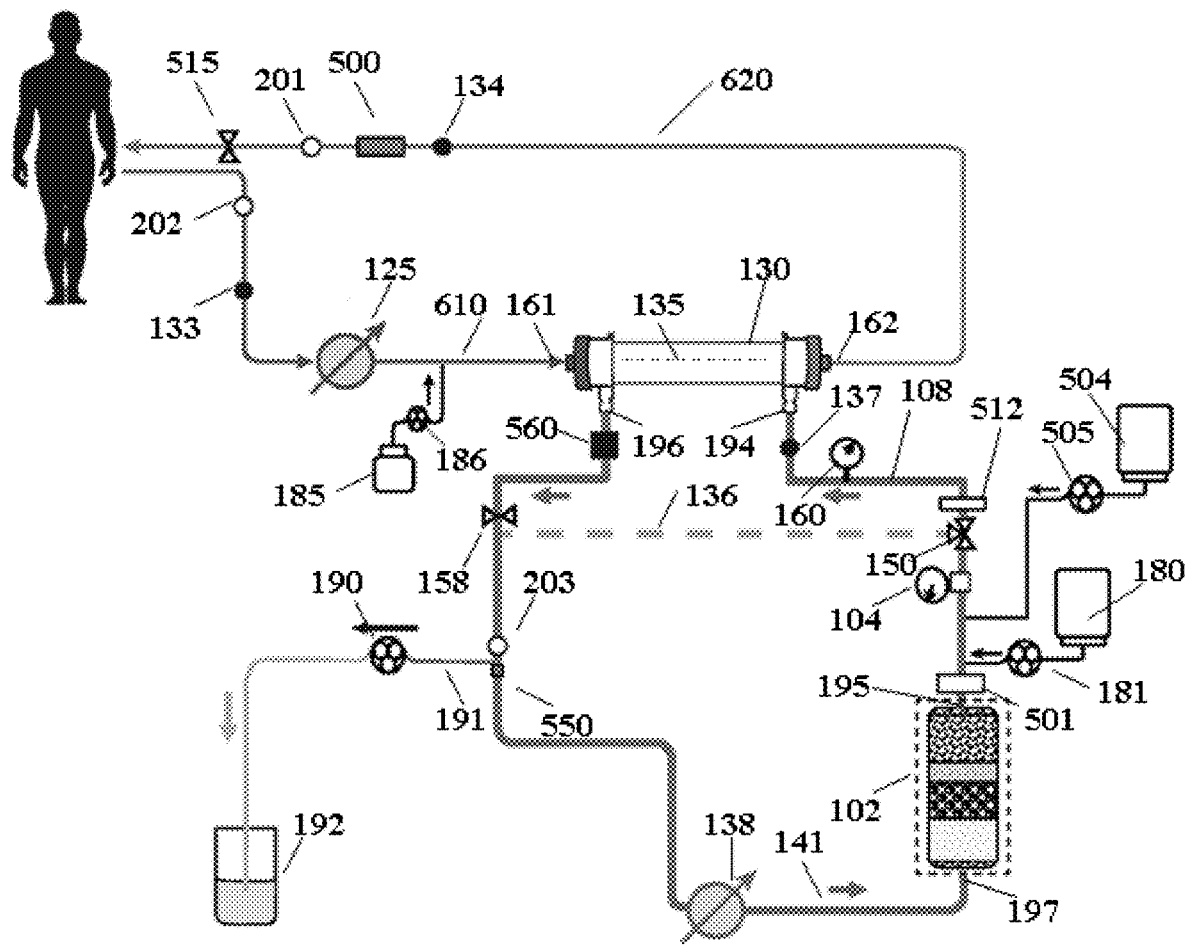
FIG. 15 shows a hemodialysis device having a controlled compliant dialysis circuit and an extracorporeal circuit undergoing a priming operation to fill a void volume in the dialysis circuit with fluid originating from a patient's blood.

The process to prime the system described in FIGS. 8 through 12 necessitates that the saline solution or other priming fluid used to prime the extracorporeal circuit 140 is introduced into the patient at the beginning of the treatment. With reference to FIGS. 13 through 15, a priming method having the advantages of requiring only one priming solution and avoiding introduction of the priming solution to the patient will be described.

The extracorporeal circuit 140 is attached to a saline container 400 and flushed with saline solution as described above in FIG. 8. Optionally, the control pump 190 can be operated in the efflux direction to draw saline solution into a portion of the extracorporeal circuit as described in FIG. 9. After flushing of the extracorporeal circuit 140 with saline solution, the saline container 400 is removed and the extracorporeal circuit 140 is attached to patient's vascular system, as shown in FIG. 13. Normally, all pumps within the system are stopped during the period when connections are made between the subject and the extracorporeal circuit 140 and valve 515 is placed in a closed position to prevent unpriming of the system.

During normal operation of the system to perform kidney replacement therapy, the blood and the dialysate are passed through the dialyzer 130 in opposite directions. The portion of the extracorporeal circuit 140 between the subject and the dialyzer 130 can be referred to as the arterial line 610 that carries blood from the patient to the dialyzer 130 during normal operation. The portion of the extracorporeal circuit 140 between the dialyzer 130 and the subject can be referred to as the venous line 620 that returns blood to the patient. Once the patient is connected to the extracorporeal circuit 140 and the extracorporeal circuit 140 is flush with saline, the dialysate pump 138 and the blood pump 125 are run at the same rate with valve 158 in the open position. As a result, blood is drawn into the venous line 610 to the dialyzer 130 and the saline solution that was present in the venous line 610 is transferred to the dialysate circuit 141, as shown in FIG. 13. The valve 150 is kept in a position to direct flow through the second bypass pathway 136 to avoid pushing air into the dialyzer 130.

At the time that blood fills the arterial line 610, the blood pump 125 is turned off and the dialysate pump 138 and the control pump 190 are run to draw blood into the venous line 620. Control pump 190 is run in the efflux direction to provide an outlet for air in the system. In certain embodiments, the control pump 190 can be run when air is detected at air-fluid detector 203. As shown in FIG. 14, the location of the stopped blood pump 125 in the arterial line 610 acts as a valve that prevents the passage of blood in either direction. Valve 515 is placed in an open position to allow blood to be drawn into the venous line 620 by action of the dialysate pump 138 and the control pump 190. At the same time, the saline solution that was present in the venous line 620 is transferred to the dialysis circuit 141. Valve 150 is kept in a position to direct flow through the bypass loop 136 to prevent contact or reintroduction of saline into the dialyzer 130 until conductivity is adjusted to a safe level. The bicarbonate pump 505 and the infusate pump 181 are run to adjust the composition of the fluid within the dialysis circuit 141. When the dialysate composition is within an acceptable range, the valve 150 can be adjusted to allow flushing of the dialysis circuit 141 between the valve 150 and the dialyzer 130 with dialysate.

At the time that the extracorporeal circuit 140 is filled with blood, the entire volume of saline has been transferred from the extracorporeal circuit 140 to the dialysis circuit 141. The volume of the dialysis circuit 141 is typically larger than the volume of the extracorporeal circuit 140. In certain embodiments, the volume of the dialysis circuit 141 can be from about 100 mL to about 200 mL larger than the extracorporeal circuit 140. To fill the remaining volume of the dialysis circuit 141 and complete the priming process, blood is circulated through the extracorporeal circuit 140 through operation of the blood pump 125 and an anticoagulant is added to the blood from the container 185 by means of the anticoagulant pump 186, as shown in FIG. 15. In the event that the dialysis circuit 141 is not completely primed, the action of the dialysate pump 138 will draw fluid from the blood plasma into the dialysis circuit 141 by ultrafiltration across the dialysis membrane 135. In certain embodiments, the dialysis pump 138 is slowed down to operate at a rate less than the rate of the blood pump 125. In certain embodiments, the dialysis pump is run at a rate that is no more than about 66% of the rate of the blood pump 125. Running at a lower rate, the dialysate pump 138 draws fluid volume from the extracorporeal circuit 140, such fluid volume originating from the patient's blood, to fill the remaining volume of the dialysis circuit 141. The volume of fluid removed from the extracorporeal circuit 140 can be calculated by a controller 801 and taken into account for quantifying the total volume of fluid removed from the patient over the course of treatment. When the system is fully primed, the control pump 190 can then be used to control the flux of fluid between the extracorporeal 140 and the dialysate circuits 141.

As indicated above, the above-described priming operation has several benefits. The patient does not need to connect and disconnect a priming fluid source other than the saline container 400. Further, the initial saline prime is not given to the patient. A controller 801 is able to account for the volume of fluid removed from the patient (i.e. from extracorporeal circuit 140) needed to complete priming of the dialysis circuit and to incorporate such volume into fluid removal or addition calculations.

Figure 16:
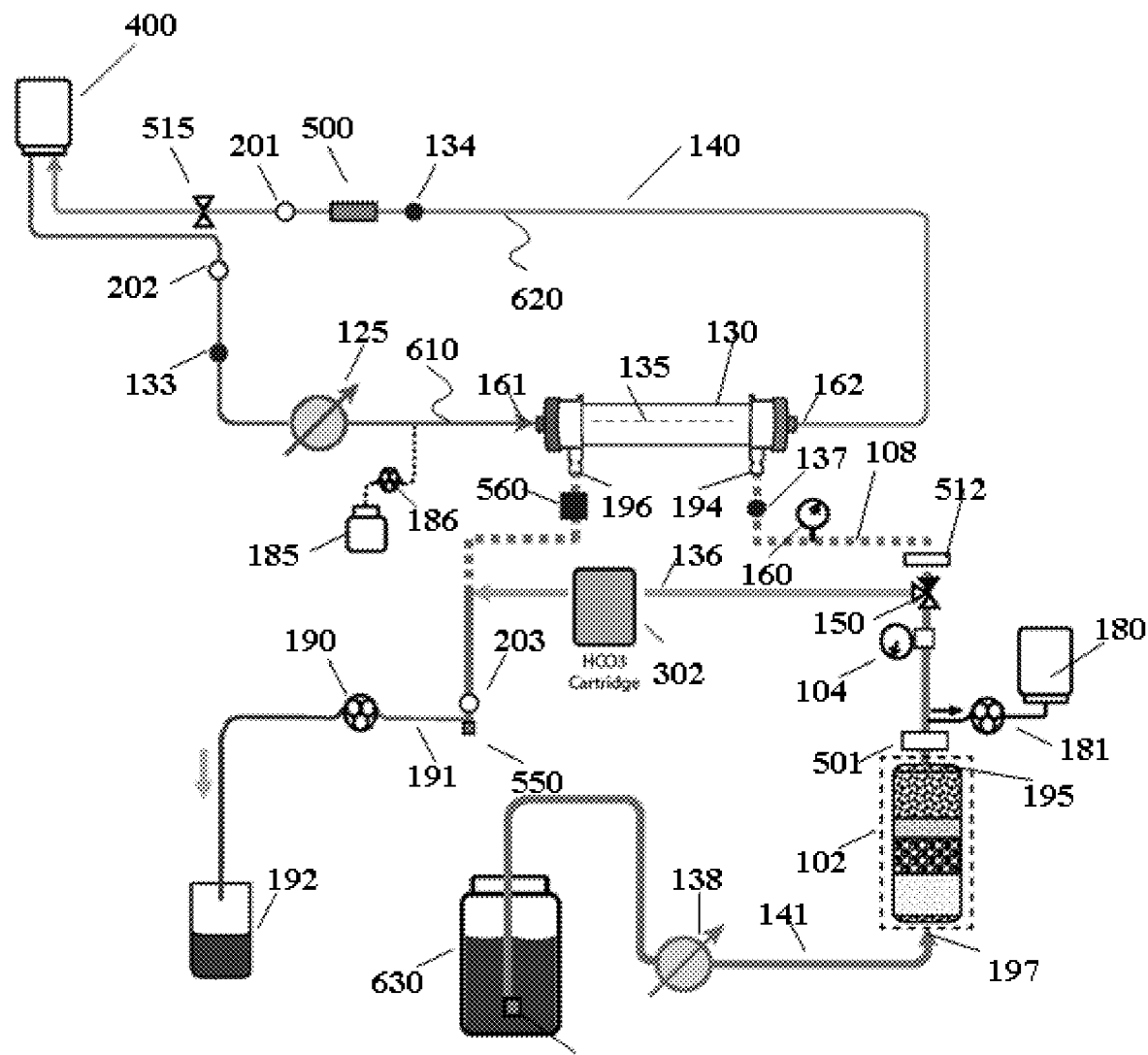
FIG. 16 shows a hemodialysis device having a controlled compliant dialysis circuit and an extracorporeal circuit undergoing a priming operation.

FIGS. 16 through 19 demonstrate a third alternative priming embodiment for the system. The dialysis circuit can include a pair of quick connectors 550 that are connected during normal operation to form the dialysis circuit 141 in a closed loop. The method illustrated by FIG. 16 requires both a saline solution 400 and water or other aqueous fluid present in container 630 (e.g. water with $NaHCO_3$ and dilute NaCl solution) to be provided to prime the extracorporeal circuit 140 and the dialysis circuit 141, respectively. As shown in FIG. 16, the blood pump 125 is run to fill the extracorporeal circuit 140 including the extracorporeal side of the dialyzer 130 with saline and the dialysate pump 138 is run to fill the dialysis circuit 141 with the fluid from container 630. The valve 150 is set to divert flow in the dialysate circuit 141 through the second bypass pathway 136.

Figure 17:
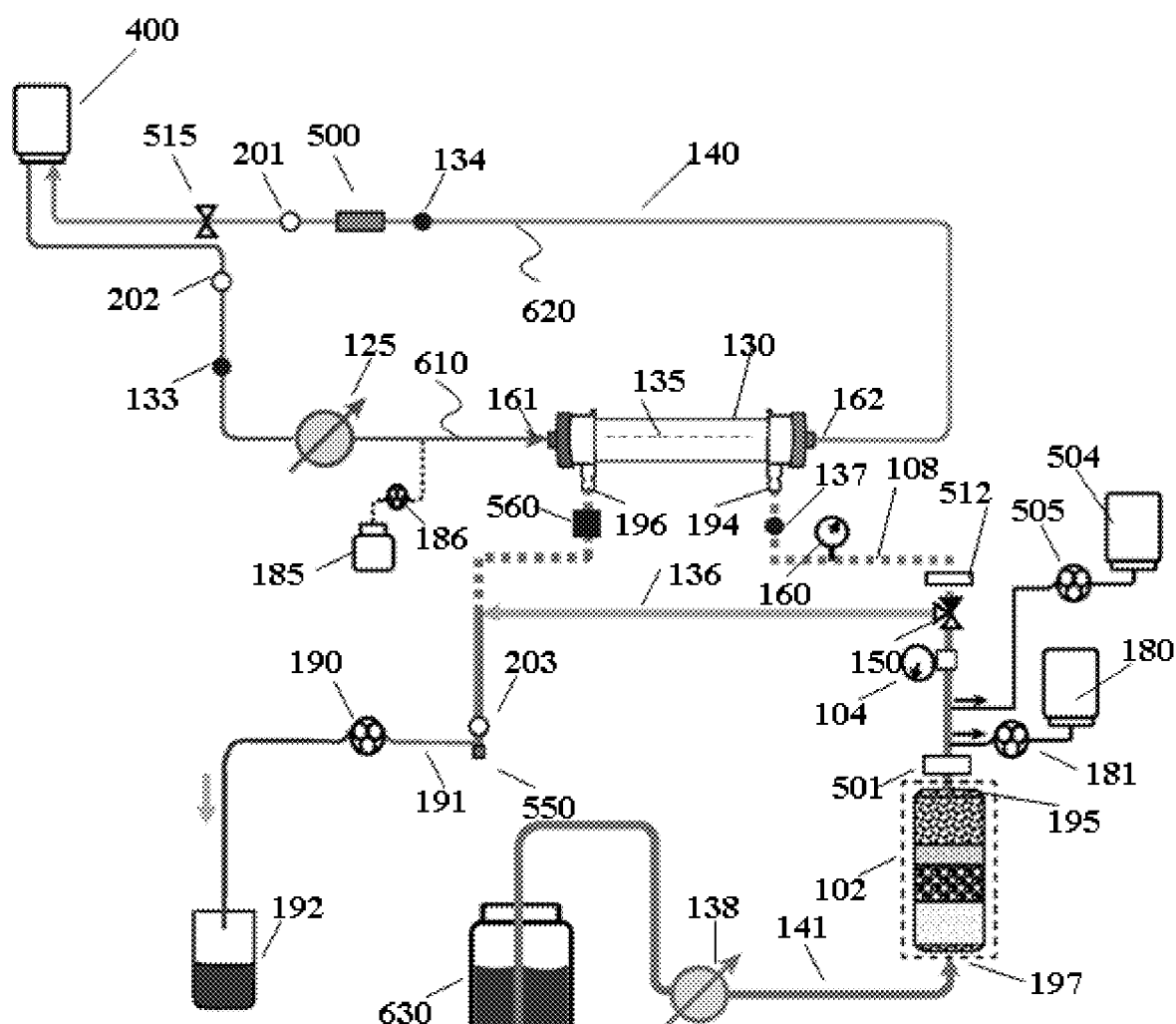
FIG. 17 shows a hemodialysis device having a controlled compliant dialysis circuit and an extracorporeal circuit undergoing a priming operation to reconstitute an infusate solution and a bicarbonate solution.
Figure 18:
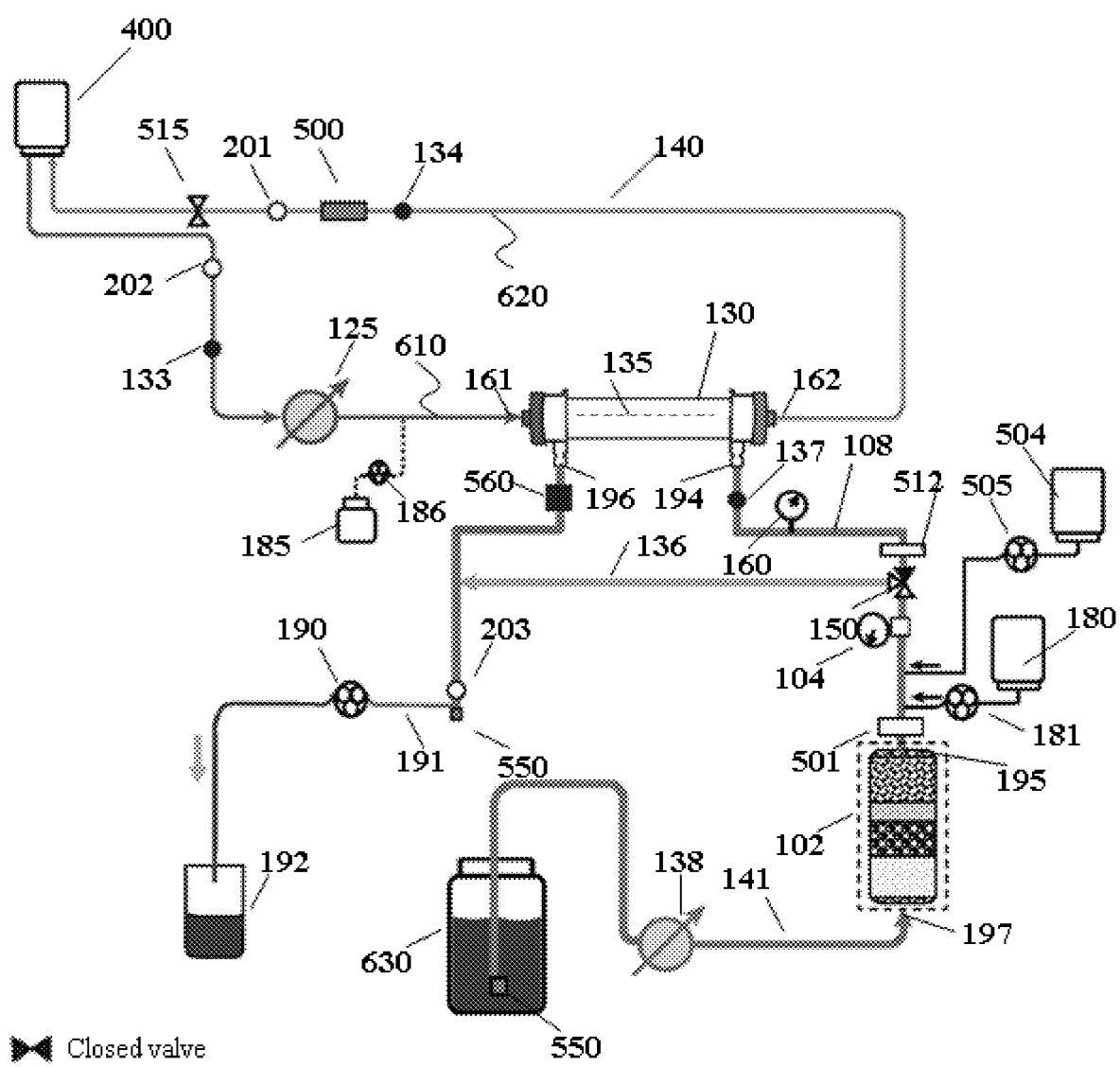
FIG. 18 shows a hemodialysis device having a controlled compliant dialysis circuit and an extracorporeal circuit undergoing a priming operation and adjustment of the composition of a dialysate.
Figure 19:
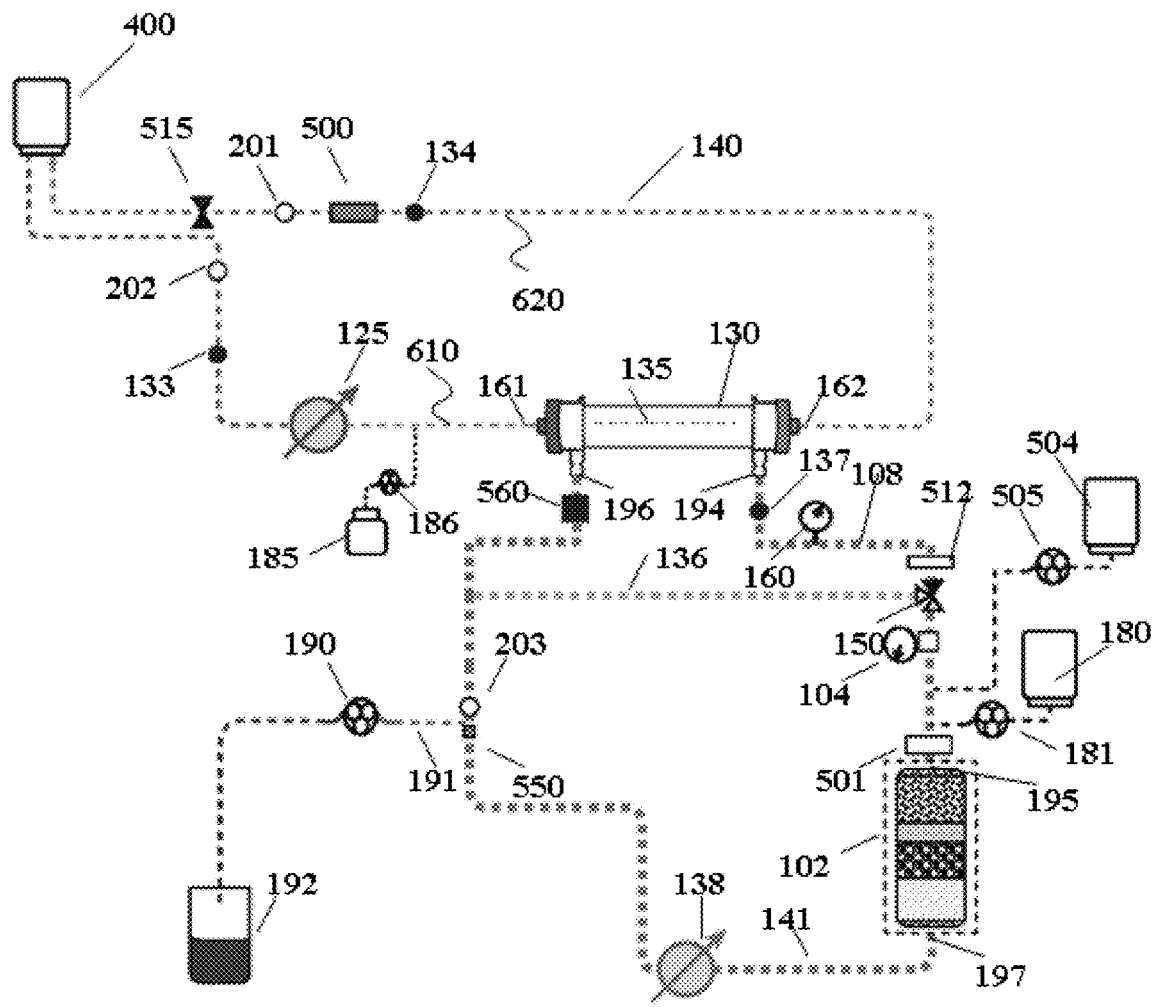
FIG. 19 shows a primed hemodialysis device that is ready for operation.

After the extracorporeal circuit 140 and the dialysate circuit 141, except for the dialyzer 130, are flushed with fluid, the bicarbonate pump 505 and the infusate pump 181 are run in a reverse direction to reconstitute a solid bicarbonate salt and solid infusate salts present in containers 504 and 180, respectively. The operation of pumps 505 and 181 is illustrated in FIG. 17. When the solid bicarbonate salt and the infusate salts are properly reconstituted, the bicarbonate pump 505 and the infusate pump 181 are run in their normal operating direction to adjust the composition of the priming fluid in the dialysis circuit 141, as shown in FIG. 18. After the composition of the dialysate is adjusted, the dialysis circuit side of the dialyzer 130 can be flushed with dialysate by operation of the valve 150.

After the extracorporeal circuit 140 and the dialysis circuit 141 are flushed with fluid having the correct composition, all pumps are stopped and the extracorporeal circuit is connected to the patient and the system is ready for operation. Optionally, tap water can be used to prime the dialysis circuit 141, where the action of the sorbent cartridge can remove impurity species from the tap water and the dialysis system can adjust the composition of the tap water to a composition suitable for use as a dialysate. The abilities of the described dialysis systems to adjust pH and electrolyte concentration in the dialysate can be used to prepare a dialysate from tap water used to prime the dialysis circuit 141.

The extracorporeal circuit and the dialyzer are typically provided sterile to the patient/user, while the dialysis circuit 141 and the sorbent cartridge 102 do not typically need to be provided sterile. Typically, the output of the sorbent cartridge in prior art sorbent systems meets the Association for the Advancement of Medical Instrumentation's (AAMI) Water for Hemodialysis standard but does not meet the AAMI standard for microbiologically ultrapure dialysate. It has been shown in the medical literature that ultrapure dialysate is desirable in reducing the inflammatory response in the ESRD patient. Desirable quality for ultrapure dialysate is less than about 0.1 colony forming unit (cfu)/mL where cfu is the number of viable cells per unit volume, and detectable endotoxins less than about 0.03 ELISA unit (EU/mL). In certain embodiments, the dialysate passing through the dialyzer 130 has low levels of both active bacteria and endotoxins. In one embodiment, a microbial filter 512 placed in the dialysis circuit 141 can be present to prevent bacteria and endotoxin from reaching the patient. Suitable filters include ultrafilters and microfilters manufactured or supplied by Minntech, Medica, Nikkiso, Pall Corporation or Millipore®, however any known by those of ordinary skill for the intended purpose can be used. Further, the sorbent cartridge 102 can include a spacer frit, which is a membrane or material that is designed to prevent fines from leaving the cartridge. After this spacer frit, an endotoxin or retentive membrane can be placed to prevent the passage of endotoxins and bacterial. Examples of an endotoxin or retentive membrane include quaternized amine charged surface membranes such as those manufactured or supplied by Pall Corporation (Ann Arbor, Mich.). Endotoxin levels can be measured using a qualified assay with *Limulus amebocyte* lysate assay using blood from the horseshoe crab through guidelines promulgated by the U.S. Food and Drug Administration or dialysis standards such as AAMI/ANSI/ISO 23500 Guidance for the preparation and quality management of fluids for hemodialysis and related therapies.

Figure 20:
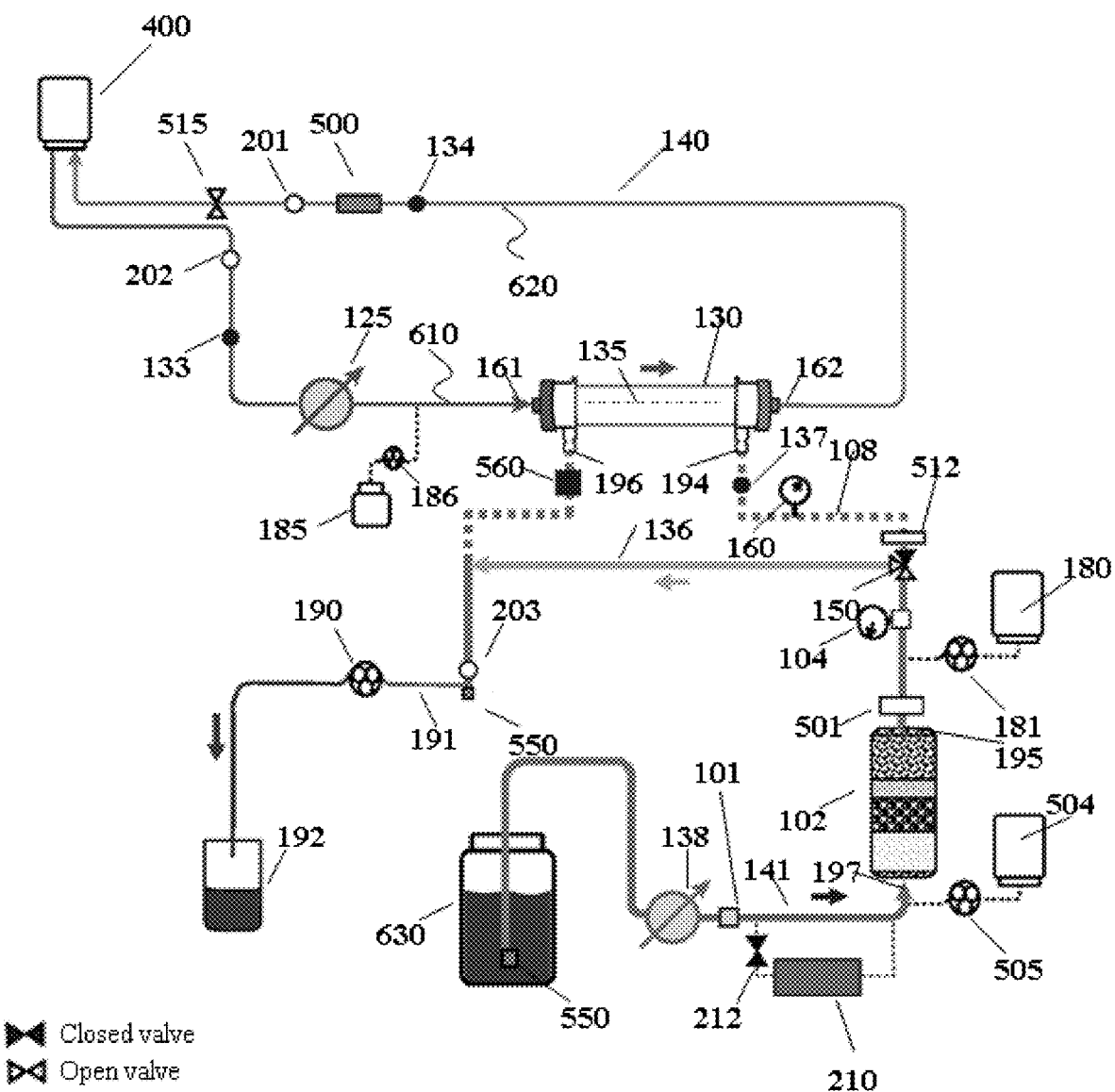
FIG. 20 shows a hemodialysis device having a controlled compliant dialysis circuit, an extracorporeal circuit and a deionization column undergoing a priming operation.
Figure 21:
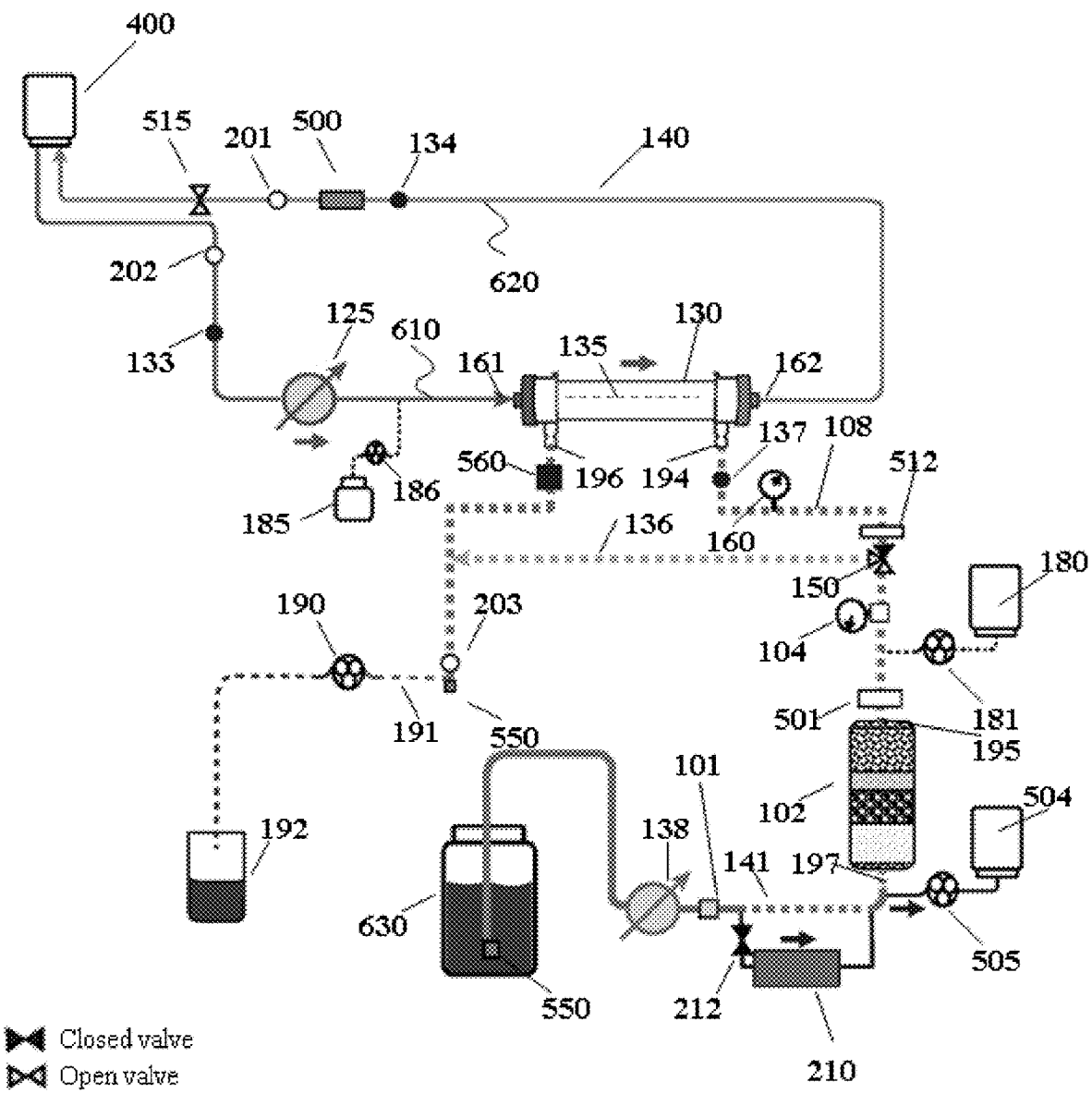
FIG. 21 shows a hemodialysis device having a controlled compliant dialysis circuit and a deionization column, where effluent from the deionization column is used to reconstitute a bicarbonate solution.
Figure 22:
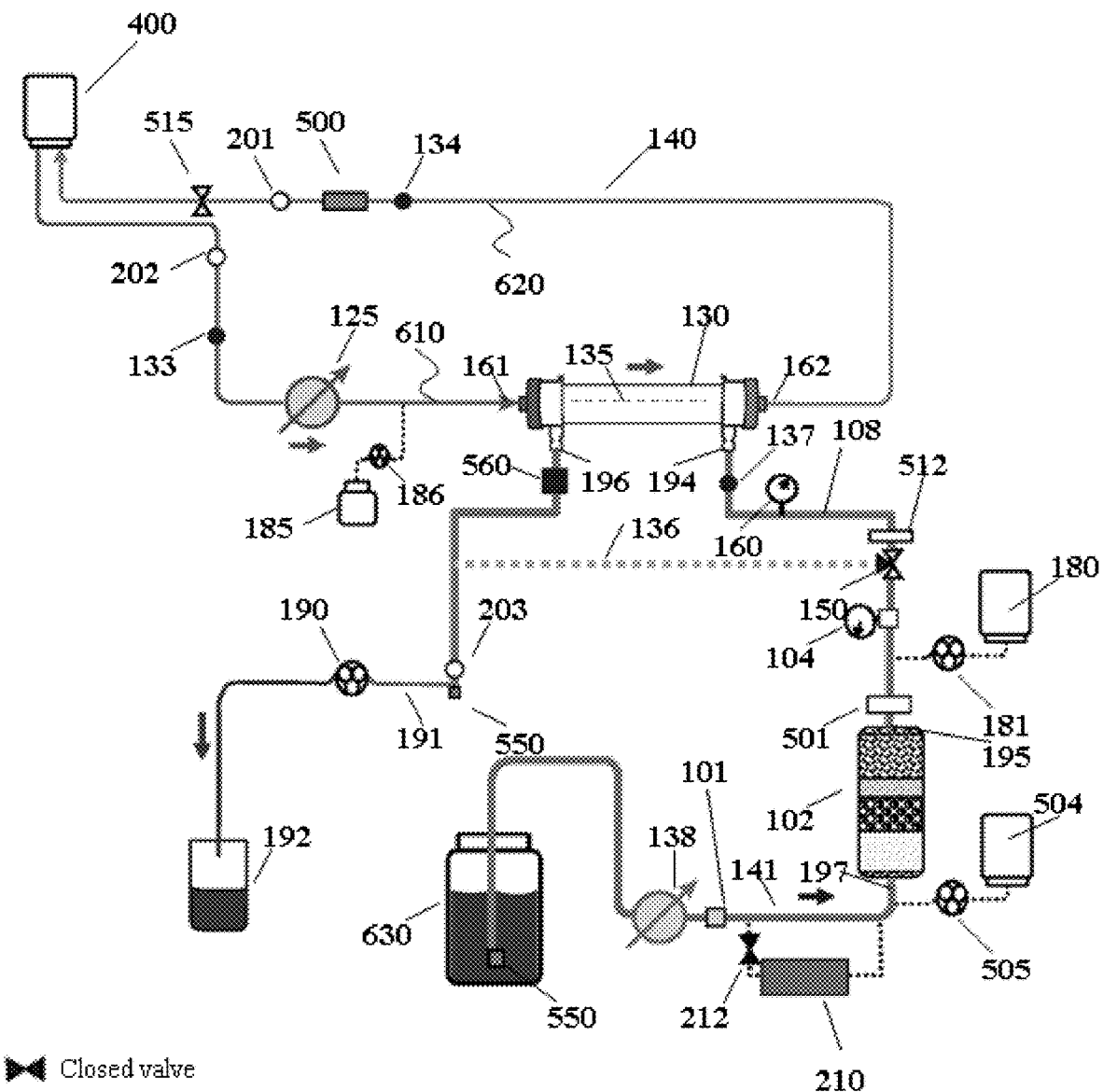
FIG. 22 shows a hemodialysis device having a controlled compliant dialysis circuit, an extracorporeal circuit and a deionization column undergoing a priming operation by purging air from a dialyzer.

FIGS. 20 through 22 demonstrate a fourth alternative priming embodiment. As shown in FIG. 20, the dialysis circuit 141 has a deionization cartridge containing a mixed bed de-I resin 210, where flow of fluid through the deionization cartridge 210 is controllable by valve 212. The dialysis circuit can include a pair of quick connectors 550 that are connected during normal operation to form the dialysis circuit 141 in a closed loop. The method illustrated by FIG. 20 requires both a saline solution 400 and water or other aqueous fluid present in container 630 (e.g. water with NaHCO$_3$ and dilute NaCl solution) to be provided to prime the extracorporeal circuit 140 and the dialysis circuit 141, respectively. For some sorbents that can be present in the sorbent cartridge 102, a weak saline solution in container 630 to maintain efficiency of the sorbents is desirable. If tap water is used for the fluid in container 630, then an activated carbon layer should be present as the first layer at the inlet of the sorbent cartridge 102 to absorb any metals and fluoride ions present in the tap water. The urease enzyme can be deactivated by metals and fluorides. As shown in FIG. 20, the blood pump 125 is run to fill the extracorporeal circuit 140 including the extracorporeal side of the dialyzer 130 with saline from container 400 and the dialysate pump 138 is run to fill the dialysis circuit 141 with fluid from container 630. The valve 150 is set divert flow in the dialysate circuit 141 through the bypass loop 136 during this stage of priming.

As shown in FIG. 21, valve 212 is adjusted to allow the priming fluid from container 630 to fill and prime the mixed bed de-I cartridge 210 and associated tubing. Due to the action of the mixed bed de-I resin, fluid eluting from the cartridge 210 is substantially deionized. If the fluid from container 630 does not contain any substantial non-ionic impurities, then the fluid eluting from the mixed bed de-I cartridge 210 is substantially pure water. During this stage of the system priming, it is feasible to run the carbonate pump 181 and the infusate pump 505 in reverse to reconstitute the contents of the carbonate container 180 and the infusate container 504, as previously described. At this stage, the bicarbonate salt and infusate salts can be reconstituted with the pure or deionized water eluting from deionization cartridge 210.

In FIG. 22, the valve 150 is adjusted to divert flow from the container 630 through the dialyzer 130. Fluid is pumped through the dialyzer 130 by the dialysate pump 136 until all of the air is removed from the dialysis circuit 141 as indicated by air-fluid detector 203. When air is indicated to be removed from the system, the pumps 125 and 138 will stop and the system will alert the patient or another individual. The quick connector 550 can be reconnected and the extracorporeal circuit 140 attached to the vasculature of a patient to begin treatment.

Figure 23:
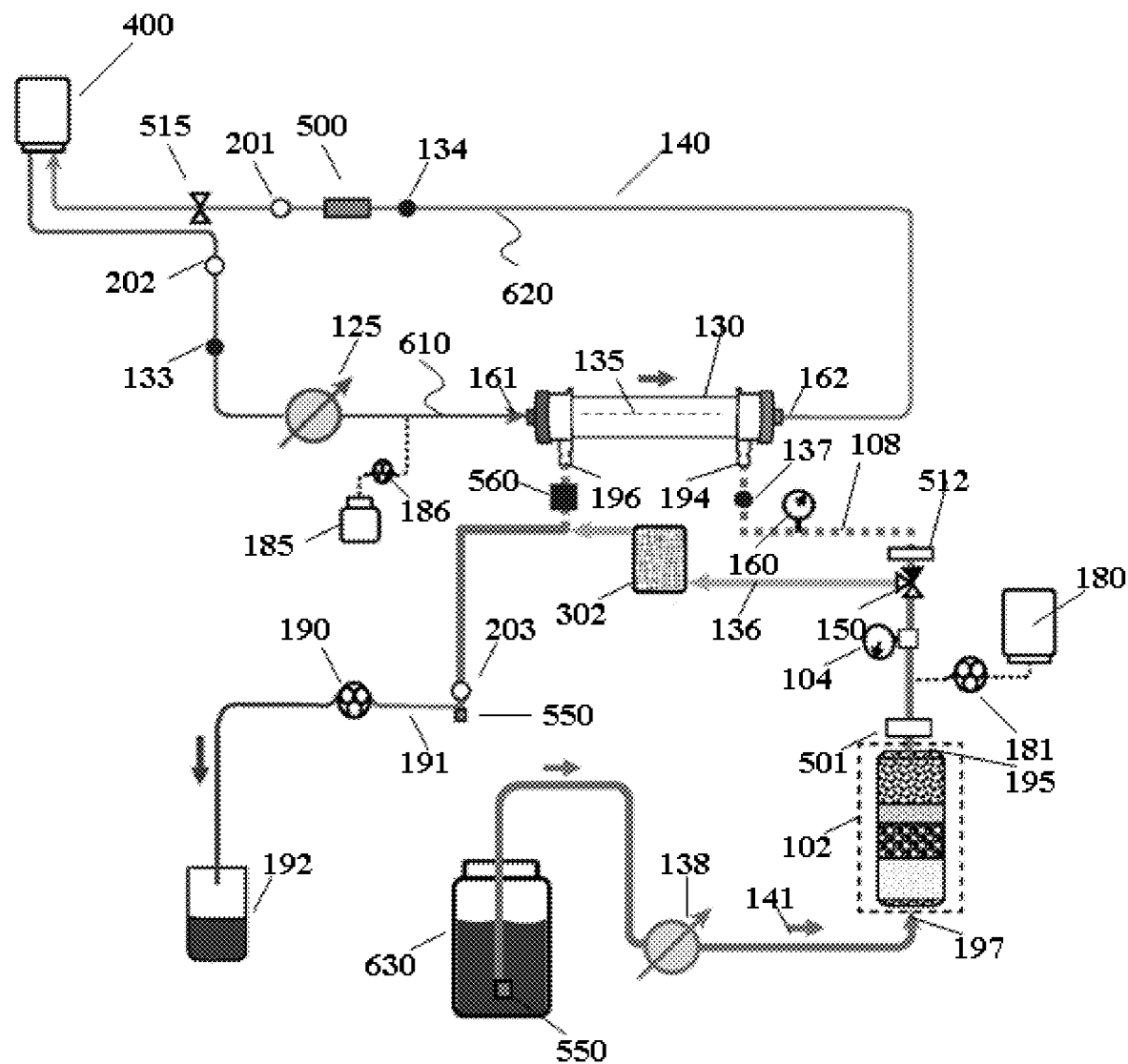
FIG. 23 shows a hemodialysis device having a controlled compliant dialysis circuit, an extracorporeal circuit and a bicarbonate column undergoing a priming operation.
Figure 24:
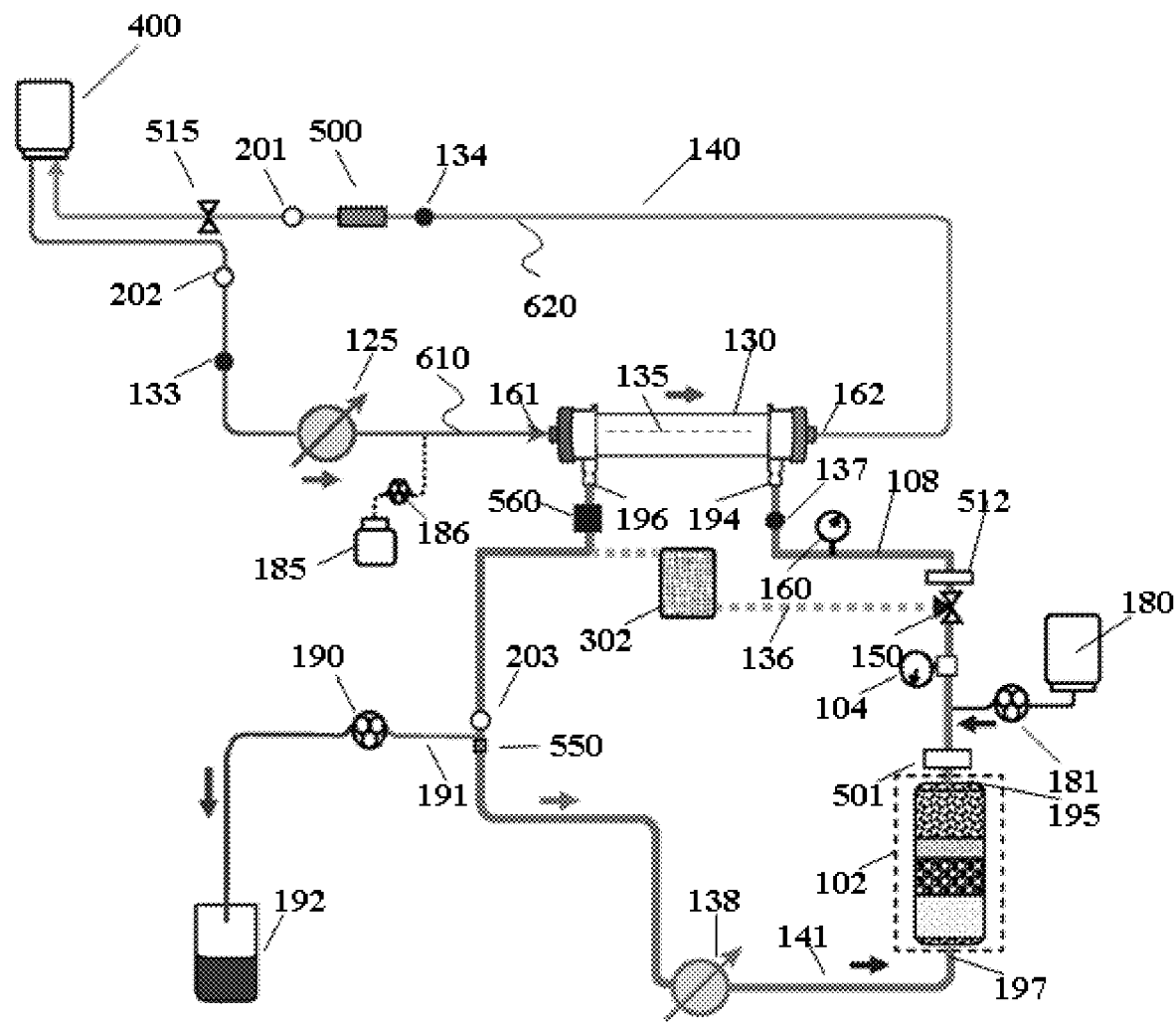
FIG. 24 shows a hemodialysis device having a controlled compliant dialysis circuit, an extracorporeal circuit and a bicarbonate column undergoing a priming operation by purging air from a dialyzer.

FIGS. 23 and 24 demonstrate priming of the system where a bicarbonate cartridge 302 is present in the dialyzer bypass loop 136. The dialysis circuit 141 can include a pair of quick connectors 550 that are connected during normal operation to form the dialysis circuit 141 in a closed loop. The method illustrated in FIG. 23 requires both a saline solution 400 and water or other aqueous fluid in container 630 (e.g. water with NaHCO$_3$ and dilute NaCl solution) to be provided to prime the extracorporeal circuit 140 and the dialysis circuit 141, respectively. For some sorbents that can be present in the sorbent cartridge 102, a weak saline solution in container 630 is retained to maintain efficiency of the sorbents. If tap water is used for the fluid in container 630, then an activated carbon layer should be present at the first layer at the inlet of the sorbent cartridge 102 to absorb any metals and fluoride ions present in the tap water. The urease enzyme can be deactivated by metals and fluorides. As shown in FIG. 23, the blood pump 125 is run to fill the extracorporeal circuit 140 including the extracorporeal side of the dialyzer 130 with saline from container 400 and the dialysate pump 138 is run to fill the dialysis circuit 141 with fluid from container 630. The valve 150 is set to divert flow in the dialysate circuit 141 through the bypass loop 136 during this stage of priming. The solid or powder bicarbonate salt will then dissolve in the fluid originating from container 630. When using the priming embodiment shown in FIG. 23, fluid passing through the bicarbonate cartridge 302 can form a saturating bicarbonate solution that will be available for use after hemodialysis treatment begins. If a less than saturating amount of bicarbonate is present in the cartridge 302, then the bicarbonate may be completely dissolved or excess powder may be lost to waste.

As shown in FIG. 24, the quick connector 550 can be reconnected after the bicarbonate cartridge 302 is full. This act is done to prevent wasting the contents of the bicarbonate cartridge. Valve 150 is set to divert the flow through the dialysis circuit 141 through the dialyzer 130 and remove air there from. The control pump 190 can be operated in an efflux direct to vent remaining air from the system as necessary or detected by air-fluid sensor 203. After air is removed from the extracorporeal circuit 140 and the dialysate circuit 141 as indicated by air-fluid sensors 201, 202 and 203, the infusate 505 and bicarbonate 181 pumps can be operated to adjust the composition of the fluid within the dialysis circuit 141.

Blood Return

Figure 25:
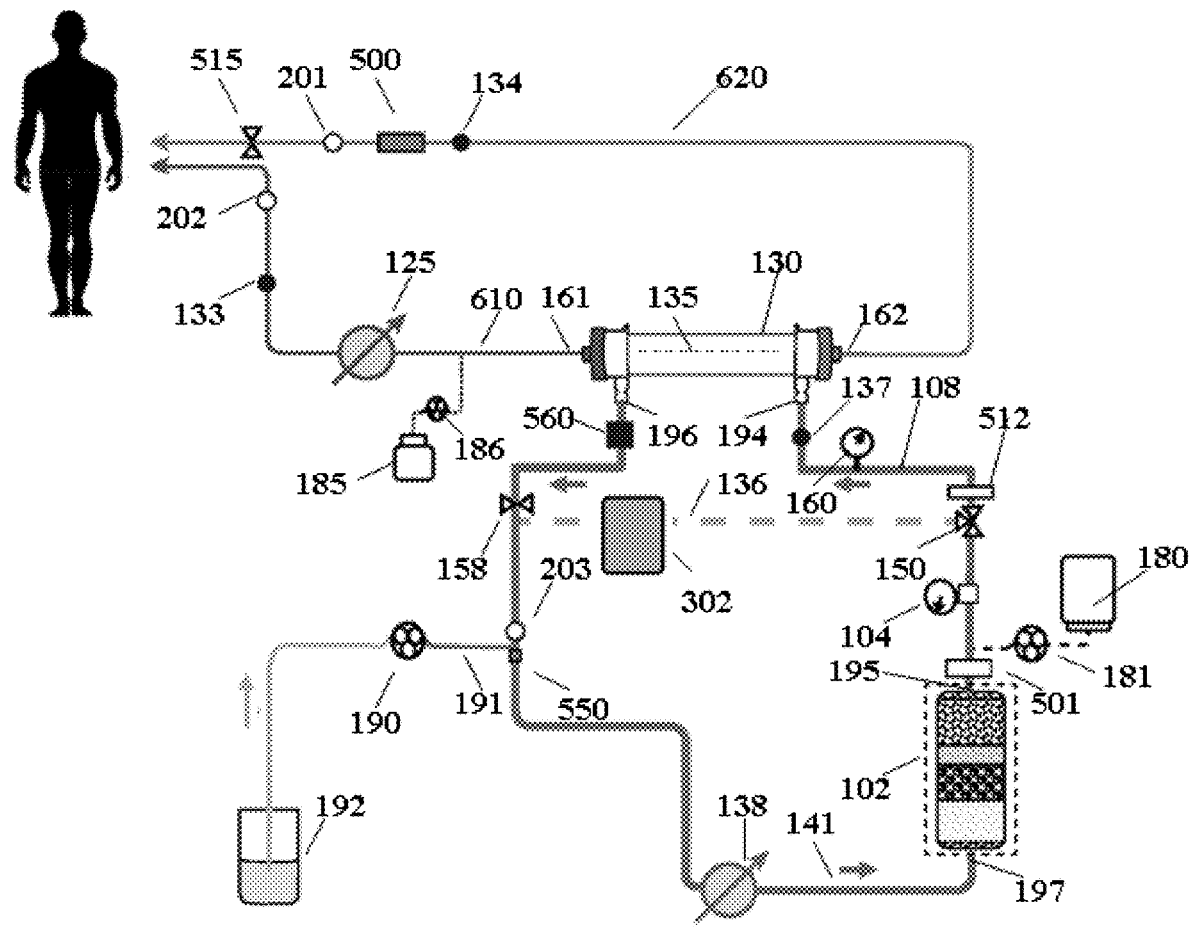
FIG. 25 shows a hemodialysis device having a controlled compliant dialysis circuit and an extracorporeal circuit undergoing an operation to return blood from the extracorporeal circuit to the patient.

After priming of the system as described above, the system is used in normal operation to accomplish the removal of impurities from the blood. However, blood in the extracorporeal circuit is preferentially returned to the body of the patient prior to disconnection of the extracorporeal circuit from the patient. With reference to FIG. 25, the return of blood to the patient at the end of treatment will be described.

The control pump 190 is run in the influx direction and the blood pump 125 is run in reverse at the same rate as the control pump 190. Through this operation, blood is forced down the arterial line 610 to return blood to the patient, where dialysate moves across the dialysis membrane 135 to fill the arterial line 610. An optical sensor 202 can be present to determine the presence of blood in the arterial line 610. Such an optical sensor 202 can function by passing a beam of light through the line to determine the amount of absorption to determine the presence of blood.

After the arterial line 610 is cleared of blood, the blood pump 125 is stopped while the control pump 190 continues to run in the influx direction. Since fluid cannot pass through the stopped blood pump 125 that is present along the arterial line 610, dialysate entering the extracorporeal circuit 140 pushes blood in the venous line 620 of the extracorporeal circuit 140 to return to the patient. In certain embodiments, an optical sensor 201 similar to the optical sensor present 202 on the arterial line 610 can determine if blood has been returned to the patient through the venous line 620. In certain other embodiments, the control pump 190 is run for an appropriate amount of time to return the volume of blood in the venous line to the patient without relying on information provided from optical sensors 201 and/or 202.

Quantization of Urea Removal

The blood of patients undergoing a regime of renal replacement therapy typically has blood chemistry determined by laboratory testing on a monthly basis to determine the effectiveness of treatment. Such testing is undertaken by a trained healthcare professional on a separate basis from the renal replacement therapy. Based upon lab results, various treatment metrics can be adjusted. For a patient utilizing the wearable sorbent system described herein without the aid of a healthcare professional, it is desirable to have a facility to determine the accuracy of treatment during therapy.

During treatment, the sorbent cartridge acts as a cation exchanger and releases sodium ions. The release of sodium by the sorbent cartridge has two principal sources:

1) Urea is converted to ammonium carbonate by the urease layer of the sorbent cartridge. The ammonium carbonate is exchanged to sodium and hydrogen in the zirconium phosphate layer(s) of the sorbent cartridge. The stoichiometry of the amount of sodium given off in this exchange is dependent on the processing of the zirconium phosphate layer; however, each process provides uniform results. Once the stoichiometry of ammonium/hydrogen/sodium exchange is known, the amount of sodium released from the sorbent cartridge can be used to quantify the amount of ammonium ion absorbed. By means of example, a representative example of the zirconium phosphate can operate to exchange 1 mEq Ammonium for 0.15 mEq sodium and 0.85 mEq hydrogen. In this example, if the cartridge removed 20 grams of urea during a treatment, it would require that the zirconium phosphate remove 1400 mEq ammonium, which would produce about 210 mEq of sodium. Those skilled in the art will readily recognize that other zirconium phosphate materials having a different stoichiometry of ammonium/hydrogen/sodium exchange can also be used to calculate the amount of urea converted to ammonium ion and absorbed.

2) The dialysis solution contains electrolytes such as calcium ($Ca^{2+}$), magnesium ($Mg^{2+}$) and potassium ($K^+$). These electrolytes remain in a stable range and close to constant in the dialysate during treatment. These electrolytes are totally removed from the spent dialysate by the sorbent cartridge. To ensure that there is a stable and correct concentration of electrolytes in the refreshed dialysate prior to reaching the dialyzer, zirconium phosphate exchanges these electrolytes with sodium. Then, the electrolytes are re-infused via an infusate pump to the correct concentrations. The amount of sodium produced from the zirconium phosphate layer due to this exchange is dependent on the dialysis solution flow rate, the time of treatment and the concentration values of these cations in the dialysis solution. For example, if the $Ca^{2+}$ were 3 mEq, the $Mg^{2+}$ 1 mEq, and the $K^+$ 1 mEq, the sorbent cartridge would produce approximately 240 mEq of sodium at a 20 mL/min flow rate and a total volume of 48 liters through the cartridge.

Due to the near constant amounts of ($Ca^{2+}$), magnesium ($Mg^{2+}$) and potassium ($K^+$) ions being exchanged by the sorbent cartridge, the conductivity difference between dialysate containing urea entering the sorbent cartridge compared with the refreshed dialysate exiting the sorbent cartridge can be used to quantify the amount of urea converted to ammonium ions and absorbed by the sorbent cartridge. If the temperature and composition of an electrolyte solution are constant, the resulting conductivity of the solution is constant. At the ranges of typical dialysis solutions, any change in sodium concentration will result in a linear increase or decrease in dialysate conductivity. The table below shows the concentration and conductivity of a typical dialysis solution at 25° C. Even though sodium is not the only contributor to conductivity in dialysis solution, NaCl and $NaHCO_3$ make up approximately 94% of the conductivity of a typical dialysate solution.

TABLE 1

Composition of a typical dialysate solution and conductivity contributed by individual species.

| Substance | mmol/L | mS/cm |
|---|---|---|
| NaCl | 103 | 10.68 |
| $NaHCO_3$ | 34.0 | 2.47 |
| KCl | 2.00 | 0.26 |
| CaCl | 1.75 | 0.35 |

TABLE 1-continued

Composition of a typical dialysate solution and conductivity contributed by individual species.

| Substance | mmol/L | mS/cm |
|---|---|---|
| MgCl | 0.50 | 0.09 |
| NaCH$_3$COO | 3.00 | 0.21 |
| Total Conductivity 25° C. | | 14.05 |

Figure 26:
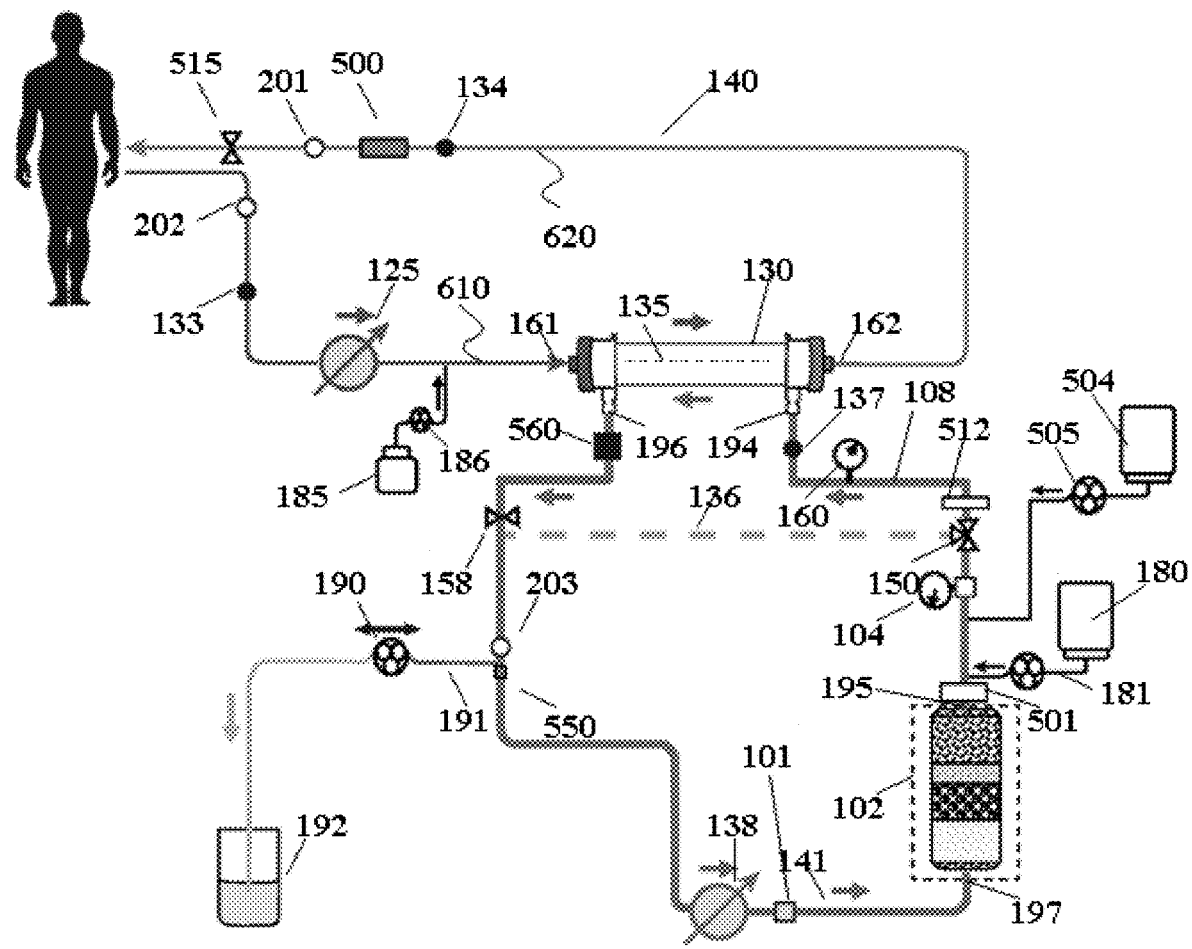
FIG. 26 shows a hemodialysis device having a controlled compliant dialysis circuit and an extracorporeal and at least two conductivity meters for determining an amount of urea absorbed by a sorbent cartridge.

Sodium concentration increases in the dialysate due to the exchange of ammonium to sodium, which can be used to verify if the urea was removed during the course of treatment. As shown in FIG. 26, conductivity meters 101, 104 and 160 can be incorporated into the system at the inlet and outlet of the sorbent cartridge. In certain embodiments, a conductivity meter can be present within the sorbent cartridge at the outlet of the zirconium phosphate layer. A conductivity at the inlet of the sorbent cartridge 102 is measured at a location between the dialysate outlet 196 of the dialyzer 130 and the sorbent cartridge 102. A conductivity at the outlet of the sorbent cartridge 102 is measured at a location between the sorbent cartridge 102 and the dialysate inlet 194 of the dialyzer 130. A microprocessor or controller can monitor the conductivity measured by the conductivity meters to analyze the changes in conductivity brought about by the following:
1) Conversion of urease to ammonium carbonate and subsequent exchange of ammonium carbonate to sodium, and
2) Any net change in conductivity due to the exchange of Ca$^{2+}$, Mg$^{2+}$, and K$^+$ into sodium, which can be treated as a constant value. The change due to removal of Ca$^{2+}$, Mg$^{2+}$, and K$^+$ is known and the increase due to sodium is known. In the example dialysis solution of Table 1, the Ca$^{2+}$, Mg$^{2+}$, and K$^+$ contribute 0.7 mS/cm of conductivity.

The change in conductivity due to the loss of Ca$^{2+}$, Mg$^{2+}$, and K$^+$ and the increase of sodium ions due to this exchange will be relatively constant during the treatment. From this information, a controller can then calculate the amount of conductivity increase due to the urea removal via the following sources:

Inlet Conductivity—Conductivity Contribution of Ca$^{2+}$, Mg$^{2+}$, and K$^+$=Starting Conductivity Outlet Conductivity—Increase in Conductivity due to exchange of Ca$^{2+}$, Mg$^{2+}$, and K$^+$ to Na$^+$=Corrected Outlet Conductivity Corrected Outlet Conductivity—Starting Conductivity=Conductivity Increase due to Conversion of NH$_4^+$ to Na$^+$ The following example quantization is based upon 48 liters of regenerated dialysis solution used during the course of treatment having typical concentrations of Ca$^{2+}$, Mg$^{2+}$, and K$^+$:

Inlet Conductivity=14.04 mS/cm Outlet Conductivity=14.32 mS/cm
1. 14.05 mS/cm−0.7 mS/cm=13.35 mS/cm Starting Conductivity
2. 14.32 mS/cm−0.5 mS/cm=13.8 mS/cm Corrected Outlet Conductivity
3. 13.8 mS/cm−13.35 mS/cm=0.45 mS/cm Conductivity Increase due to Conversion of NH$_4^+$ to Na$^+$
4. 0.45 mS/cm/0.1037 mS·L/mEq·cm=4.34 mEq/L Na$^+$ due to Urea Removal
5. 0.4 g urea per liter In hemodialysis, urea removal depends on the diffusive gradient across the dialyzer membrane. This gradient will be much higher at the beginning of treatment than at the end of treatment when typically 50 to 60 percent of the patient's urea has been removed. In certain embodiments, the conductivity values can be averaged so the curve of urea removal is understood and a continuous calculation need not be made. For example, conductivity can be sampled four or five times per treatment session for the purposes of quantifying urea removal. Early during a treatment session, a quantization of urea removal can be performed to verify that urea is being removed and that the Na$^+$ increase is relatively high. Later, quantization measurements can be performed to calculate a curve for urea removal and to predict total expected urea removal based on this curve. Hence, the amount of urea removed during treatment can be either accurately measured or estimated with a high degree of certainty.

Detection of Significant Clearance Problems

The urea removal monitoring facility described above can be used to indicate the proper operation of the system and to alert the patient to significant problems that would interrupt the waste removal process. This problem could be communicated automatically via WiFi™, the internet, or other communication means to a doctor or healthcare professional. For instance, a patient with impaired blood access flow would have little urea removed. In instances where low urea removed is monitored toward the beginning of treatment, an alarm can be communicated indicating a potential malfunction.

Access to the patient's vasculature can fail due to a buildup of plaque in the access stent. This plaque creates a stenosis at the distal end of the anastomosis where the stent or graft is sutured to the vascular system of the patient. When this occurs, the blood tends to recirculate within the access area and there is a lack of adequate flow of fresh blood into the extracorporeal circuit, which can result in the same blood being repeatedly dialyzed. Since little blood entering the dialyzer is from the systemic circulation, there is less urea in the blood and hence less sodium is produced from the cartridge due to urea/ammonium to sodium exchange. The lack of an adequate increase in conductivity can be detected by the system and an alert can be sent indicating a potential malfunction or problem accessing the patient's vascular system. This alert can indicate a lowered waste clearance, but the alert does not necessarily specify if the cause of the lowered waste clearance is due to a vascular access problem or due to a problem in dialysis flow, etc. A skilled medical professional can analyze the event to determine the cause of the alert in some embodiments.

Detection of Zirconium Exhaustion

After an extended period of use, the ability of the zirconium phosphate to adsorb urea can be exhausted. Exhaustion of zirconium phosphate leads to ammonium release into the dialysate, which can lead to ammonium intoxication in the patient. As discussed above, the exchange of urea/ammonium to sodium affects the output conductivity of the sorbent cartridge. Monitoring the inlet and outlet conductivities of the cartridge thus provides a method to detect ammonium breakthrough in the sorbent cartridge. An equilibration of the sorbent cartridge inlet conductivity with the output conductivity over a short time period indicates that the zirconium phosphate layer within the sorbent cartridge is exhausted. In certain embodiments, the conductivities pre- and post-sorbent cartridge are monitored. If an increase in sodium concentration is not detected by the controller, then the system will send an alert and prevent the dialysate from reaching the dialyzer, thus protecting the patient from ammonia intoxication.

Detection of Patient Hydration Status

The portable dialysis described herein can be used to perform ultrafiltration on a patient. During ultrafiltration, fluid is drawn out from the serum of the blood in the extracorporeal circuit through the dialysis membrane 135 by means of the control pump 190 as shown in FIG. 1A. Fluid removed by the control pump 190 is removed to the control reservoir 192. Ultrafiltration can be performed alone or in conjunction with convective clearance, as described above.

Patients having kidney failure may have an undesirable accumulation of fluid in body tissues that is called edema. As fluid (e.g. water) is removed from the patient's plasma, the volume of the patient's plasma is replaced by infusion of fluid from the patient's tissues. That is, the portable dialysis system does not directly access fluids stored in the patient generally but only directly accesses the patient's vascular system. Humans typically only have 5 to 6 L of plasma volume at any one time, where a significant time lapse can be required for plasma volume to be replaced by transfer to fluid from surrounding tissues.

During ultrafiltration, fluid can be removed too rapidly resulting in the patient becoming hypovolemic, which can cause several serious effects including hypotension, cramping, nausea and vomiting. To avoid instances of hemoconcentration due to excessive fluid removal, the rate of ultrafiltration is limited to a percentage of the blood flow through the extracorporeal circuit 140. In certain embodiments, the rate of ultrafiltration is limited to be no greater than about 30% of the plasma flow through the extracorporeal circuit 140. Plasma flow (Qp) is defined as Qp=Blood flow rate× (1-hematocrit), where blood flow rate is in units of volume divided by time (e.g. mL/min) and hematocrit is the unitless fraction of blood volume occupied by red blood cells. For example, if the blood flow rate is 60 mL/min and the hematocrit is 40%, then the maximum rate of ultrafiltration is set to be equal to about 10.8 mL/min or less.

The portable dialysis system can have a hematocrit detector to determine the hematocrit of blood containing within the extracorporeal circuit 140 of FIG. 1A. In certain embodiments, the hematocrit detector is a light source and a photodetector, wherein light emanating from the light source is passed through the blood in the extracorporeal circuit 140 and detected by the photodetector. The absorption of one or more wavelengths of light can indicate the level of hematocrit in blood entering the dialyzer 130 in the arterial line 610. In certain embodiments, the hematocrit detector gives an indication if the hematocrit trend is unsafe rather than giving a precise numerical quantification. In certain additional embodiments, the hematocrit detector can also determine if blood is present in the extracorporeal circuit 140, which can be useful during the processes of priming the system or returning blood to the patient as described above. A simple optical detector with a light source and a photodetector can also be used to detect whether there is blood in the system.

In most renal diseases, the kidneys fail to produce erythropoietin, a hormone that stimulates red blood cell production. Most ESRD patients take an erythropoietin stimulation drug to help produce red blood cells. These drugs are dosed to maintain a pre-treatment serum hematocrit of 32%. During the course of the dialysis treatment, the hematocrit can change due to the removal of fluid from the blood. Hematocrit level changes over the course of the treatment are an indication of relative blood volume changes over treatment. Fluid removal by ultrafiltration removes fluid from the blood plasma; however, red blood cells are left in the circulatory system. Depending on the rate of vascular fluid refilling from the tissues, the hematocrit will increase or decrease. A flat hematocrit indicates that the patient is most likely fluid overloaded even at the end of therapy. A steep increase in the slope of the hematocrit during fluid removal may portend a hypovolemic event prior to initiating a hypotensive episode. A gradual increase in hematocrit during the course of treatment is most likely indicative of a well-dialyzed patient.

Figure 27:
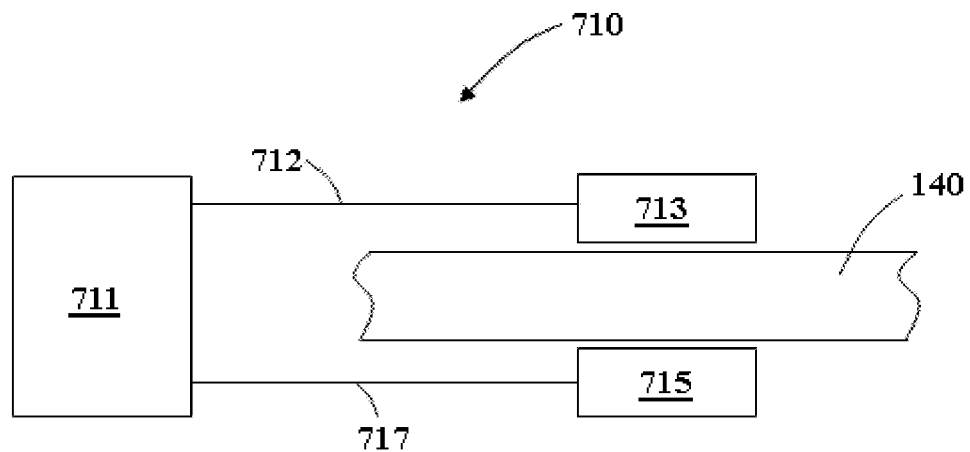
FIG. 27 shows a schematic for a hematocrit detector.

Hematocrit level is proportional to hemoglobin concentration. Therefore, any suitable sensor can be used to measure hemoglobin concentration, such as sensors used in pulse oximeters which measure adsorption of red and infrared light to determine concentration of oxygenated hemoglobin and deoxyhemoglobin, respectfully. The hematocrit/hemoglobin sensors, which may include the associated light source(s), can be placed in any suitable location. Placement of the hematocrit/hemoglobin sensor along the arterial line 610 of the extracorporeal circuit 140 will indicate the status of blood volume within the circulation of the patient. Placement of the hematocrit/hemoglobin sensor along the venous line 620 of the extracorporeal circuit 140 will indicate the extent of hemoconcentration occurring within the dialyzer 130. Measurement of hematocrit within the arterial line 610 can be used to calculate Qp as described above. Other optical based technologies that can determine the relative blood volume changes during the course of treatment can also be used to determine hydration status of the patient and whether the appropriate amount of fluid has been removed FIG. 27 shows a schematic for a hematocrit/hemoglobin/relative blood volume sensor 710. A light source 713 of appropriate wavelength (red or infrared) is positioned on one side of the tubing of extracorporeal circuit 140 such that the light passing through tubing hits detector 715. More light is absorbed (and less hits the detector 715) if a higher concentration of hemoglobin is present in the extracorporeal circuit 140. A lead 712 carries power and other electrical signals, if appropriate, to the light source 713 from the sensor device body 711, which may contain the power source and other control or detecting electronics. Lead 717 carries electrical signals from detector 715 to the components housed in sensor device body 711. Suitable hematocrit sensors are known, such as a CRIT-LINE monitor from HEMAMETRICS (see, HEMAMETRICS, CRIT-LINE hematocrit accuracy, Vol. 1, Techn Note No. 11 (Rev. D) Feb. 24, 2003).

In other embodiments, hemoconcentration and blood hydration status can be detected and monitored by a relative blood volume monitor. The relative blood volume monitor can detect a change in the concentration of measured solute, solid material or group of solutes and solid materials in the blood that are too large to cross the dialysis 135 or hemofiltration 200, which indicates a change in blood volume. The volume of blood typically is not measured by the relative blood volume monitor. The relative blood volume monitor measures the change in water content of the blood over the course of treatment, as implicated by a change in solute concentration, and does not require an absolute quantization of any particular solute in the blood. The relative blood volume monitor determines the relative blood volume hydration status (RBVHS) of the subject by measuring the level of one or more blood solutes or solid materials at a time close to the beginning of treatment, which can be assigned a value $C_0$. The level of the one or more blood solutes does not require an absolute quantification; rather the level of the one or more blood solutes or solid materials can be reported as the magnitude of a signal generated by the relative blood volume monitor. The level of the one or more solutes is measured periodically at a second later time, which can be assigned a value $C_t$. The relative blood volume hydration status can then be determined by the formula RBVHS=$C_0$/$C_t$.

In certain embodiments, the relative blood volume monitor is a hematocrit sensor and the one or more solutes measured by the relative blood volume monitor are oxygenated or deoxygenated hemoglobin. In certain other embodiments, the relative blood volume monitor is a device that measures the velocity of ultrasonic sound waves in the blood. Ultrasonic sound waves are defined as sound waves having a frequency above 20,000 Hz. The velocity of ultrasonic sound waves in blood is an indication of the total protein concentration in the blood.

The relative blood volume hydration status can be used in the same manner as hematocrit, described above, to determine the effectiveness of ultrafiltration. It is important to note that when using relative blood volume the trend slope is inverse to the trend slope when using a hematocrit sensor, i.e. as hematorcrit increases, relative blood volume decreases. A flat relative blood volume hydration status indicates that the patient is most likely fluid overloaded even at the end of therapy. A steep decrease in the slope of the relative blood volume hydration status during fluid removal can portend a hypovolemic event prior to initiating a hypotensive episode. A gradual decrease in relative blood volume hydration status during the course of treatment is most likely a well-dialyzed patient. In certain further embodiments, the relative blood volume hydration status determined by the relative blood volume monitor can be correlated to a fluid volume of the blood.

In the event that an unsafe level of hydration status is indicated by hematocrit level or by relative hydration status, a controller 801 associated with the system can stop the fluid removal and alert the patient. Controller 801 can be programmed to remove fluid via a gradual slope down in relative blood volume or up when monitoring hematocrit. Additionally, the controlled compliant nature of the dialysis circuit can be used to administer a bolus transfer of fluid to the patient. As described above, operation of the control pump 190 in the influx direction will cause a transfer of fluid volume from the control reservoir 192 to the extracorporeal circuit 140. The system can be preprogrammed to transfer a certain bolus volume to the patient upon detection of an unsafe trend in hematocrit or relative blood volume hydration status.

In certain embodiments, the control reservoir 192 is empty at the beginning of a treatment session wherein volume enters the control reservoir during treatment including ultrafiltration. As such, a bolus infusion in response to trend in hematocrit or relative blood volume hydration status is a return of fluid volume removed from the patient during treatment back to the patient. Any volume returned to the patient from the control reservoir 192 is cleaned by the sorbent cartridge 102 prior to introduction to the extracorporeal circuit 140. However, in other embodiments the control reservoir 192 can contain a volume of fluid at the beginning of treatment that can be used for a net infusion of fluid into the patient during the course of treatment.

Figure 28:
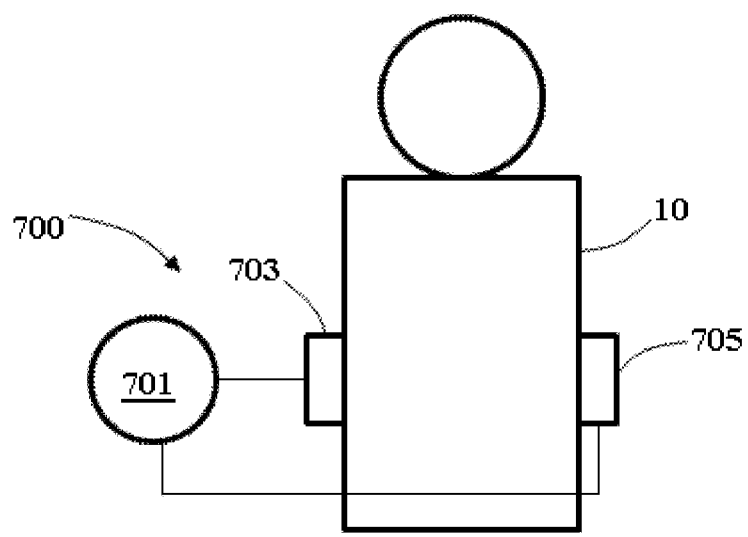
FIG. 28 shows a schematic for an impedance detector.

Hypovolemia can further be guarded against by simultaneously monitoring body fluid level of the patient undergoing hemodialysis treatment. The amount of fluid stored in body tissues outside the blood is proportional to the impedance that can be measured from the patient's body. As depicted in FIG. 28, impedance can be monitored between two electrodes 703 and 705 that are attached to the torso 10 of a human patient. The electrodes 703 and 705 are operably coupled to control and processing electronics 701 via leads. The electronics 701 are configured to generate a voltage differential between the electrodes 703 and 705, and current can be measured and impedance calculated. The measurement can be done in either DC or AC mode. Impedance or phase angle can be correlated to tissue fluid volume. Suitable external impedance monitors 700 and components that can be used in accordance with the teachings described herein are known. In certain other embodiments, electrodes 703 and 705 can be implanted within the patient.

One example of a well studied system that can be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., Siegenthalar, et al. Journal of Clinical Monitoring and Computing (2010): 24:449-451, and Wang, Am. J. Cardiology, 99(Suppl):3G-1-G, May 21, 2007. Alternatively or in addition, tissue impedance can be monitored for a suitable period of time to establish as suitable baseline, and patient markers can be used to instruct whether the patient is fluid overloaded or under-loaded. The data acquired by impedance sensor and input data regarding fluid status of the patient at the time the sensor data is acquired may be used to establish suitable ranges for impedance values.

One or more controllers 801 associated with the hemodialysis system can monitor the hematocrit/relative blood volume hydration status and impedance/body fluid level of the patient undergoing hemodialysis treatment. A typical hematocrit level for a dialysis patient is about 32%. Prior to a treatment session, the fluid volume of blood of a kidney disease patient can be elevated, thus hematocrit levels can be lower than desired The one or more controllers 801 monitoring hematocrit levels can adjust the rate of fluid removal or end ultrafiltration treatment when hematocrit level reaches the desired, predetermined range.

Fluid within a person's body is capable of moving from the body tissue to the blood and vice versa. As such, proper fluid levels in a patient can be described in terms of a ratio of tissue fluid to blood volume, as measured by hematocrit level. Hematocrit level of body fluid level can be monitored independently as described above. In general, blood is about 7% of body weight and total tissue fluid is about 60% of the body weight (including blood, extracellular and intracellular fluid). As such, a typical tissue fluid to blood fluid volume ratio of a healthy individual is in the range from about 6:1 to about 9:1 or can be in a range from 5:1 to 9:1. A measured ratio above this range indicates that blood is being withdrawn too quickly to allow for adequate equilibration of fluid between the blood and tissues of the patient. Fluid removal can be modified, stopped, or a fluid bolus administered as appropriate and preprogrammed into the one or more controllers 801 of the hemodialysis system.

Detection of Needle or Catheter Disconnection

It is well established in the art that pressure is not always a reliable means to detect separations of the venous blood return from the access of the patient. If this event occurs there is the risk of a life threatening blood loss and possible exsanguination. A conductive mat or holder can be used to detect blood leaks to the controller. The controller can then take the appropriate means to protect the patient by stopping the blood pump and alerting the patient. Other means to detect needle or catheter disconnections can be incorporated into the system such as monitoring of the impedance through the two needles or using pressure pulses.

Infusate Control

Figure 29:
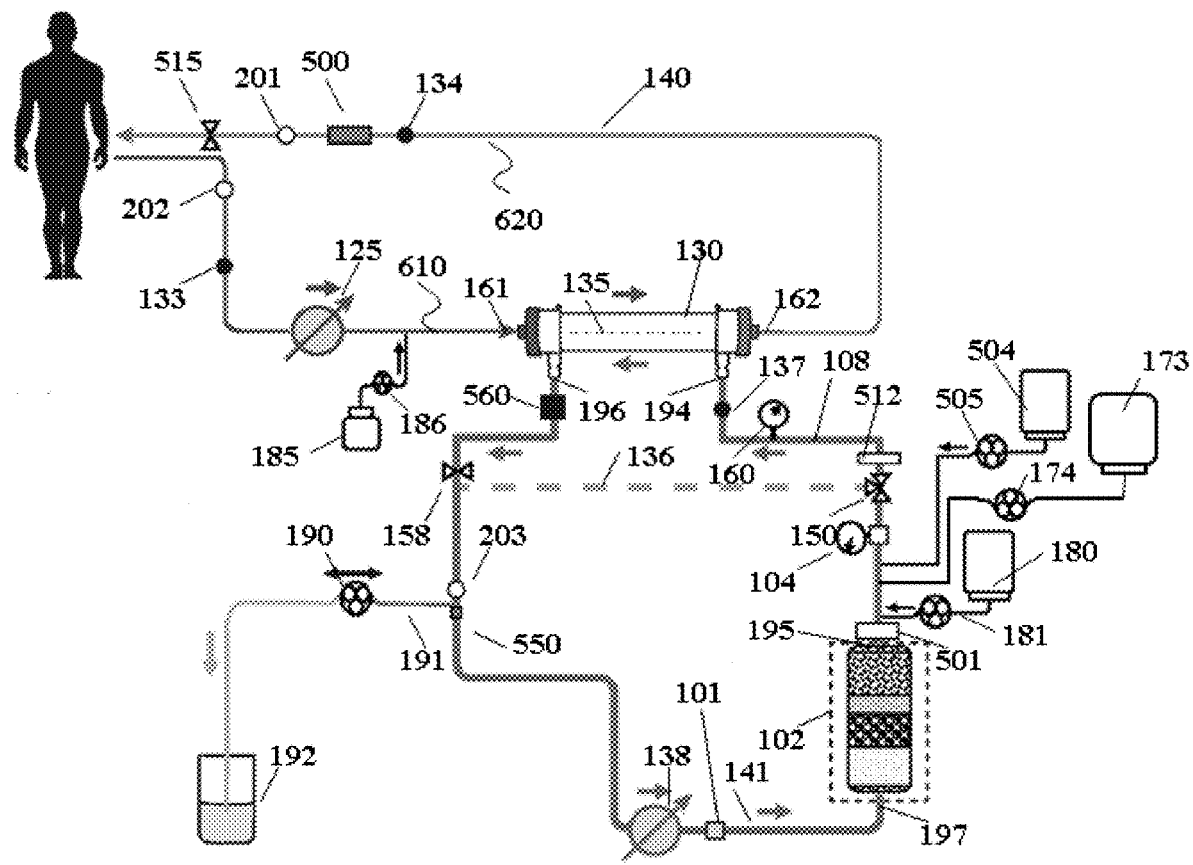
FIG. 29 shows a hemodialysis device illustrating a second control reservoir containing a fluid such as water.

As discussed above, a bicarbonate buffer can be added to the dialysate circuit 141 to maintain physiological pH and an infusate container can add cations to replace necessary electrolytes removed by the sorbent cartridge 102. In some embodiments, the second reservoir is a water reservoir 173 and the second reservoir pump is a water pump 174 that can also be present for adding water, tap water or purified water to the dialysis circuit 141 (or hemofiltration circuit 142) as necessary, as shown in FIG. 29. For example, water can be added as a diluent as needed to dilute conductivity and sodium ion concentration if other methods to reduce sodium ion concentration are unsatisfactory. The addition of water as a diluent can be particularly appropriate when it is necessary to divert dialysate and/or filtrate through the bypass pathway 136 due to conductivity being outside an acceptable range. Alternatively, reservoir 173 can contain a solution having a compatible physiological composition to be used as a dialysate or replacement fluid that can be added to the dialysis circuit 141 and/or hemofiltration circuit 174 as needed. Those skilled in the art will recognize that the inclusion of water reservoir 173 and pump 174 are optional and that container 173 and pump 174 can be included with any embodiment of a hemodialysis or hemofiltration system described herein. Conductivity of the ultrafiltrate or replacement fluid in hemofiltration circuit 142 can be monitored by conductivity meters 104 and 160 as described. As shown in FIG. 29, water can be added by a pump 174 at a position after the sorbent cartridge 102; however, those skilled in the art will recognize that water can be added to the dialysis circuit 141 and/or hemofiltration circuit 174 at any convenient location, and more particularly prior to the sorbent cartridge wherein such placement could be safer from a risk standpoint due to the possible risk of hemolysis.

Water Reservoir for Control of Convective Clearance

As described above, the water reservoir 173 and pump 174 can be present in any embodiment of the systems described herein, including the systems of FIGS. 1A and B. As described above, the control pump 190 can be operated in a bidirectional fashion to assist in the performance of convective clearance. Specifically, the control pump can be operated in the efflux direction to cause the movement of fluid from the extracorporeal circuit 140 into the dialysis circuit 141 and in the influx direction to cause the movement of fluid from the dialysis circuit 141 into the extracorporeal circuit 141.

In certain embodiments, operation of the control pump 190 in the influx direction can be substituted with operation of the pump 174 to drive liquid from the reservoir 173 into the dialysis circuit 141 and subsequently cause movement of fluid from the dialysis circuit 141 to the extracorporeal circuit across the dialysis membrane 135. The control pump 190 can be used for the movement of fluid in the opposite direction across the dialysis membrane 135. The pump 174 and reservoir 173 is used for the performance of convective clearance in embodiments of the invention where the total void volume of the dialysis circuit and working dialysate is less than about 0.5 L, or in embodiments where the void volume of the dialysis circuit and working dialysate is less than 1 L.

In certain embodiments, the volume of fluid held by reservoir 173 is about 1 L or less, or about 0.5 L or less. In certain embodiments, the volume of the fluid held by the reservoir is from about 0.1 L to about 1 L, from about 0.2 L to about 0.8 L, from about 0.5 L to about 1 L, from about 0.6 L to about 1 L, from about 0.5 L to about 0.8 L or from about 0.2 L to about 0.8 L.

Further Applications and Uses

One having skill in the art will readily recognize that the innovations disclosed herein are not limited to any specific application including not being limited to the removal of impurity or waste species from blood or any other biological or bodily fluid. The system having a controlled compliance dialysis circuit 141 and an additional circuit without a requirement for specifically controlled compliance (e.g. extracorporeal circuit 140) can be applied to any application where membrane-based diffusion or purification is applied. That is, dialysis or selective diffusion through a selectively permeable membrane is used in numerous applications where at least two fluids are contacted across a selectively permeable membrane to allow for exchange of material between the fluids. The innovations discloses herein allow for a selective diffusion process to occur while allowing for precise control of net fluid flow across the selectively permeable membrane.

Those skilled in the art will understand that extracorporeal circuit 140 for conveying blood can be substituted with another circuit 140 for circulating any suitable fluid, wherein the volume of fluid transferred between the external fluid and the fluid in the dialysis circuit 141 can be controlled. For example, the described systems can be applied to buffer exchange for pharmaceutical compositions, such as aqueous suspensions of biomolecules including oligonucleotides, proteins, and/or peptides, etc. Specifically, the circuit 140 can be adapted to be an external circuit 140 that is configured to circulate a pharmaceutical composition containing a solution or suspension of biomolecules. Concentrating a solution or suspension containing biomolecules is often problematic; however, it is often a requirement for pharmaceutical compositions to be provided at very specific concentrations. A common procedure for concentrating such solutions and suspensions is ultrafiltration, where a solution or suspension of biomolecules is contacted with an ultrafiltration membrane with centrifugal force used to drive water through the ultrafiltration membrane to generate a more concentrated solution or suspension. However, ultrafiltration is expensive and often solubility problems develop during the process where expensive biomolecules are lost during the process. As such, once a solution or suspension of biomolecules is prepared at a desired concentration, it is advantageous to avoid further changes in concentration.

Several techniques are known to achieve buffer exchange for a pharmaceutical or other aqueous solution or suspension of biomolecules. However, common techniques often lead to uncontrollable changes in volume and concentration, such as size exclusion chromatography. The systems described herein can be used to affect buffer exchange without any further changes in concentration or with a controlled change in concentration.

An external fluid being a solution or suspension of biomolecules in a first buffer can be provided and conveyed through the external circuit 140. A second buffer can be provided and conveyed in the dialysis circuit 141. The movement of fluid across the dialyzer 130 can be prevented to maintain the concentration of the solution or suspension of biomolecules during buffer exchanged. Alternatively, the solution or suspension of biomolecules can be selectively diluted to a desired concentration by operation of the control pump 190 to allow for a controlled movement of a volume of the second buffer across the membrane in the dialyzer 130. The second buffer present in the dialysis circuit 141 can be regenerated during operation through any suitable technique. For example, a mixed anion/cation deionization resin can be provided in the sorbent cartridge 102 to remove all buffer salts followed by regeneration of the second buffer by infusing of a concentrated buffer using infusate pump 180, as described above.

System Control

As described above, the systems described herein have several dynamic components including pumps and valves as well as detectors that determine the state of the system. As applied throughout this disclosure, operation of the system under the control of controller can refer to a single controller or multiple controllers having separate or overlapping function. A controller refers to a device having a programmable microprocessor and associated memory.

Figure 30:
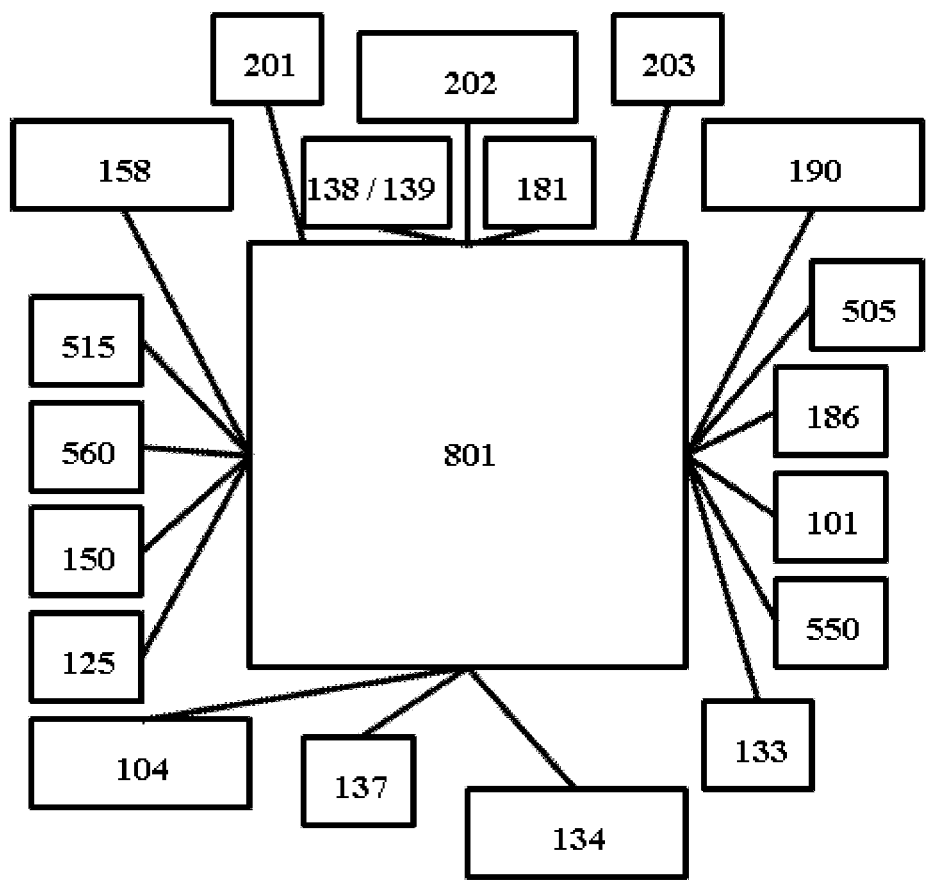
FIG. 30 shows a schematic for a controller in communication with various system components.

FIG. 30 shows one or more controllers 801 capable of sending and receiving data or instructions from several system components. The one or more controllers 801 can be more than one microprocessor unit. Specifically, the one or more controllers 801 are capable of controlling the pump rate and pumping direction of the blood pump 125, the dialysate pump 138, the filtrate pump 139 and the control pump 190 along with the operating of valve 150, valve 158, valve 212, and valve 515. The operation of heparin pump 181, bicarbonate pump 505 and infusate pump 181 is further under control of the one or more controllers 801. In two controller systems, one controller can be used to control the process and the other controller may be used to monitor the system and protect if the control is not correct. Alternatively in one controller systems, the processes that control or protect may be separate processes within the same controller.

The one or more controllers 801 also receives data from the various meters and detectors incorporated in the system including pressure meters 134, 135, and 137, optical and/or air-fluid detectors 201, 202, and 203, conductivity detectors 101, 104 and 160 and blood leak detector 560. Optionally, a detector, such as a pressure switch-type detector, a magnetic switch, or an optical detector, can be present to determine the connection state of quick connector 550. The one or more controllers 801 are capable of stopping or modifying operation of the system to protect the patient from an unsafe pressure reading indicating a malfunction or the presences of air in the extracorporeal circuit 140, an unsafe conductivity level or detection of a blood leak in the dialyzer 130. The one or more controllers are capable of stopping any of the pumps of the systems or operating valve 150 to bypass the dialyzer 130. Further, the one or more controllers 801 can modify or stop the operation of the system based upon the conductivity readings from the conductivity meters 101 and 104 as well as calculating an amount of urea absorption by the sorbent cartridge 102 and/or sodium entering or leaving the system through control pump 190. In two controller systems, one controller may be used to control the process and the other controller may be used to monitor and protect if the control is not correct.

In certain embodiments, the one or more controllers 801 are located remote from the dialysis and extracorporeal circuits. One of the controllers 801 can be a device that can send and receive data and instructions through a wired or wireless connection with the portable dialysis system. This data can be transferred automatically to an electronic medical record for automatic recording of patient data or a diagnostic device if the system malfunctions. Certain controller functions, for example, can be performed by an application that runs on a multipurpose computing device such as a cell phone, tablet, PC or PDA. In certain embodiments, a controller 801 that is remote to the portable dialysis system is capable of operating through a wired connection to the portable dialysis system to enable operation in hospital environments or airplanes where the use of wireless technology is restricted.

By locating one or more of the controllers 801 remote from the portable dialysis system, the majority of processing power does not have be carried by the patient thereby lowering the weight of the device. Devices and methods for controlling a device through wireless technology are known in the art. The wireless signals can employ signal confirmation, digital encoding algorithms, checksums and other verifications to minimize the effects of interference and to allow similar systems to operate in the same area. The system can have a safety feature to stop the device if the wireless control signal is interrupted or compromised.

It will be apparent to one skilled in the art that various combinations and/or modifications and variations can be made to the portable dialysis system depending upon the specific needs for operation. Moreover, features illustrated or described as being part of one embodiment may be used on another embodiment to yield a still further embodiment.

What is claimed is:

1. A system for performing kidney replacement treatment comprising:
    a hemodialysis system having an extracorporeal circuit, a controlled compliant dialysis circuit, a dialyzer with a dialyzer membrane, one or more controllers, and one or more pumps;
    wherein the extracorporeal circuit comprises
        a conduit for receiving blood from a subject;
        a conduit for returning blood to the subject; and
        a blood pump for conveying blood from the subject through the extracorporeal circuit and the dialyzer;
    wherein the controlled compliant dialysis circuit comprises
        a sorbent cartridge configured to remove at least one impurity or waste species from the dialysate, the sorbent cartridge having a dialysate inlet end and a dialysate outlet end;
        a dialysate pump for conveying dialysate from the sorbent cartridge to the dialyzer and back to the sorbent cartridge;
        one or more reservoirs configured to store fluid; and
        one or more pumps configured to provide bi-directional flow of fluid so as to selectively adjust the volume of the controlled compliant dialysis circuit;
    wherein the one or more controllers are configured to control the operation of the blood pump, the dialysate pump and the one or more pumps;
    wherein the one or more pumps are configured to provide selective adjustment of the volume of the controlled compliant dialysis circuit by
        (A) operating in an influx direction so that fluid moves from the one or more reservoirs to the controlled compliance dialysis circuit; and
        (B) operating in an efflux direction so that fluid moves from the controlled compliant dialysis circuit into the one or more reservoirs;
    wherein controlled compliance of the controlled compliant dialysis circuit is achieved by actively controlling, via the one or more controllers, the influx and efflux of fluid to and from both the dialysis circuit and the extracorporeal circuit;
    wherein a volume of fluid in the dialysis circuit, once the system is in operation, is substantially constant; and
    wherein the hemodialysis system provides fluid balancing without the use of scales or balancing chambers.

2. The system of claim 1, with the proviso that the blood pump and the dialysate pump are not pulsatile pumps.

3. The system of claim 1, wherein transfer of fluid by the one or more pumps results in substantially the same volume of fluid transferred to the body of the subject by transferring fluid from the one or more reservoirs to the dialysis circuit; and wherein the one or more pumps transfer fluid from the body of the subject to the system for performing kidney replacement treatment by transferring fluid from the dialysis circuit to the one or more reservoirs.

4. The system of claim 1, wherein the volume of the dialysate within the dialysis circuit is a substantially inflexible volume.

5. The system of claim 1, wherein a void volume for accommodating the dialysate in the sorbent cartridge, the dialyzer, and conduits comprising the dialysis circuit has a substantially inflexible volume.

6. The system of claim 1, further comprising a relative blood volume monitor to determine the relative blood volume hydration status (RBVHS) of the blood in the extracorporeal circuit, the relative blood volume monitor configured to send information to the one or more controllers, wherein the relative blood volume monitor determines the level ($C_0$) of one or more solutes in the blood at a first time and determines the level ($C_t$) of the one or more solutes in the blood at a second time later than the first time, and the relative blood volume hydration status is calculated by the formula RBVHS=$C_0/C_t$, wherein optionally the relative blood volume monitor is configured to determine the fluid volume of the blood at a position prior to the blood entering the dialyzer.

7. The system of claim 1, wherein the one or more controllers control operation of the one or more pumps to intermittently switch between an efflux direction to move fluid across the dialysis membrane from the extracorporeal circuit to the dialysis circuit and a second influx direction to move fluid across the dialysis membrane from the dialysis circuit to the extracorporeal circuit.

8. The system of claim 1, wherein the one or more controllers control the blood pump and the dialysate pump to pump blood and dialysate at a ratio of flow rates of about 1:1.5 to about 3:1.

9. The system of claim 1, further comprising a second reservoir and a second reservoir pump.

10. The system of claim 1, further comprising a first conductivity meter for measuring the conductivity of the dialysate at a position between the dialyzer and a dialysate inlet end of the sorbent cartridge;
a second conductivity meter for measuring the conductivity of the dialysate at a position between the dialyzer and a dialysate outlet end of the sorbent cartridge; and
one or more controllers for comparing the conductivity measured by the first conductivity meter and the second conductivity meter and calculating the amount of urea absorbed by the sorbent cartridge.

11. The system of claim 10, wherein the one or more controllers calculates the amount of urea absorbed by the sorbent cartridge by:
calculating a starting conductivity by subtracting a conductivity attributed to a substantially constant concentration of $Ca^{2+}$, $Mg^{2+}$, and $K^+$ ions in the dialysate from a conductivity measured by the first conductivity meter;
calculating a corrected outlet conductivity by subtracting an increase in conductivity attributed to an exchange of $Ca^{2+}$, $Mg^{2+}$, and $K^+$ ions for $Na^+$ ions by the sorbent cartridge from a conductivity measured by the second conductivity meter; and
calculating a conductivity increase from the exchange of $NH_4^+$ for $Na^+$ ions by the sorbent cartridge by subtracting the starting conductivity from the corrected outlet conductivity.

12. The system of claim 1, further comprising a second reservoir and a second reservoir pump wherein the second reservoir holds a fluid that can be added to the dialysis circuit by operation of the second reservoir pump, wherein addition of the fluid by the second reservoir pump causes the movement of fluid from the dialysis circuit to the extracorporeal circuit, wherein the one or more controllers control a rate of the second reservoir pump.

13. A method for performing convective clearance using the system of claim 1, comprising:
attaching the vasculature of a subject to the extracorporeal circuit such that a first end of the extracorporeal circuit draws blood from the subject and a second end of the extracorporeal circuit returns blood to the subject;
conveying blood from the subject through the extracorporeal circuit and the dialyzer and returning the blood to the subject;
conveying a dialysate through the controlled compliance dialysis circuit such that the dialysate moves from the sorbent cartridge, to the dialyzer and back to the sorbent cartridge, where at least one waste species diffuses from the blood to the dialysate through the dialysis membrane and the sorbent cartridge substantially removes at least one impurity or the at least one waste species from the dialysate; and
operating the one or more pumps such that fluid from the one or more reservoirs is added to the dialysis circuit in an influx direction or such that fluid is removed from the dialysis circuit in an efflux direction, and intermittently switching the one or more pumps between:
(1) the efflux direction, to move fluid across the dialysis membrane from the extracorporeal circuit to the dialysis circuit, and
(2) the influx direction, to move fluid across the dialysis membrane from the dialysis circuit to the extracorporeal circuit; and
adjusting an overall volume of fluid in the extracorporeal circuit and the controlled compliance dialysis circuit by selectively moving fluid to and from the one or more reservoirs, wherein a volume of fluid in the dialysis circuit once the system is in operation is substantially constant.

14. The method of claim 13, wherein the intermittent switching of the one or more pumps accomplishes the convective clearance of the at least one waste species.

15. The method of claim 14, wherein the at least one waste species has a molecular weight less than about 66000 g/mol.

16. The method of claim 13, wherein the one or more pumps are intermittently switched between the efflux direction and the influx direction such that the one or more pumps are not operated continuously in either the efflux or influx directions for a time period exceeding about 2 minutes.

17. The method of claim 13, wherein a volume of fluid added to the dialysis circuit by the one or more pumps results in substantially the same volume of fluid transferred to the body of the subject; and wherein a volume of fluid removed from the dialysis circuit by the one or more pumps results in substantially the same volume of fluid transferred from the body of the subject to the system for performing kidney replacement treatment.

18. The method of claim 13, further comprising measuring the conductivity of the dialysate using a conductivity meter.

19. A system for performing kidney replacement treatment, comprising:
- a hemofiltration system having a controlled compliance filtration circuit, a hemofilter with a hemofiltration membrane, wherein a volume of fluid in the dialysis circuit once the system is in operation is substantially constant, a blood inlet end for receiving blood, a blood outlet end for allowing blood out of the hemofilter, and an ultrafiltration outlet for allowing an ultrafiltrate out of the hemofilter;
- an extracorporeal circuit having a conduit for receiving blood from a subject and a conduit for returning blood to the subject, and a blood pump for conveying blood from the subject, to the hemofilter and back to the subject;
- a hemofiltration circuit having a sorbent cartridge for removing, from the ultrafiltrate, at least one impurity or at least one waste species to generate a replacement fluid, wherein the ultrafiltrate enters an inlet end of the sorbent cartridge and a replacement fluid exits an outlet end of the sorbent cartridge, the hemofiltration circuit having one or more conduits and a filtrate pump for conveying the ultrafiltrate from the hemofilter to the sorbent cartridge and one or more conduits fluidly connecting the outlet end of the sorbent cartridge to the extracorporeal circuit at a point of introduction of replacement fluid;
- at least one control reservoir for storing fluid removed from the hemofiltration circuit by at least one control pump, or for storing fluid that can be added to the dialysis circuit by the at least one control pump, the at least one control reservoir fluidly connected to the hemofiltration circuit;
- one or more controllers for controlling a rate of the blood pump, a rate of the filtrate pump, and a rate of the at least one control pump, wherein the one or more controllers adjust a volume of fluid in the extracorporeal circuit and the hemofiltration circuit by selectively moving fluid to and from the at least one control reservoir wherein a volume of fluid in the hemofiltration circuit once the system is in operation is substantially constant;
- wherein controlled compliance of the controlled compliant filtration circuit is achieved by actively controlling, via the one or more controllers, the influx and efflux of fluid to and from both the dialysis circuit and the extracorporeal circuit;
- wherein a volume of fluid in the dialysis circuit, once the system is in operation, is substantially constant; and
- wherein the hemofiltration system provides fluid balancing without the use of scales or balancing chambers.

20. The system of claim 19, wherein a rate of conveyance of the replacement fluid is substantially equal to the rate of operation of the filtrate pump.

21. The system of claim 1, wherein the one or more pumps are operable to pump fluid bi-directionally to actively control the transfer of fluid volume into or out of a compartment or circuit.

22. The system of claim 1, wherein the one or more pumps is a pair of pumps for moving fluid bi-directionally into and out of the dialysis circuit and the extracorporeal circuit.

23. The system of claim 1, further comprising a microbial filter in the dialysis circuit upstream of the dialyzer.

24. The system of claim 19, further comprising a microbial filter in the hemofiltration circuit upstream of the point of introduction of replacement fluid into the extracorporeal circuit.

25. The system of claim 1 further comprising a deionization cartridge for removing sodium ions from the dialysate, wherein the deionization cartridge is fluidly connected to the dialysis circuit.

26. The system of claim 1, wherein the one or more controllers are further configured to keep the rate of the blood pump, the dialysate pump, and the one or more pumps substantially the same as one another.

27. The system of claim 25, wherein the dialysate circulated through the deionization cartridge has a substantially deionized purified water with low conductivity.

28. The system of claim 1, wherein the one or more controllers are further configured to keep the rate of the one or more pumps positioned on the first set of one or more conduits, the second set of one or more conduits, the first conduit, and the second conduit, the rate of the blood pump, the rate of the water pump, the rate of the bicarbonate pump, and the rate of the dialysate pump substantially same with each other.

* * * * *